United States Patent
Sanderson et al.

(10) Patent No.: US 6,610,692 B1
(45) Date of Patent: *Aug. 26, 2003

(54) THROMBIN INHIBITORS

(75) Inventors: Philip E. Sanderson, Philadelphia, PA (US); Bruce D. Dorsey, Maple Glen, PA (US); Terry A. Lyle, Lederach, PA (US); Matthew G. Stanton, North Wales, PA (US); Donnette Staas, Lansdale, PA (US); Adel M. Naylor-Olsen, Lansdale, PA (US); Craig Coburn, Skippack, PA (US); Matthew M. Morrissette, Pottstown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/429,741

(22) Filed: Oct. 28, 1999

Related U.S. Application Data
(60) Provisional application No. 60/106,417, filed on Oct. 30, 1998.

(51) Int. Cl.$^7$ .................. A61K 31/497; A61K 31/5025; C07D 403/12; C07D 471/04; C07D 487/04
(52) U.S. Cl. .................. 514/248; 544/405; 544/236; 514/255.05; 514/300; 514/303; 514/337; 514/338; 514/339; 546/113; 546/117; 546/118; 546/119; 546/122; 546/268.4; 546/272.1; 546/273.4; 546/275.7; 546/277.1; 546/277.4
(58) Field of Search ................ 544/405, 230; 514/255.05, 248

(56) References Cited

U.S. PATENT DOCUMENTS

| | | | |
|---|---|---|---|
| 5,260,307 A | 11/1993 | Ackermann et al. | |
| 5,405,854 A | 4/1995 | Ackermann et al. | |
| 5,455,348 A | 10/1995 | Austel et al. | |
| 5,459,142 A | 10/1995 | Tone et al. | |
| 5,510,369 A | 4/1996 | Lumma et al. | |
| 5,744,486 A | 4/1998 | Sanderson et al. | |
| 5,866,573 A | 2/1999 | Sanderson et al. | |
| 5,981,546 A | 11/1999 | Duggan et al. | |
| 6,180,627 B1 * | 1/2001 | Blagg et al. | 514/235.8 |
| 6,403,583 B1 * | 6/2002 | Lam et al. | 514/237.2 |

FOREIGN PATENT DOCUMENTS

| | | |
|---|---|---|
| EP | 0 262096 A1 | 9/1987 |
| EP | 0509769 A2 | 4/1992 |
| EP | 997474 * | 5/2000 |
| WO | WO 94/25051 | 11/1994 |
| WO | WO 96/11697 | 4/1996 |
| WO | WO 96/31504 | 10/1996 |
| WO | WO 96/32110 | 10/1996 |
| WO | WO 97/01338 | 1/1997 |
| WO | WO 97/40024 | 10/1997 |
| WO | WO 99/11267 | 3/1999 |

OTHER PUBLICATIONS

Kitazawa, et al., "Preparation of 1,4-disubstituted cyclic amino derivatives as serotonin antagonists," Database CA on Stn., Document No. 129:302552, Abstract, WO 98 43956, (1998).

Peter R. Berstein, et al., "Nonpeptidic Inhibitors of Human Leukocyte Elastase . . . " *J. Med. Chem.*, vol. 37, 1994, pp. 3313–3326.

Sanderson, et al., "Preparation of 3-amino-2-pyrazinone-1 acetamide derivatives as thrombin inhibitors," *Chem. Abstracts* (The Amer. Chem. Soc.), vol. 128, No. 3, pp. 532–533, 22922r, Jan. 19, 1998.

* cited by examiner

*Primary Examiner*—Emily Bernhardt
(74) *Attorney, Agent, or Firm*—Richard S. Parr; Melvin Winokur; Valerie J. Camara

(57) ABSTRACT

Compounds of the invention are useful in inhibiting thrombin and associated thrombotic occlusions having the following structure:

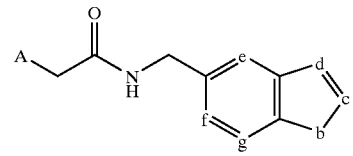

or a pharmaceutically acceptable salt thereof, wherein b is NY or O; c is $CY^2$ or N;

d is $CY^3$ or N; e is $CY^4$ or N; f is $CY^5$ or N; g is $CY^6$ or N; $Y^4$, $Y^5$, and $Y^6$ are independently hydrogen, $C_{1-4}$ alkyl, or halogen; $Y^1$ and $Y^2$ are independently hydrogen, $C_{1-4}$ alkyl, $C_{3-7}$ cycloalkyl, halogen, $NH_2$, OH or $C_{1-4}$ alkoxy, and $Y^3$ is hydrogen, $C_{1-4}$ alkyl, $C_{3-7}$ cycloalkyl, halogen, —CN, $NH_2$, OH or $C_{1-4}$ alkoxy;

A is

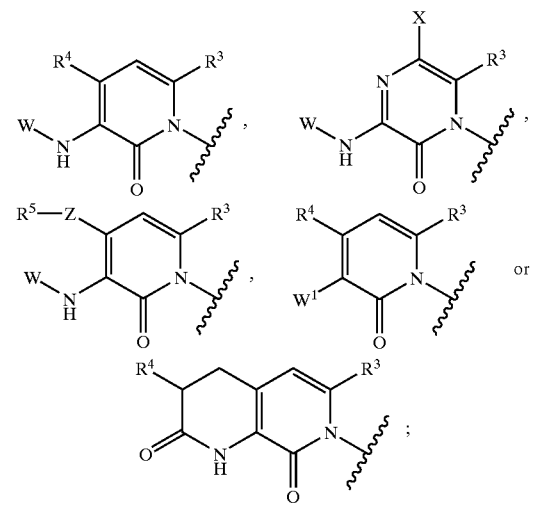

and W, $W^1$, $R^1$, $R^3$, $R^4$, $R^5$, X and Z are defined in the specification.

7 Claims, No Drawings

THROMBIN INHIBITORS

CROSS-REFERENCE TO RELATED APPLICATION

This application claims priority to provisional application No. 60/106,417, filed Oct. 30, 1998.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention, useful as thrombin inhibitors and having therapeutic value in for example, preventing coronary artery disease, have the following structure:

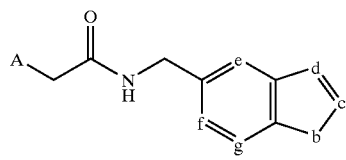

or a pharmaceutically acceptable salt thereof, wherein b is $NY^1$ or O; c is $CY^2$ or N;

d is $CY^3$ or N; e is $CY^4$ or N; f is $CY^5$ or N; g is $CY^6$ or N; $Y^4$, $Y^5$, and $Y^6$ are independently hydrogen, $C_{1-4}$ alkyl, or halogen; $Y^1$ and $Y^2$ are independently hydrogen, $C_{1-4}$ alkyl, $C_{3-7}$ alcycloalkyl, halogen, $NH_2$, OH or $C_{1-4}$ alkoxy, and $Y^3$ is hydrogen, $C_{1-4}$ alkyl, $C_{3-7}$ alcycloalkyl, halogen, —CN, $NH_2$, OH or $C_{1-4}$ alkoxy;

A is

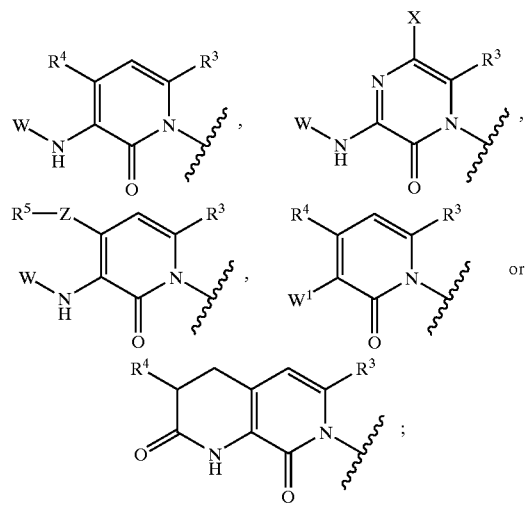

W is
  hydrogen,
  $R^1$,
  $R^1OCO$,
  $R^1CO$,
  $R^1SO_2$,
  $R^1CH_2)_nNHCO$, or
  $(R^1)_2CH(CH_2)_nNHCO$,
    wherein n is 0–4;

$W^1$ is
  hydrogen, OH, $CH_3CO$, or $R^2CH_2SO_2CH_2$;

$R^1$ is $R^2$, $R^2(CH_2)_mC(R^8)_2$, where m is 0–3, and each $R^8$ can be the same or different, $(R^2)(OR^2)CH(CH_2)_p$, where p is 1–4,

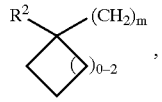

where m is 0–3;

$R^2C(R^8)_2(CH_2)_m$, wherein m is 0–3, and each $R^8$ can be the same or different, wherein $(R^8)_2$ can also form a ring with C represented by $C_{3-7}$ alcycloalkyl, $R^2CH_2C(R^8)_2(CH_2)_q$, wherein q is 0–2, and each $R^8$ can be the same or different, wherein $(R^8)_2$ can also form a ring with C represented by $C_{3-7}$ alcycloalkyl, $(R^2)_2CH(CH_2)r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S, $R^2O(CH_2)p$, wherein p is 1–4, $R^2CF_2C(R^8)_2$, $(R^2CH_2)_2CH$, where $R^2$ can be the same or different, $R^2SO_2$, $R^2CH_2SO_2$, $R^2CH_2O(CH_2)_p$, wherein p is 1–4, $(R^2(CH_2)_q)_2N(CH_2)_p$, wherein q is 1 or 2 and p is 1–4, $R^2(COOR^6)(R^8)C(CH_2)_r$, wherein r is 1–4

$R^2NR^{11}(CH_2)_p$, where $R^{11}$ is hydrogen or $CH_3$ and p is 0, 1 or 2,

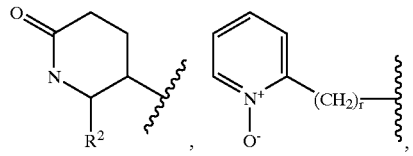

wherein r is 1–4, $R^2(COOR^6)(CH_2)_r$, where r is 1–4;

$R^2$ and $R^5$ are independently hydrogen, phenyl, unsubstituted or substituted with one or more of $C_{1-4}$ alkyl, $C_{1-4}$ alkoxy, halogen, hydroxy, COOH, $CONH_2$, $CH_2OH$, $CO_2R^7$, where $R^7$ is $C_{1-4}$ alkyl, or $SO_2NH_2$, naphthyl, biphenyl, a 5- to 7- membered heterocyclic saturated or unsaturated ring, or a 9- to 10-membered bicyclic fused ring system, wherein the rings are independently heterocyclic or non-heterocyclic and saturated or unsaturated, wherein the heterocyclic ring contains from one to four heteroatoms selected from the group consisting of N, O and S, and wherein the heterocyclic or non-heterocyclic ring is unsubstituted or substituted with halogen, hydroxy, $C_{1-4}$ alkyl, $C_{3-7}$ alcycloalkyl,

—CN,

—$CON(R^7)_2$, wherein $R^7$, same or different, is hydrogen, unsubstituted $C_{1-4}$ alkyl, or $C_{1-4}$kyl substituted with —OH, —$OCH_2R^7$, wherein $R^7$ is $C_{3-7}$ cycloalkyl or COOH,

—$SCH_3$,

—$COR^7$, wherein $R^7$ is $C_{1-4}$ alkyl or amino, phenyl, unsubstituted or substituted with halogen,

—$SO_2CH_3$,

—$OCH_2CONR^7$, wherein $R^7$ is $C_{3-7}$ cycloalkyl,

—$CH_2R^7$, wherein $R^7$ is $C_{3-7}$ cycloalkyl or phenyl, $C_{1-7}$ alkyl, unsubstituted or substituted with one or more of hydroxy,

COOH, amino, aryl, $C_{3-7}$ alcycloalkyl, $CF_3$, $N(CH_3)_2$,

—$C_{1-3}$alkylaryl, heteroaryl, or heterocycloalkyl, $CF_3$, $C_{3-7}$ alcycloalkyl, unsubstituted or substituted with aryl or —$OCH_2R^7$ wherein $R^7$ is $C_{3-7}$ cycloalkyl $C_{7-12}$ bicyclic alkyl, or $C_{10-16}$ tricyclic alkyl;

$R^3$, $R^4$ and $R^6$ are independently selected from the group consisting of hydrogen, $C_{1-4}$ alkyl, $C_{3-7}$ cycloalkyl, halogen, phenyl, unsubstituted or substituted with halogen, $CF_3$ or $C_{1-5}$ alkyl, $R^{12}CO$, where $R^{12}$ is hydrogen, $C_{1-5}$ alkyl, pyrrolidine unsubstituted, monosubstituted or independently disubstituted with $C_{1-4}$ alkyl, piperidine unsubstituted, monosubstituted or independently disubstituted with $C_{1-4}$ alkyl, or azepine unsubstituted, monosubstituted or independently disubstituted with $C_{1-4}$ alkyl;

a 5–7 membered heterocyclic saturated or unsaturated ring wherein the ring contains one to four heteroatoms selected from the group consisting of N, O and S, and wherein the ring is unsubstituted or substituted with phenyl, $COCH_3$, unsubstituted $C_{1-4}$ alkyl, or $C_{1-4}$ alkyl substituted with —OH or phenyl,

—CN,

—$SCH_3$,

—$SOCH_3$,

—$SO_2CH_2$, $R^{10}$ where $R^{10}$ is hydrogen or $C_{3-7}$ alcycloalkyl, or trifluoromethyl;

X is hydrogen, or halogen;

Z is $CH_2$, S, or $SO_2$;

$R^8$ is hydrogen, phenyl, unsubstituted or substituted with one or more of $C_{1-4}$ alkyl, $C_{1-4}$ alkoxy, halogen, hydroxy, COOH, $CONH_2$, halogen,
naphthyl,
biphenyl,
a 5- to 7- membered mono- or a 9- to 10-membered bicyclic heterocyclic ring which can be saturated or unsaturated, and which contains from one to four heteroatoms selected from the group consisting of N, O and S,
$C_{1-4}$ alkyl, unsubstituted or substituted with one or more of
hydroxy,
COOH,
$NHCH_3$,
amino,
aryl,
heteroaryl, or
heterocycloalkyl,
$CF_3$,
$C_{3-7}$ alcycloalkyl,
$C_{7-12}$ bicyclic alkyl, or
$C_{10-16}$ tricyclic alkyl.

A class of compounds of the invention, or a pharmaceutically acceptable salt thereof, includes those wherein A is

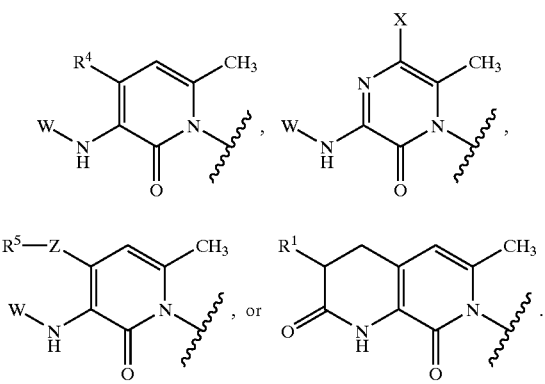

A subclass of compounds of this class, or a pharmaceutically able salt thereof, includes those wherein
$Y^1$, $Y^2$, $Y^3$, $Y^4$, $Y^5$, and $Y^6$ are independently hydrogen, $C_{1-4}$ alkyl, $N_2$ or Cl; W is hydrogen or $R^1$;
$R^1$ is $R^2$,
$R^2SO_2$,
$R^2CH_2SO_2$, or

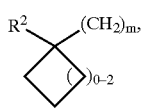

where m is 0–3;
$R^2$ and $R^5$ are independently selected from the group consisting of hydrogen, $C_{1-7}$ alkyl unsubstituted or substituted with aryl, $C_{3-7}$ cycloalkyl, or heteroaryl; and $R^3$ and $R^4$ are independently selected from the group consisting of hydrogen and $C_{1-4}$ alkyl; and Z is $SO_2$.

In a group of compounds of this subclass, or a pharmaceutically acceptable salt thereof, $Y^1$, $Y^2$, $Y^3$, $Y^4$, $Y^5$, and $Y^6$ are independently hydrogen, methyl, $NH_2$ or Cl; W is hydrogen or

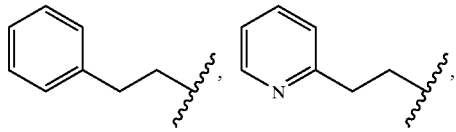

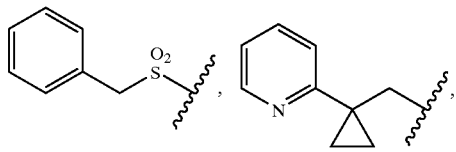

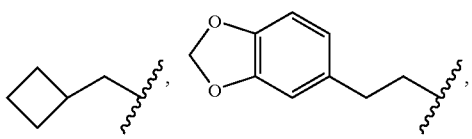

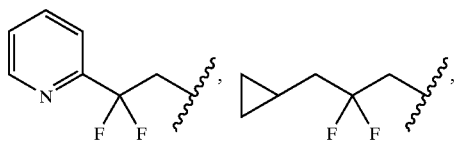

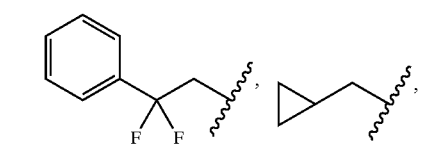

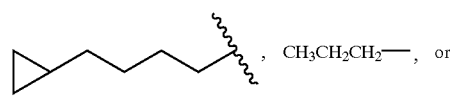

$R^5$ is

$R^3$ and $R^4$ are independently selected from the group consisting of hydrogen and methyl.

In a subgroup of this group of compounds, b is NH, $N(CH_3)$ or O, c is CH, $C(CH_3)$ or N, d is CH, N, $C(NH_2)$, $C(Cl)$, or $C(CH_3)$, e is CH, N or $C(CH_3)$, f is CH, $C(CH_3)$, or N, and g is CH or N.

Examples of this group are listed below in Table 1. Inhibitory activity of compounds of the invention is represented by "***", indicating Ki greater than or equal to 20 nM, or "*", indicating Ki less than 20 nM. Values are as determined according to the in vitro assay described later in the specification.

TABLE 1
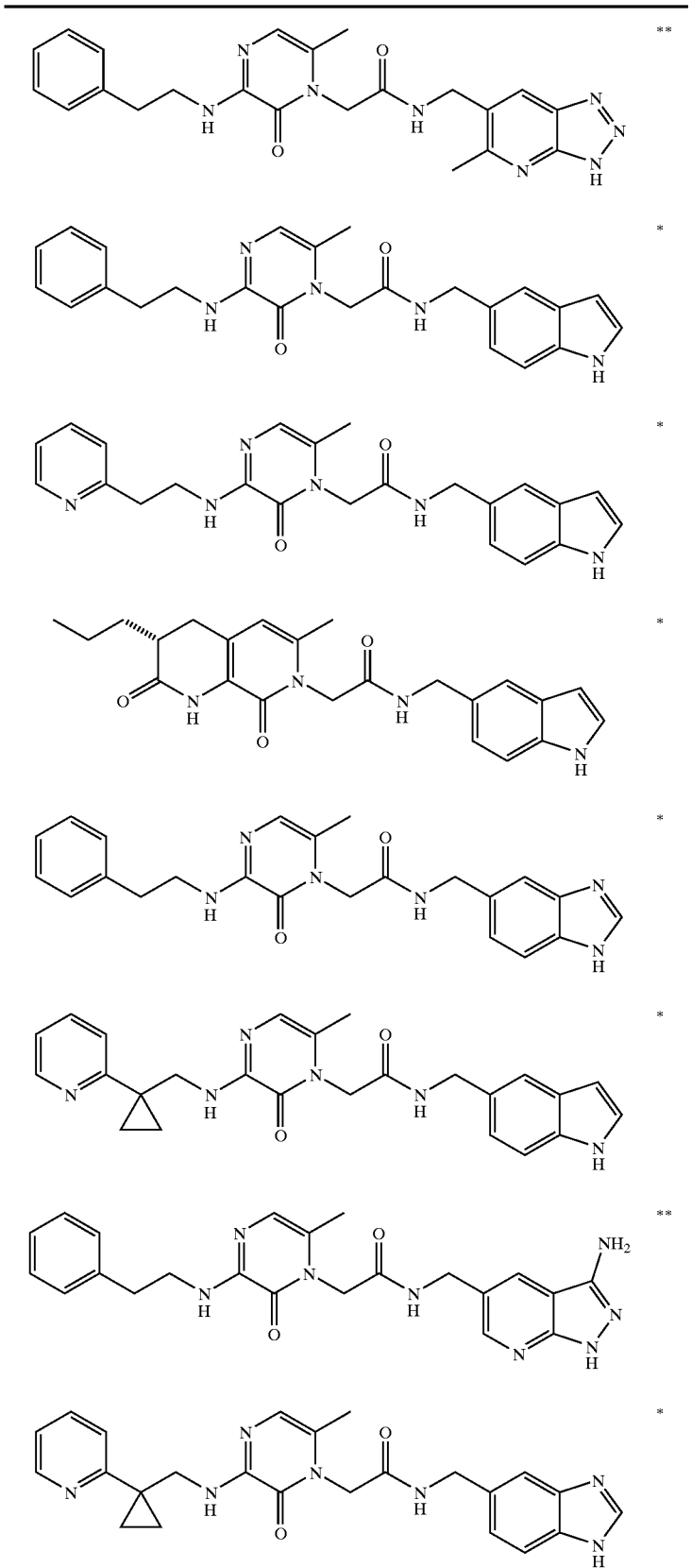

TABLE 1-continued
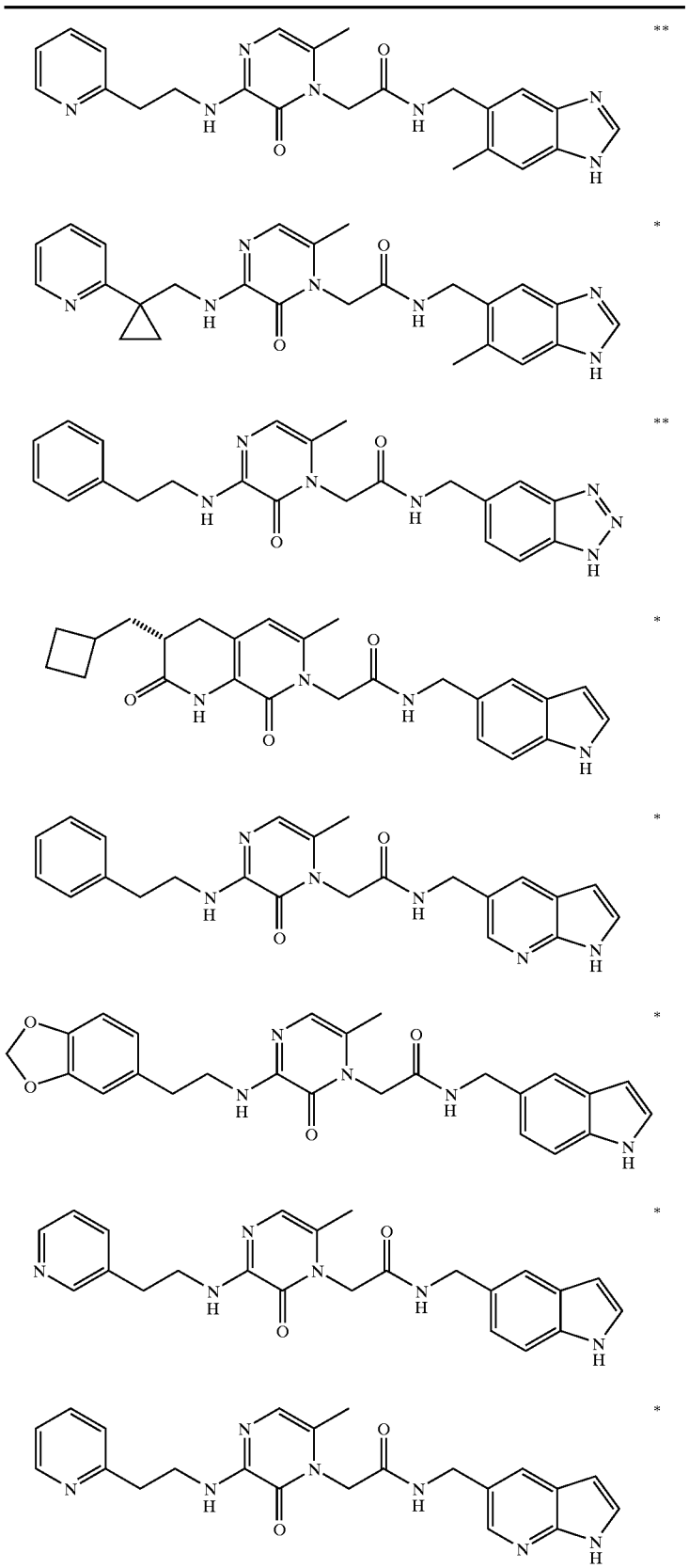

TABLE 1-continued
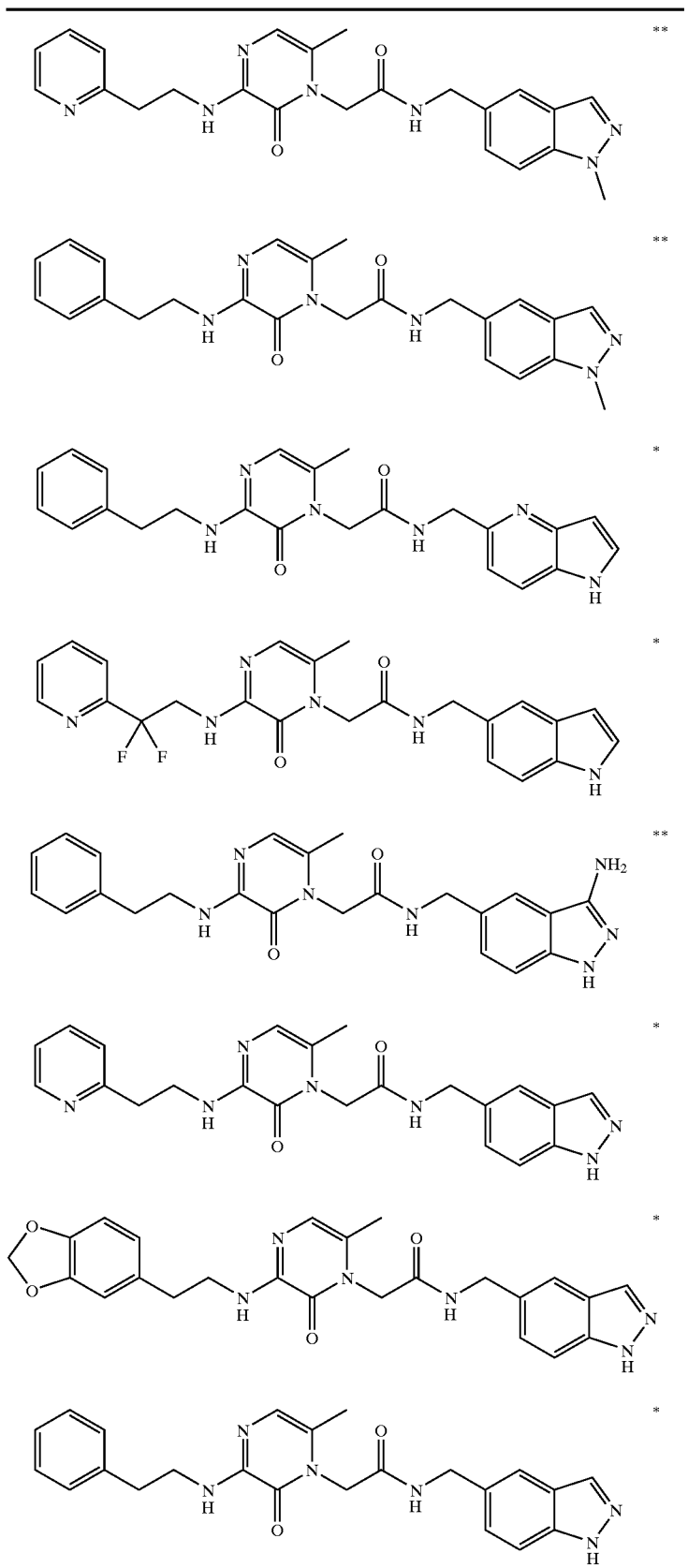

TABLE 1-continued
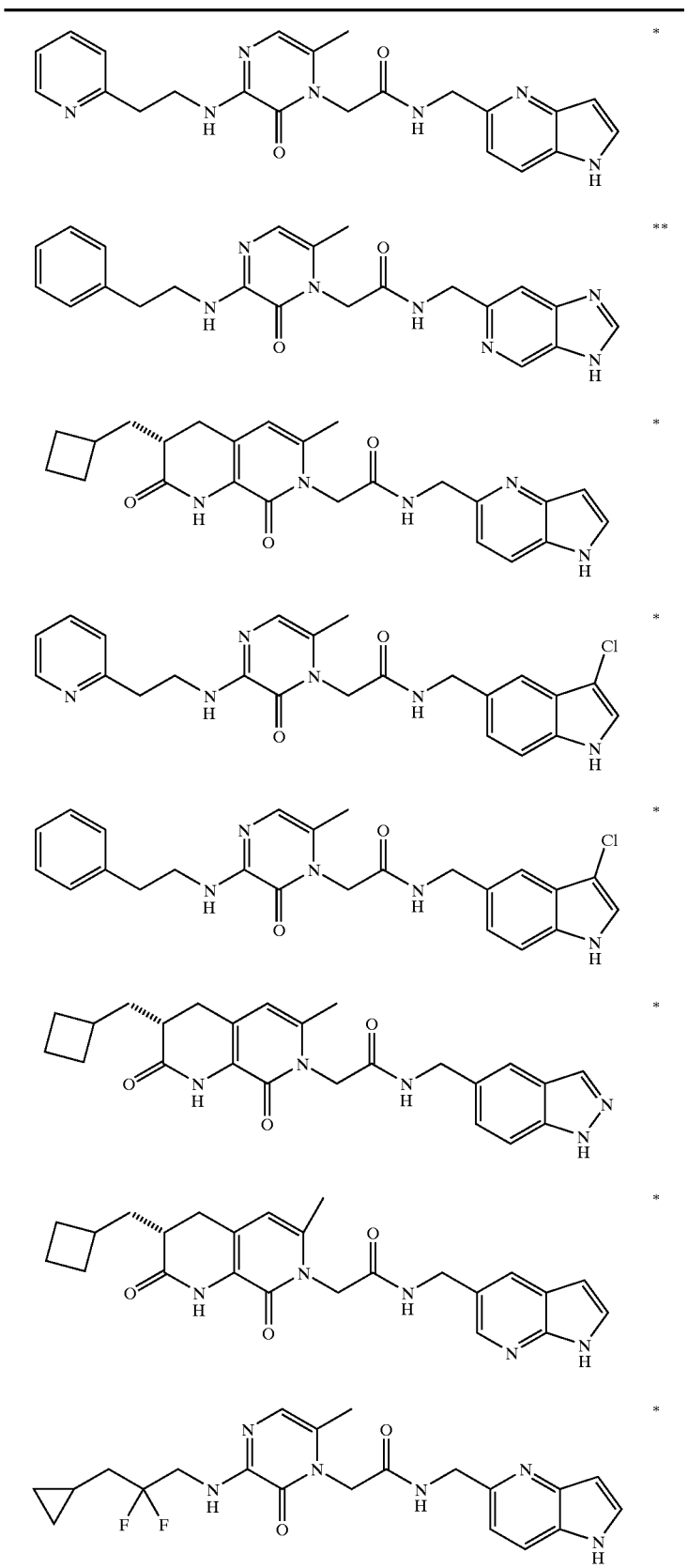

TABLE 1-continued
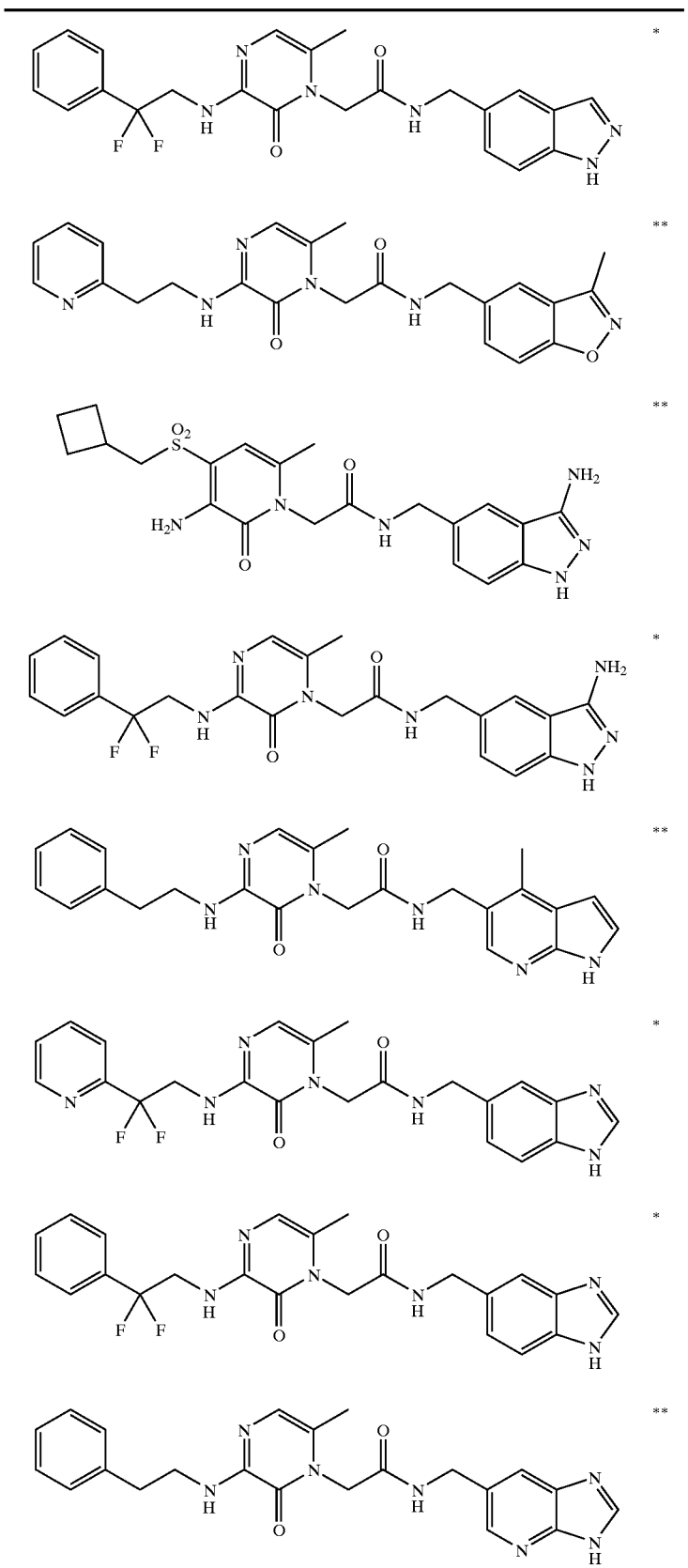

TABLE 1-continued
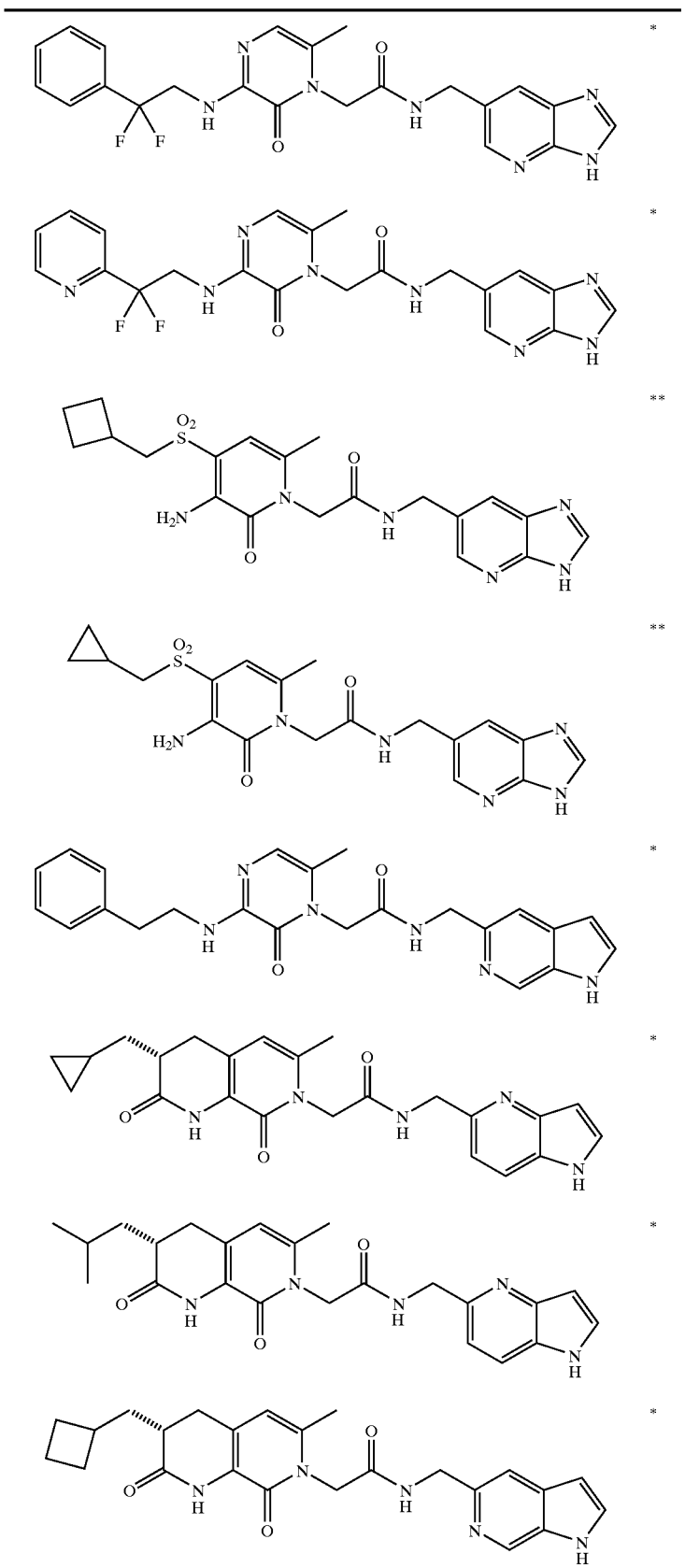

TABLE 1-continued
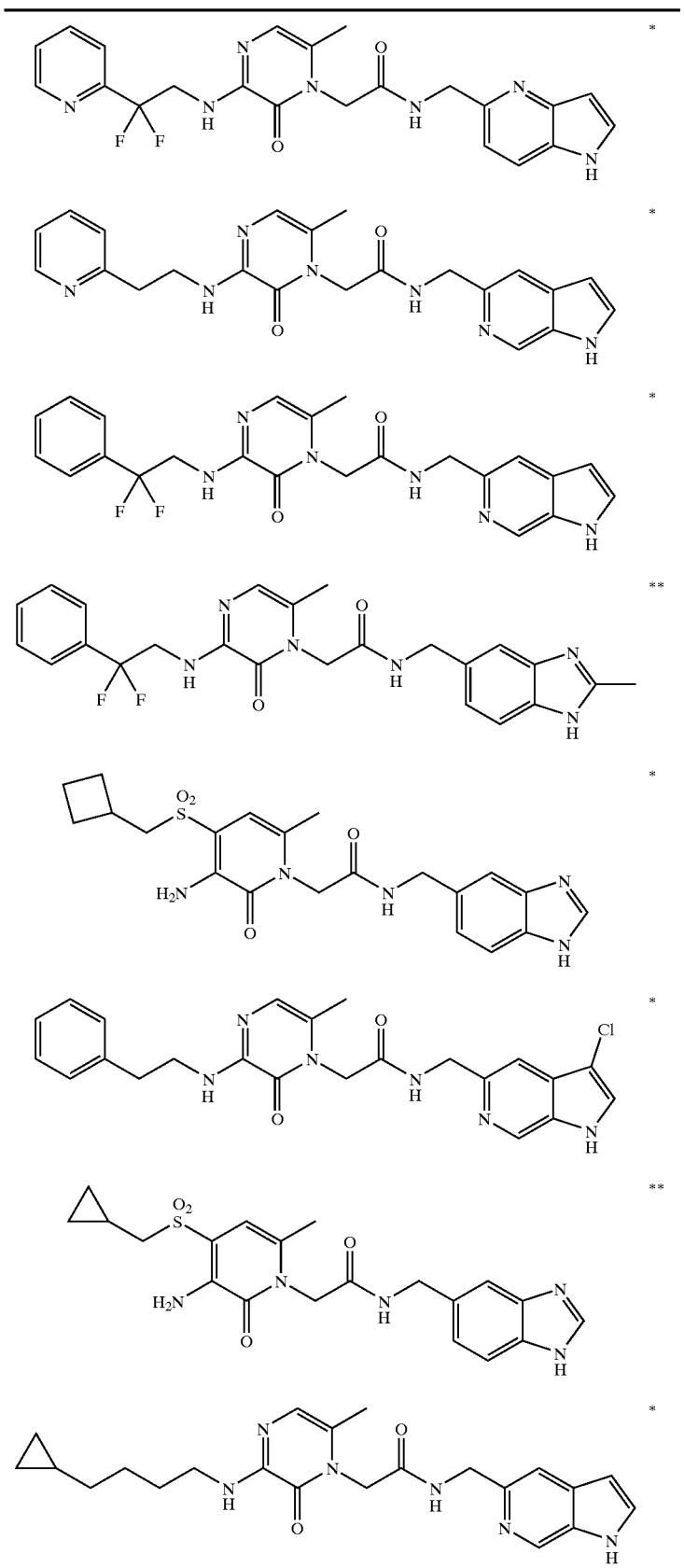

TABLE 1-continued
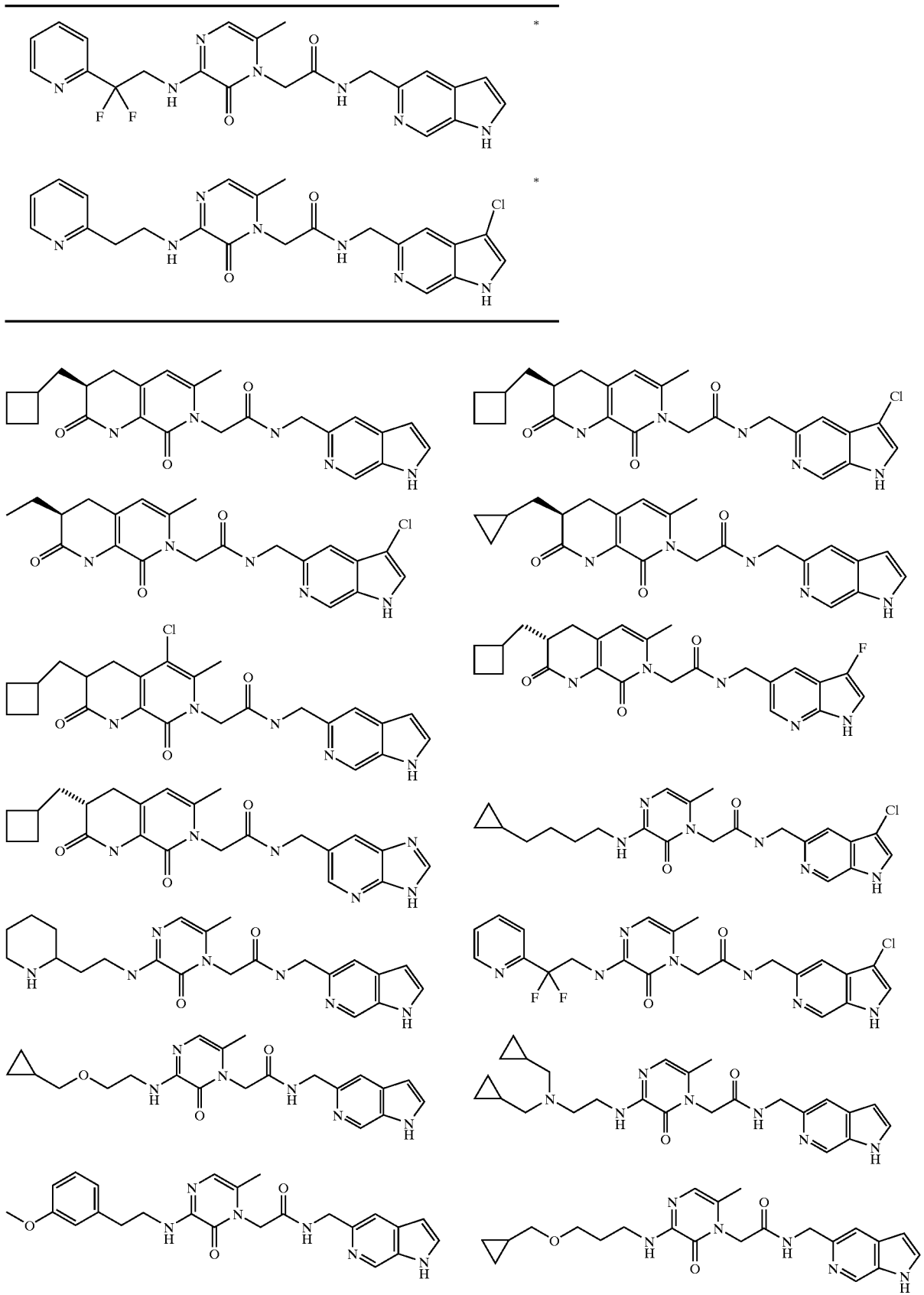

-continued
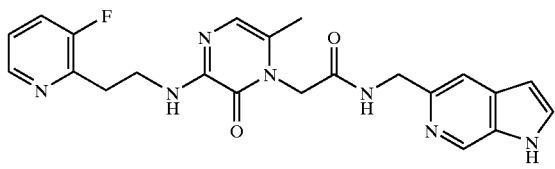
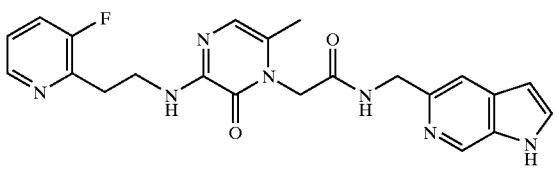
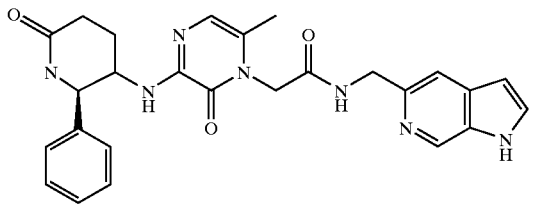
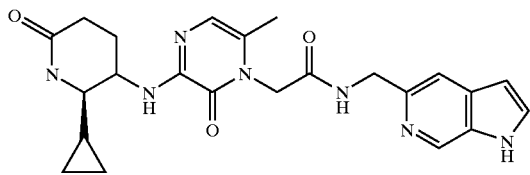
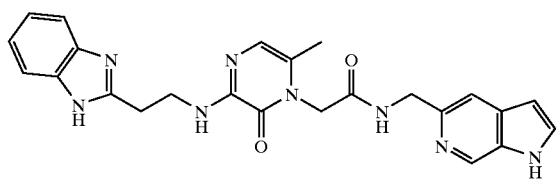
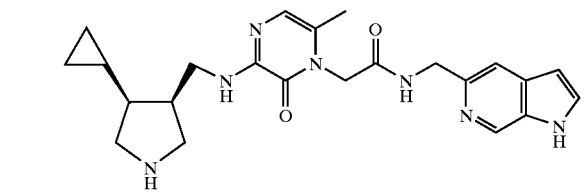
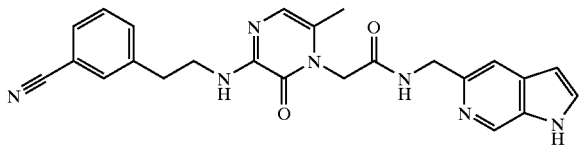
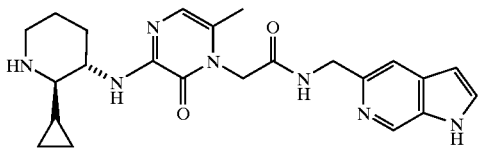
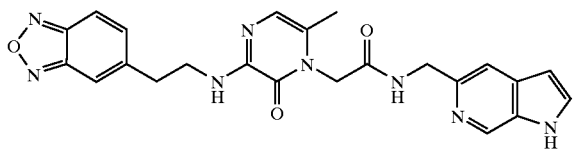
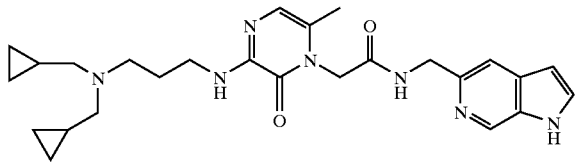
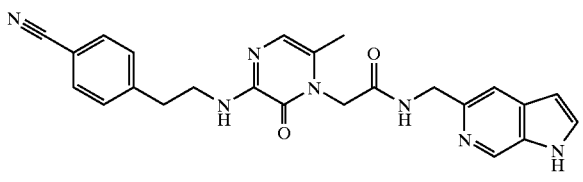
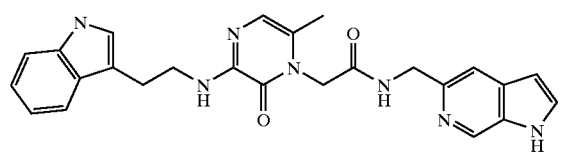
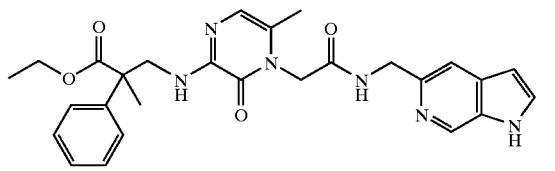
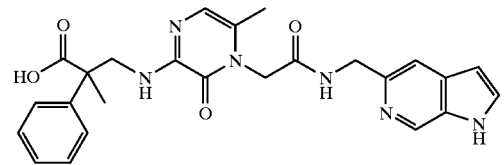
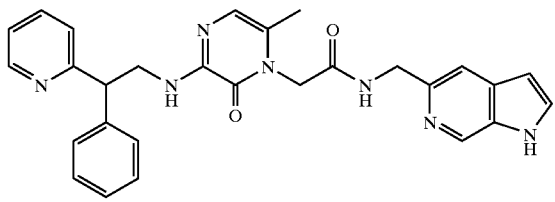
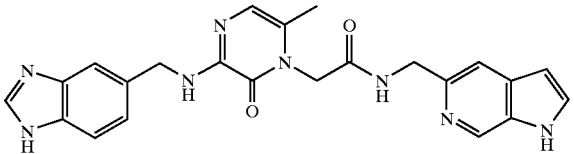

-continued
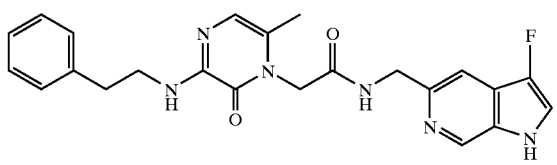
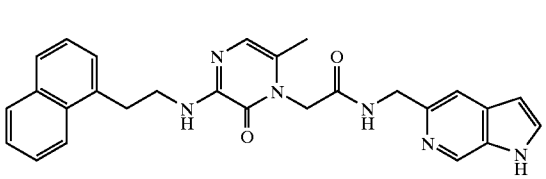
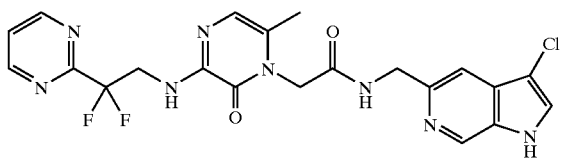
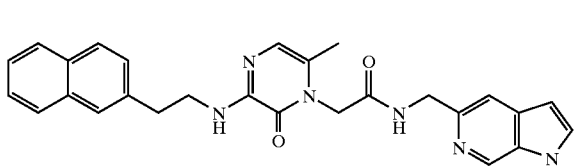
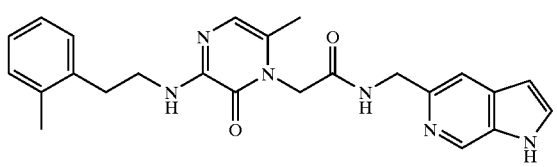
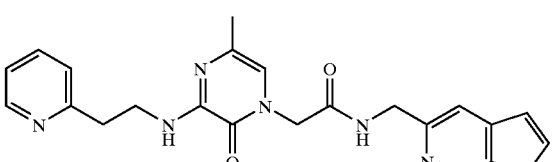
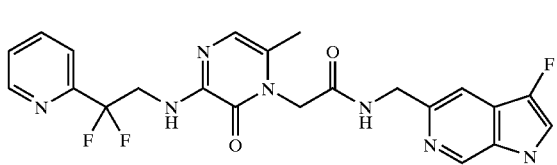
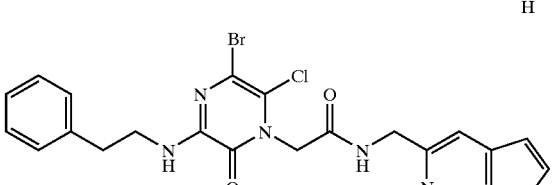
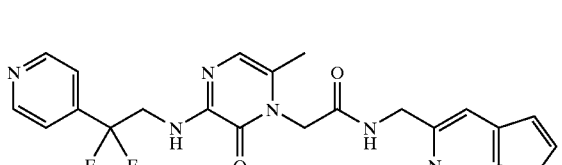
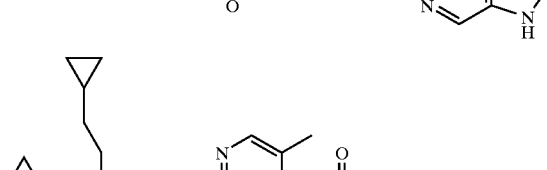
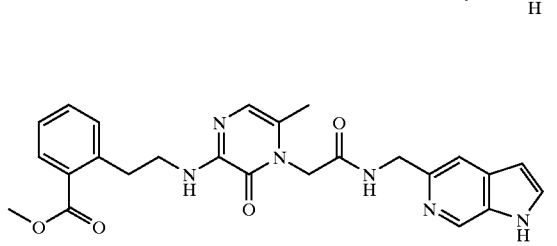
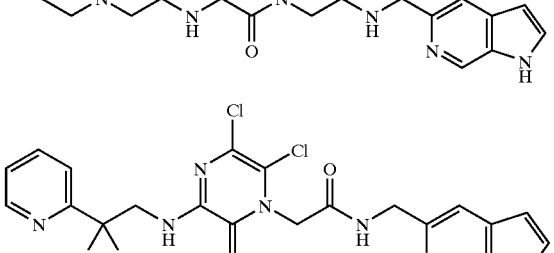
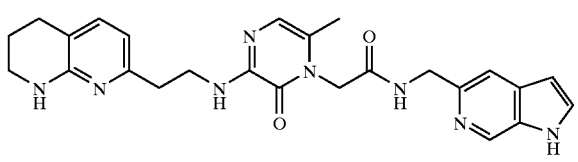
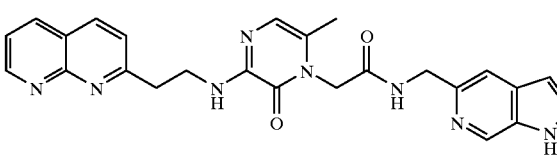
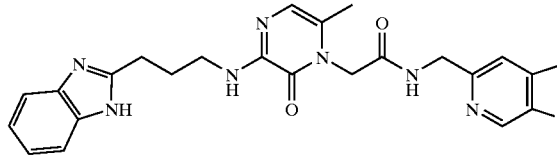
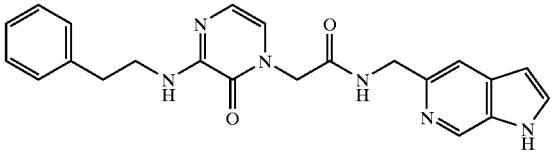
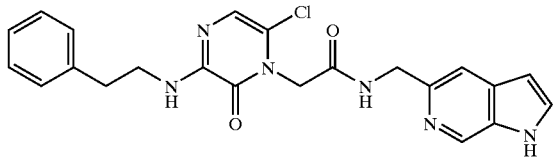
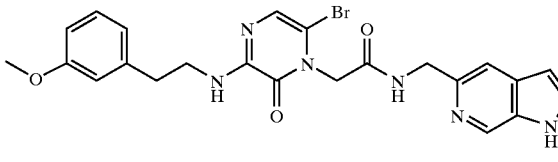

-continued
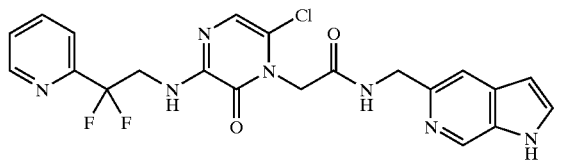
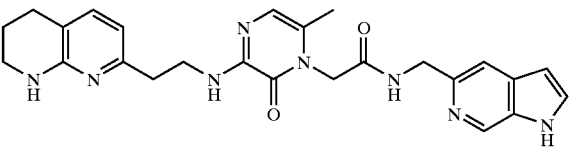
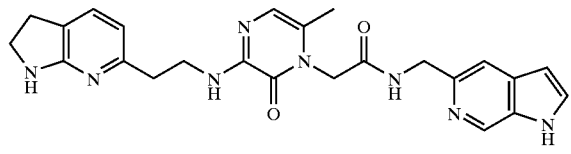
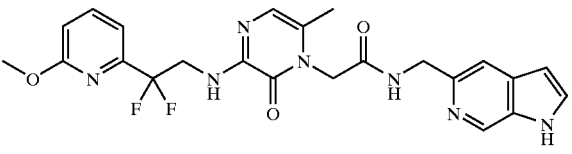
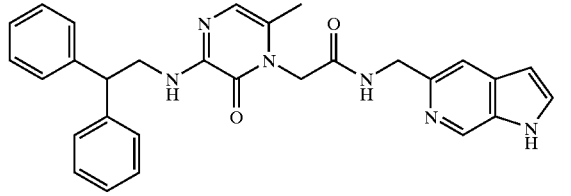
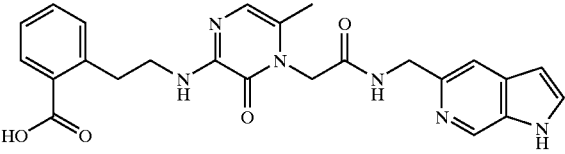
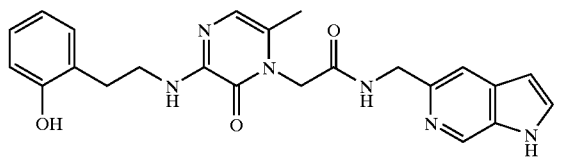
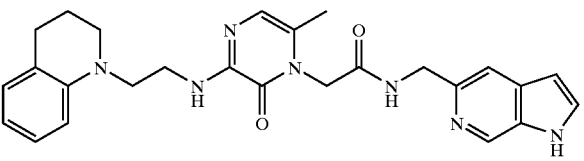
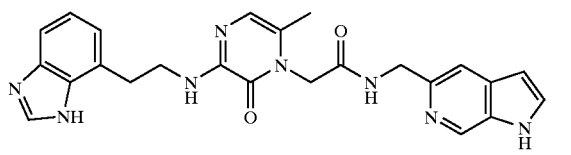
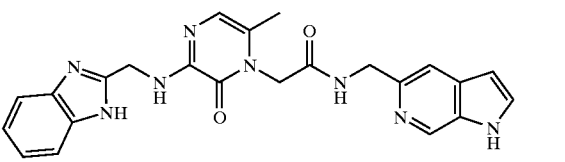
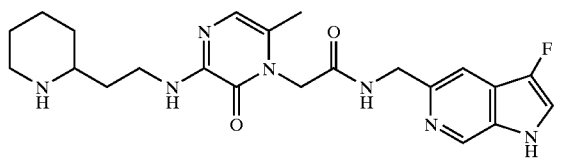
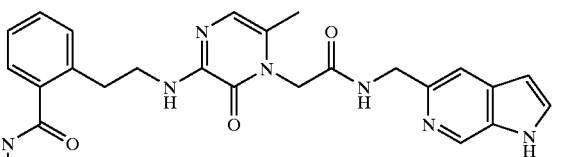
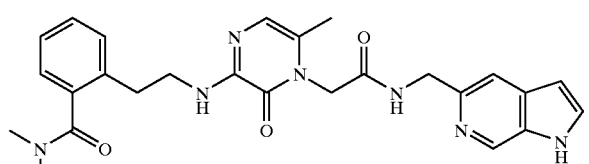
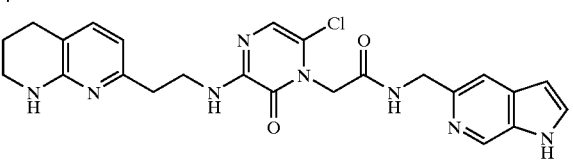
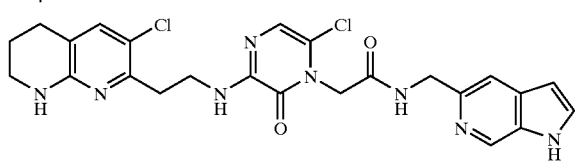
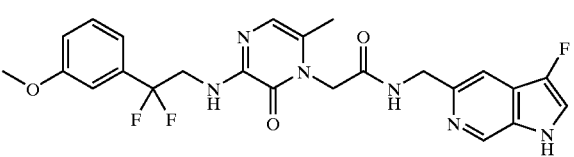
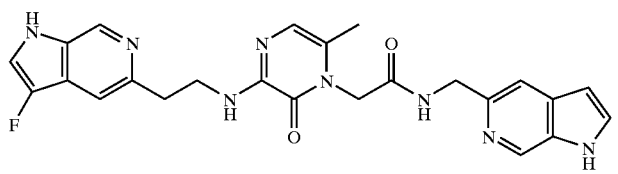
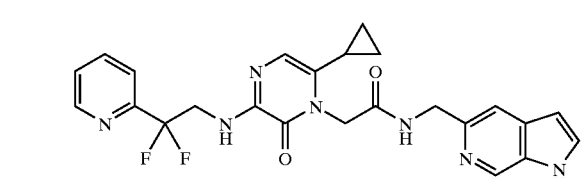
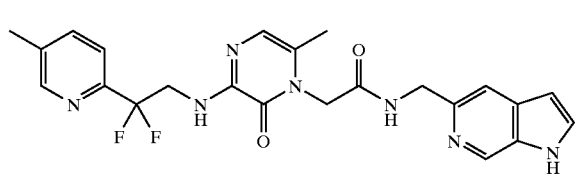
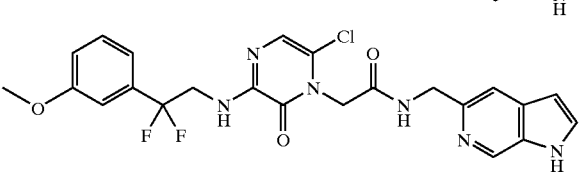

-continued
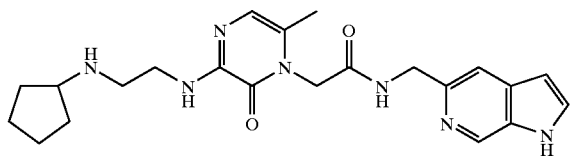
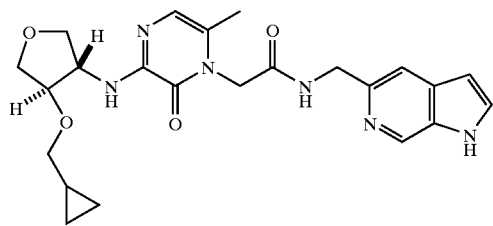
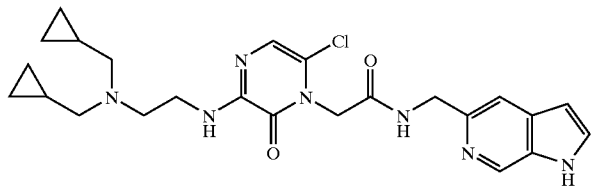
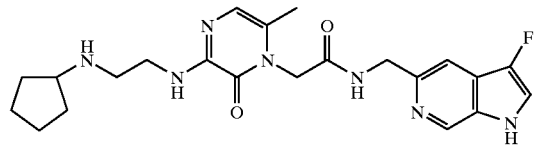
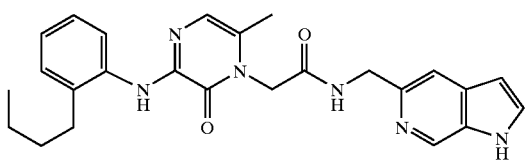
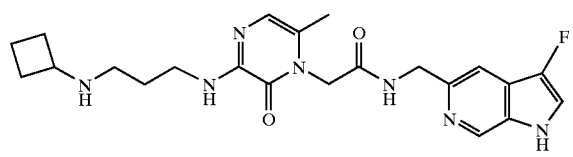
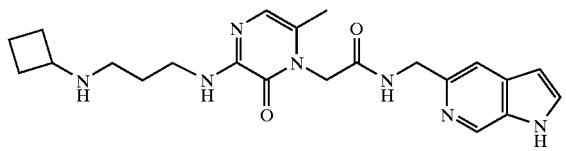
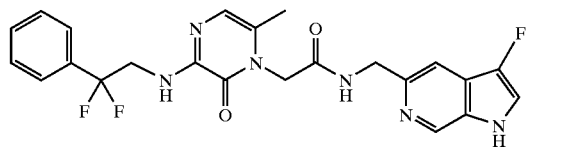
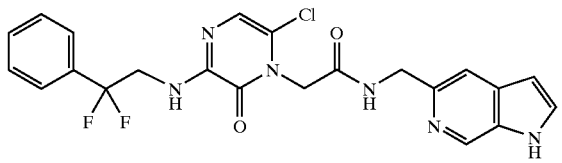
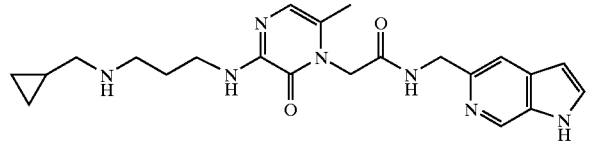
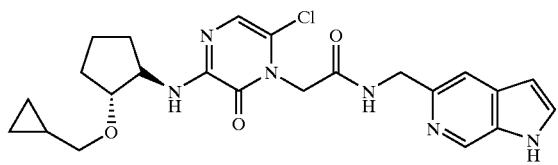
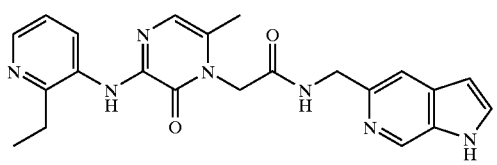
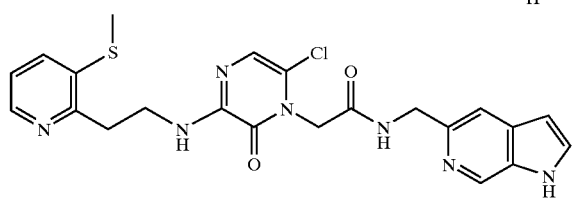
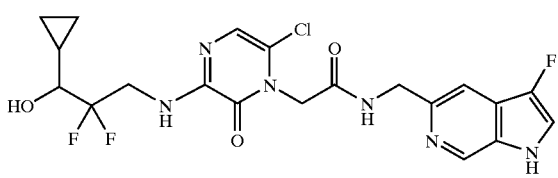
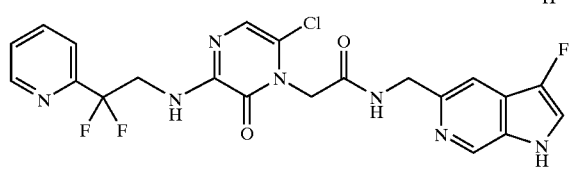
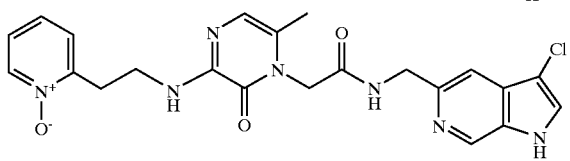
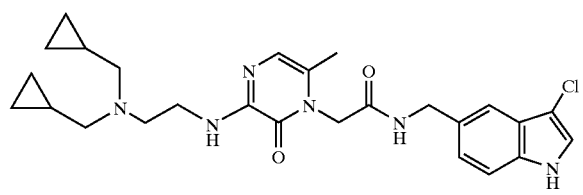

-continued
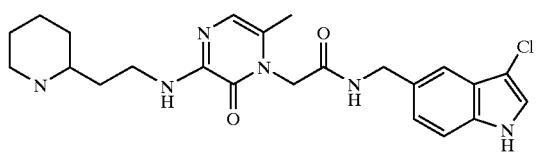
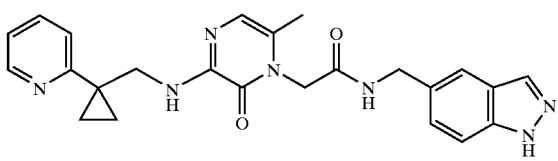
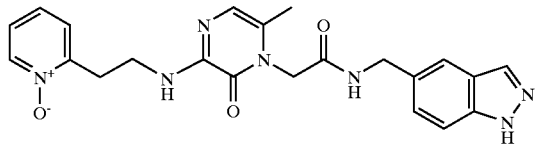
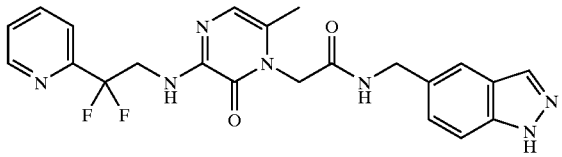
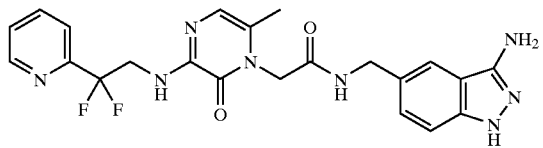
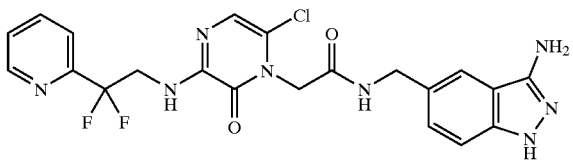
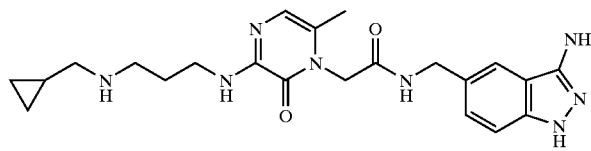
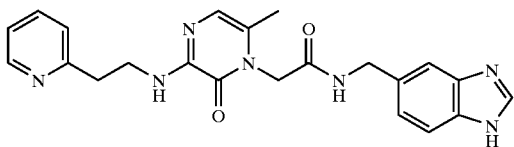
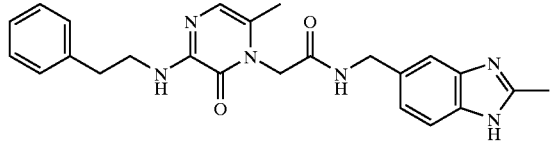
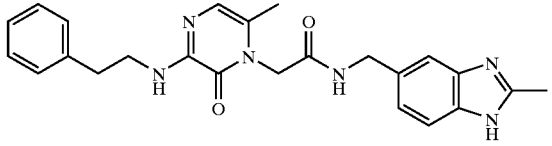
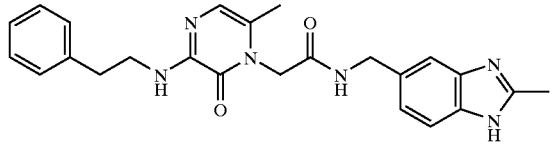
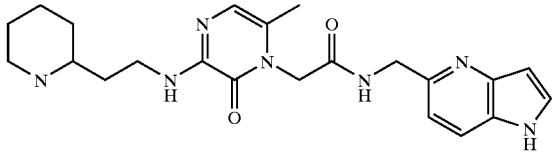
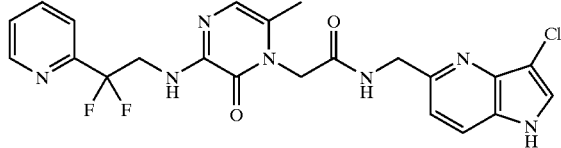
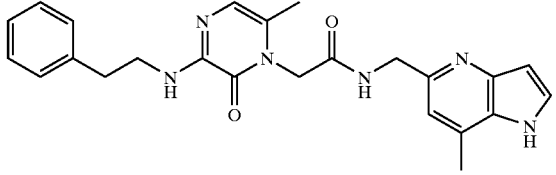
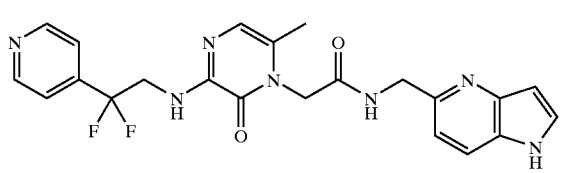
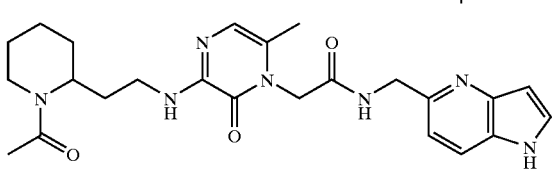
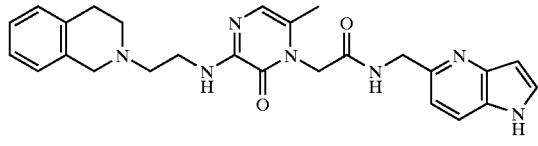
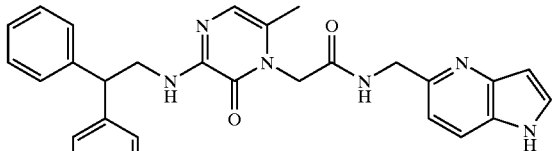
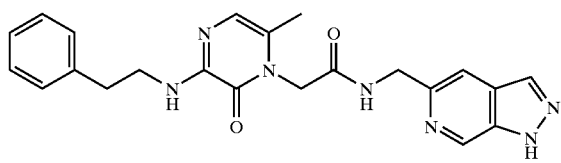
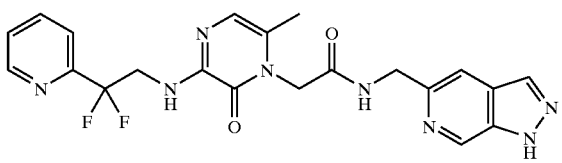

-continued
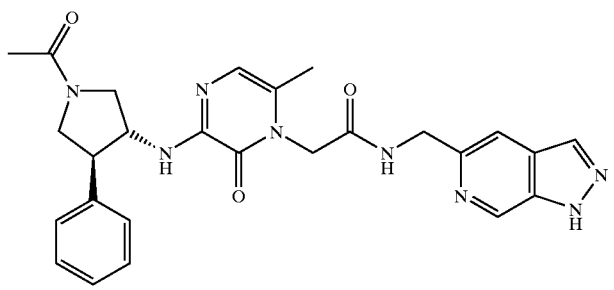
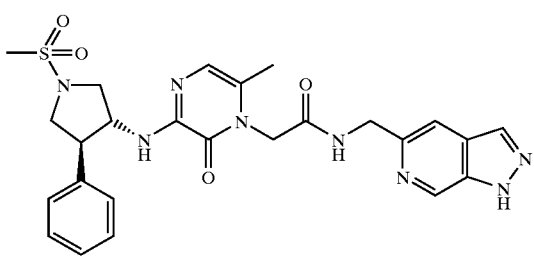
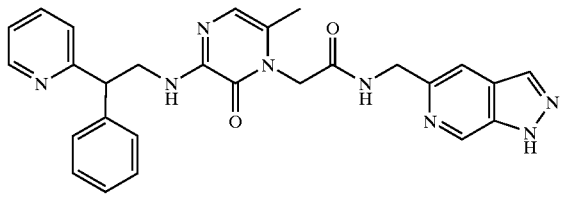
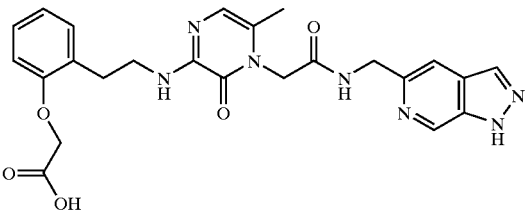
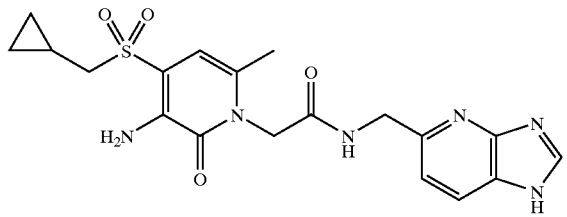
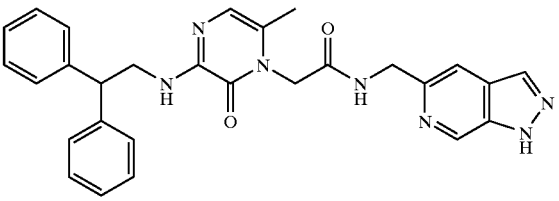
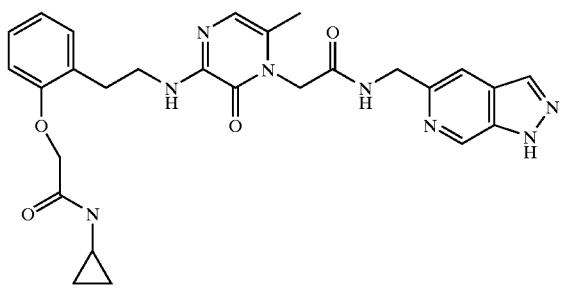
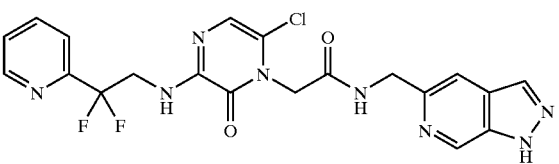
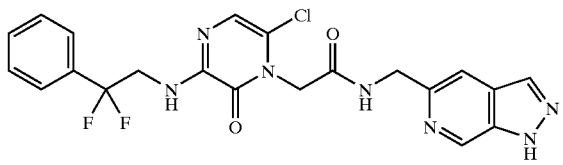
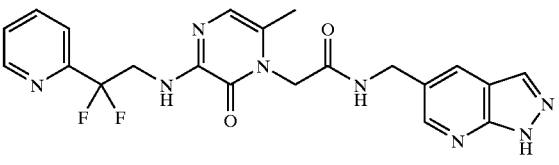
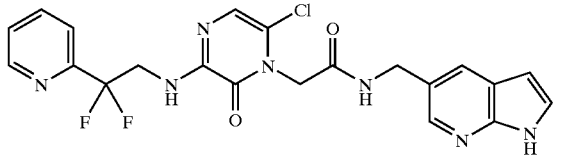
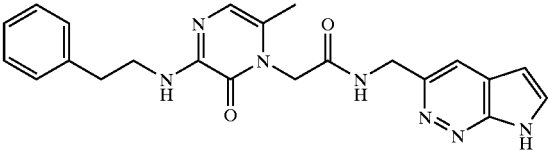
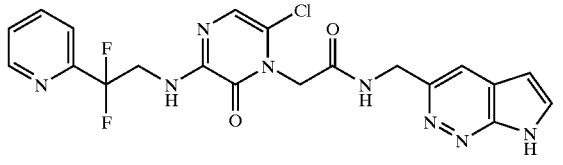
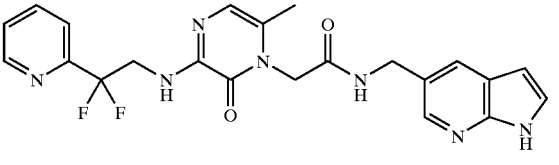
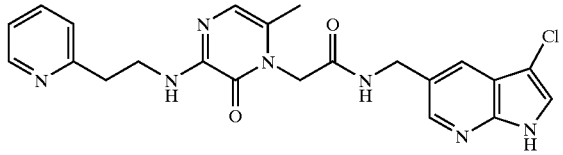
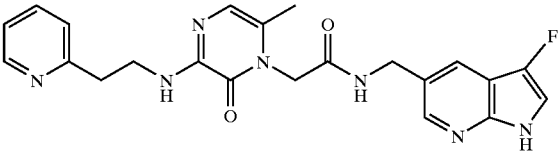

-continued
| 35 | 36 |
|---|---|
| 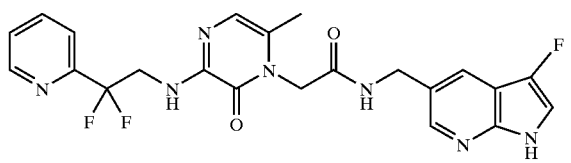 |  |
| 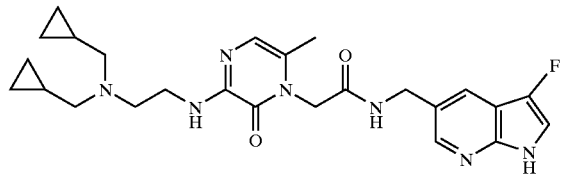 | 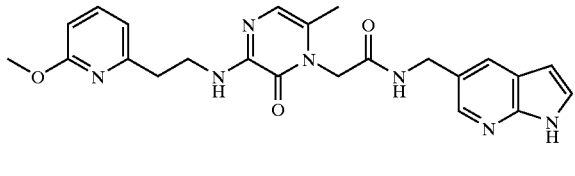 |
| 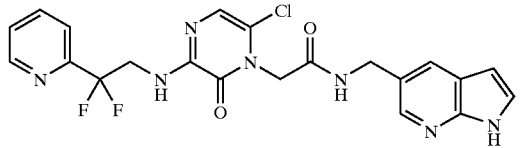 | 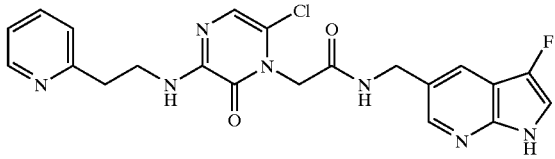 |
| 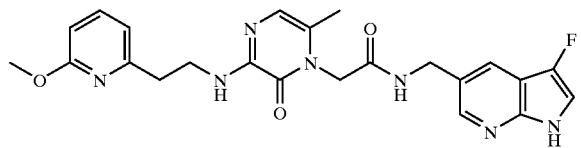 | 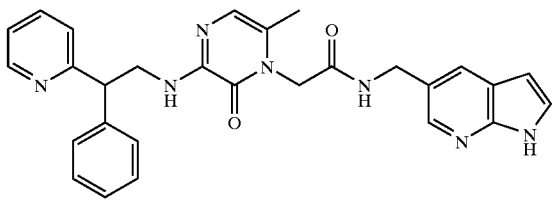 |
| 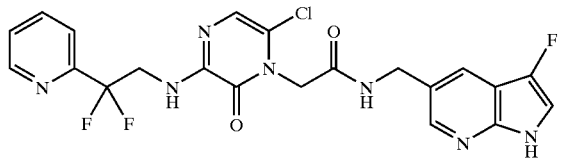 | 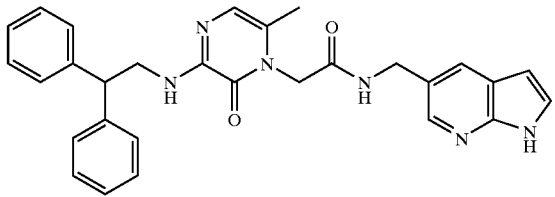 |
| 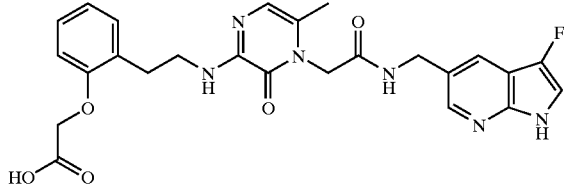 | 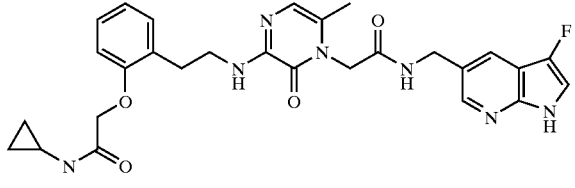 |
| 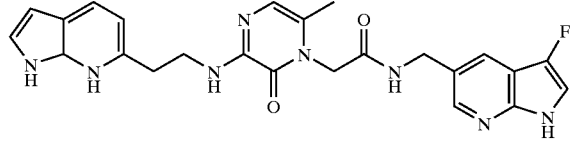 | 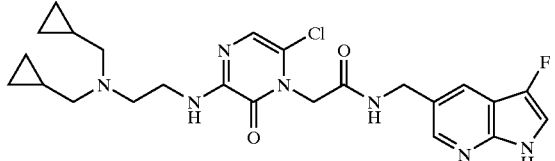 |
| 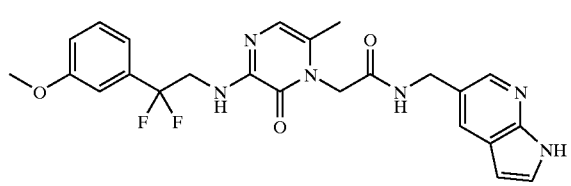 | 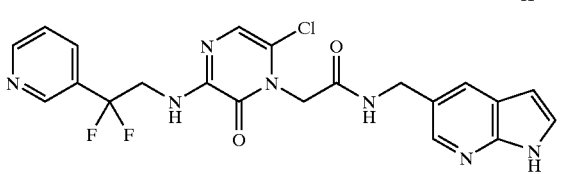 |
| 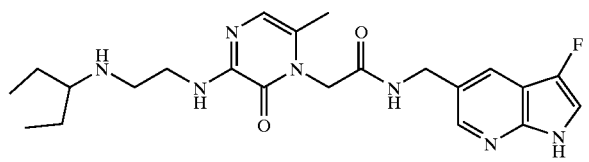 | 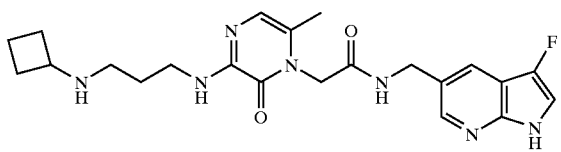 |

37
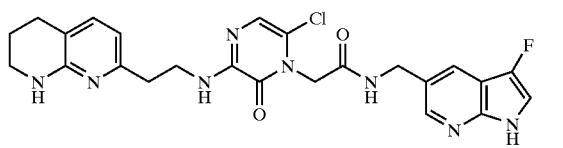
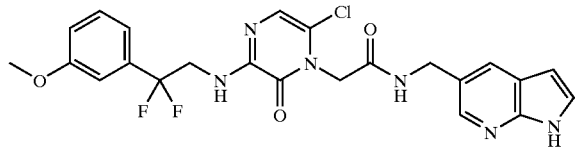
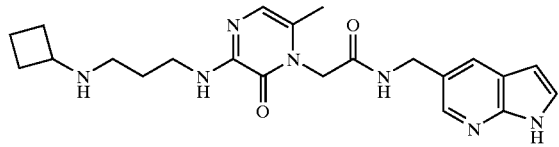
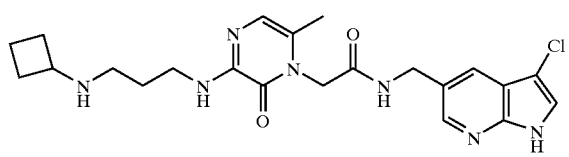
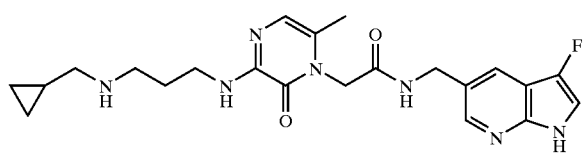
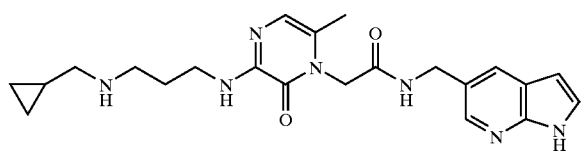
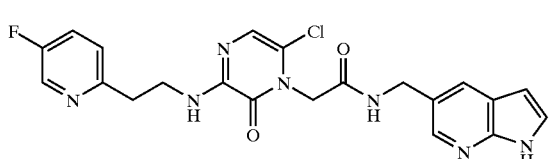
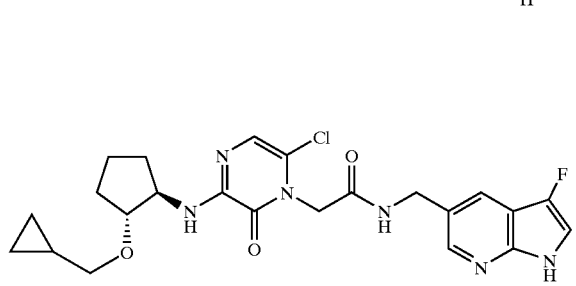
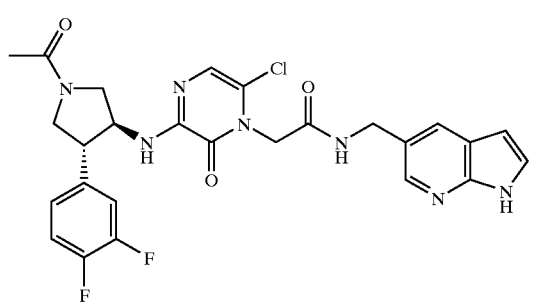
38
-continued
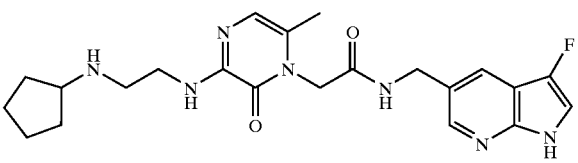
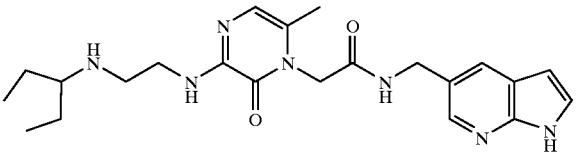
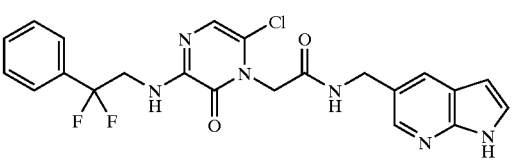
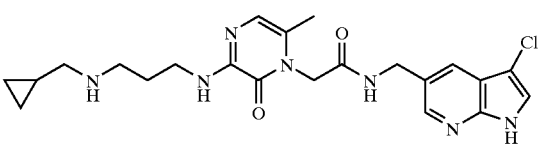
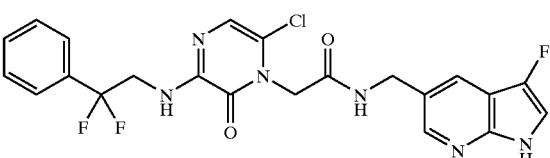
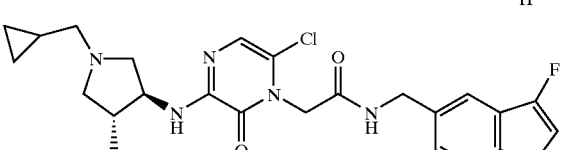
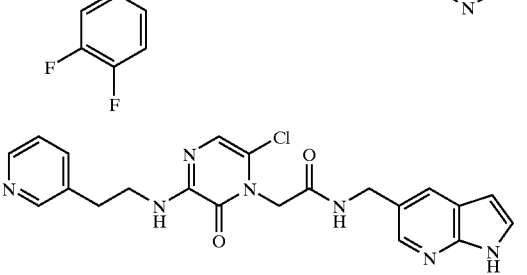
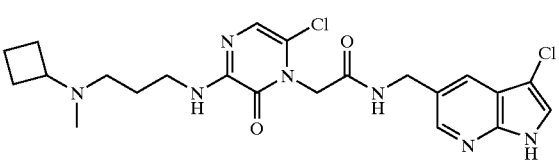

-continued
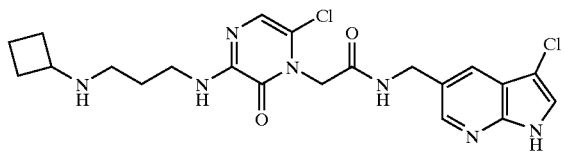
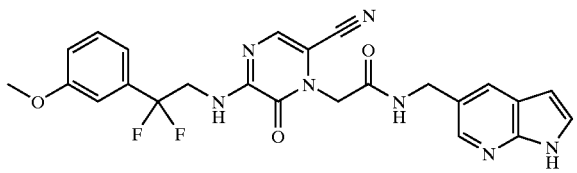
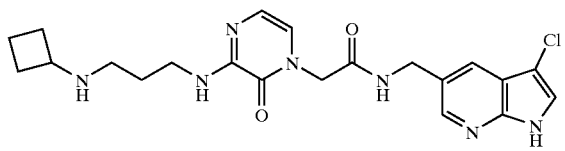
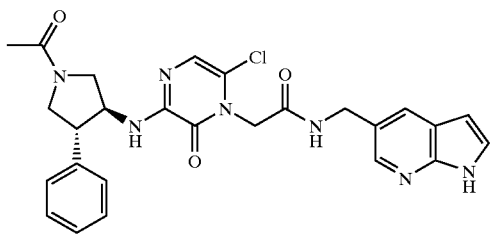
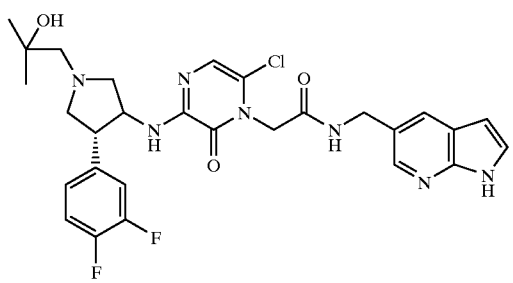
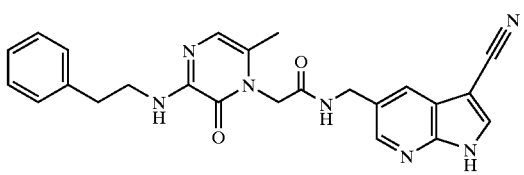
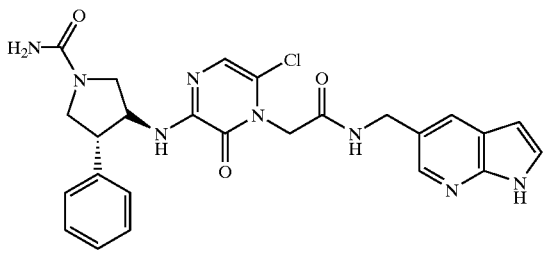
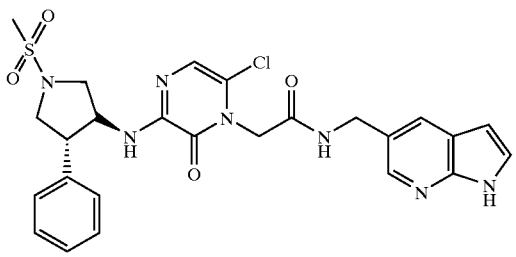
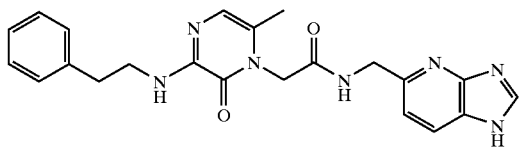
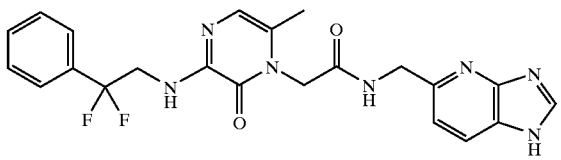
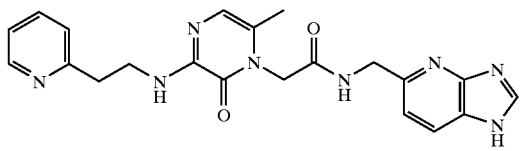
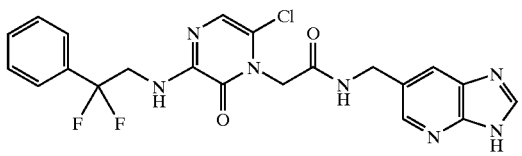
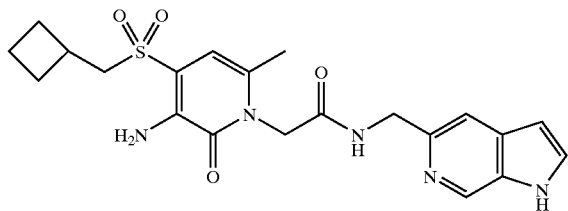
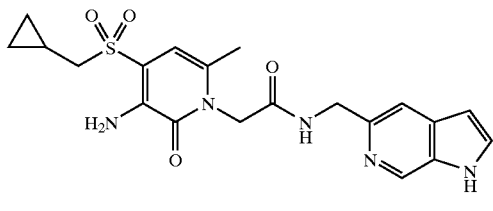

-continued
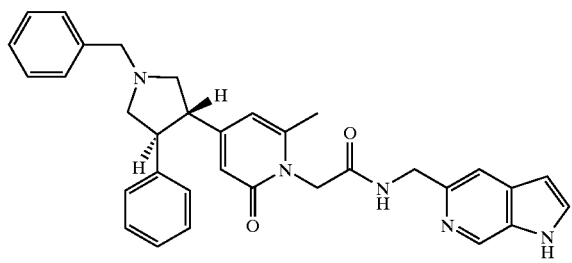
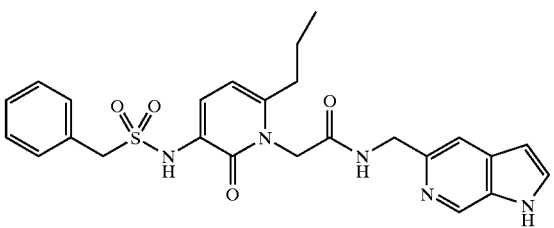
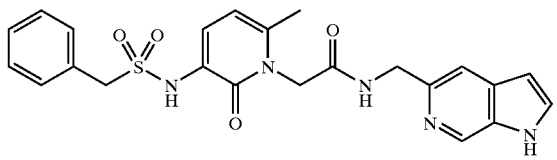
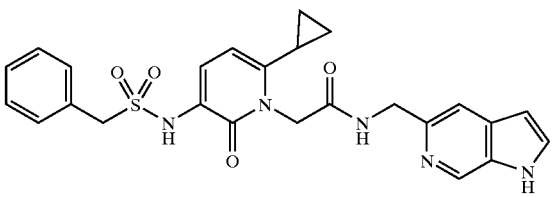
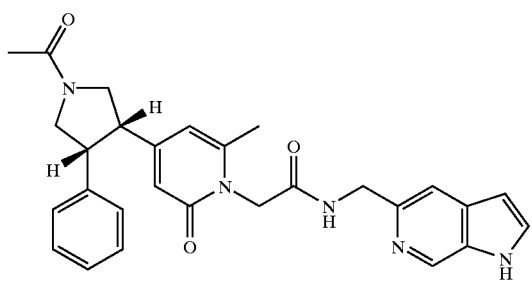
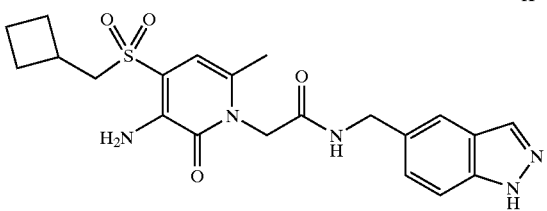
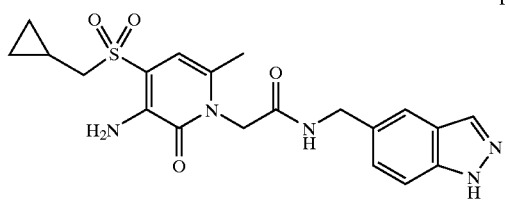
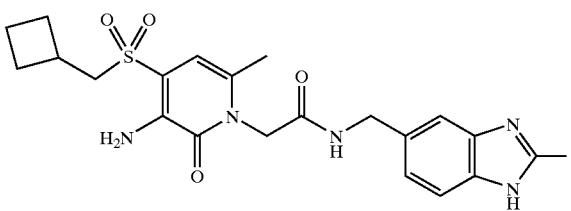
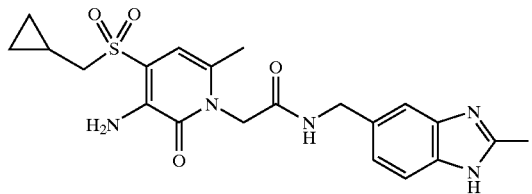
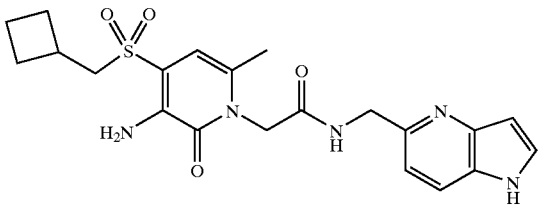
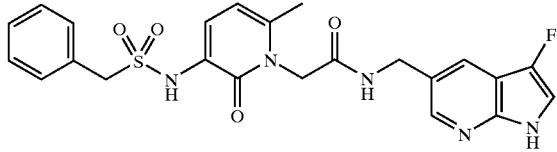
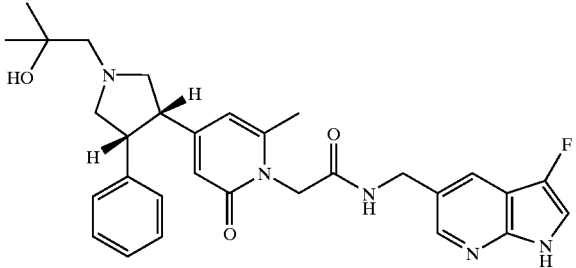
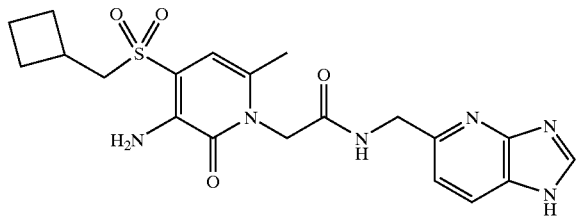

One family of compounds of the invention, and pharmaceutically acceptable salts thereof, includes

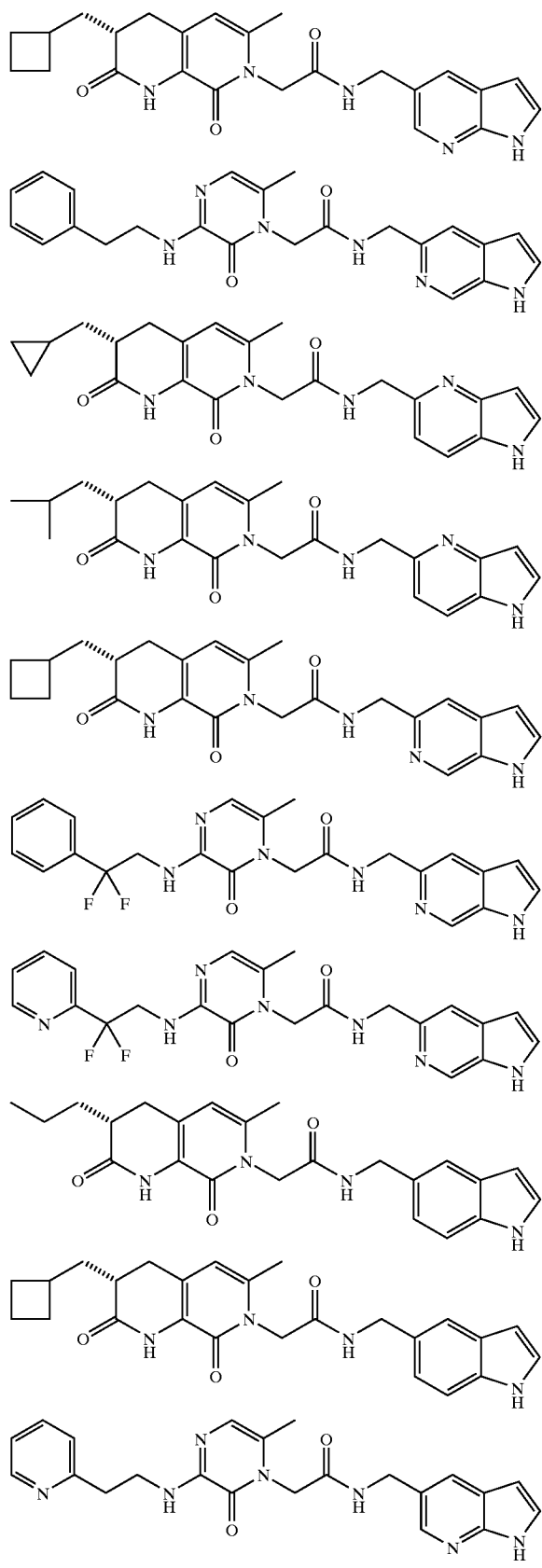

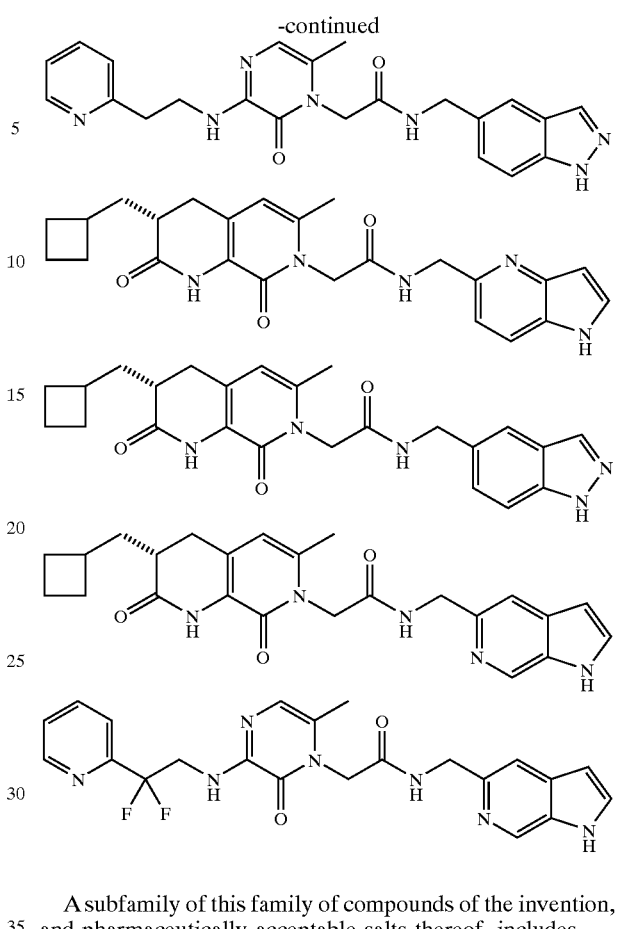

A subfamily of this family of compounds of the invention, and pharmaceutically acceptable salts thereof, includes

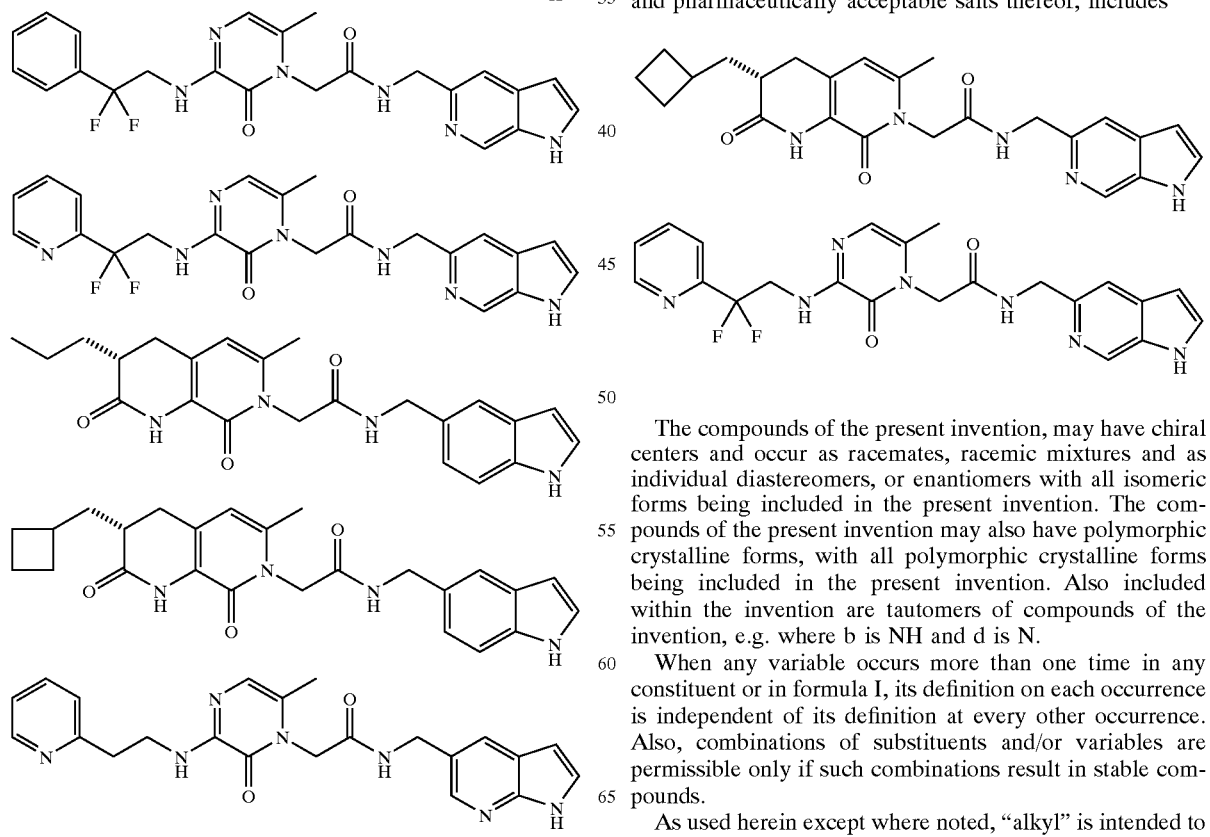

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention. Also included within the invention are tautomers of compounds of the invention, e.g. where b is NH and d is N.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6- to 10-membered mono- or bicyclic ring system. The aryl ring can be unsubstituted or substituted with one or more of $C_{1-4}$ lower alkyl; hydroxy; alkoxy; halogen; amino. Examples of "aryl" groups include phenyl and naphthyl.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl; pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unsaturated heterocyclic nrngs may also be referred to hereinafter as "heteroaryl" rings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quatemized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Some abbreviations that may appear in this application are as follows.

ABBREVIATIONS

| Designation | Protecting Group |
|---|---|
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-C 1 | bis(2-oxo-3-oxazolidinyl)phosphinic chloride |
| EDC | 1-ethyl-3-(3-dimethylaminopropyl) carbodiimide hydrochloride |
| | Other |
| $(BOC)_2O$ ($BOC_2O$) | di-t-butyl dicarbonate |
| n-$Bu_4$N+F- | tetrabutyl ammonium fluoride |
| nBuLi (n-Buli) | n-butyllithium |
| DMF | dimethylformamide |
| $Et_3N$ (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |

In vitro Assay for Determining Proteinase Inhibition

Assays of human α-thrombin and human trypsin were performed by the methods substantially as described in *Thrombosis Research*, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM $CaCl_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration=0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o$, $V_i$ on [I] shown in equation 1:

$$V_o, V_i = 1 + [I]/K_i \quad (1).$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki).

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammals blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intra muscularly as depot injections or implants. Implants may employ inert materials such as biodegradable polymers or synthetic silicones, for example, Silastic, silicone rubber or other polymers manufactured by the Dow-Coming Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An.ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient. would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8, mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
| --- | --- | --- | --- |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

General Procedure for Making Compounds of the Invention

Compounds may be prepared, for example, by a common condensation reaction between a group having a carboxylic acid moiety and a group having an amino moiety, forming a peptide or amide bond. Compounds may be prepared by other means however, and suggested starting materials and procedures described below are exemplary only and should not be construed as limiting the scope of the invention.

In general, compounds having the general structure

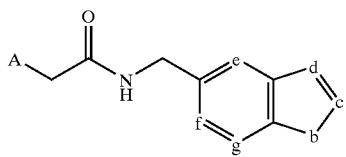

wherein the variables have the above-described meanings, can be prepared by reacting

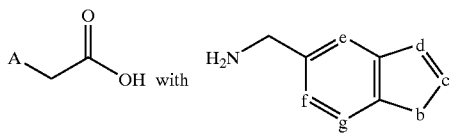

under conditions suitable for forming amide bond between the acid and the amine.

3-Fluoroazaindoles

The 3-fluoroazaindoles are prepared by reaction of the azaindole with an electrophilic fluorinating agent such as 1-chloromethyl-4-fluoro-1,4-diazoniabicyclo[2.2.2]octane bis(tetrafluoroborate) in methanolic acetonitrile to give the 2-methoxy-3-fluoroazaindoline. Treatment with base gives the 3-fluoroazaindole. Obvious variations and modifications of the method to produce similar and obvious variants thereof, will be apparent to one skilled in the art.

6-Halorenated Pyrazinones

The 6-halogenated pyrazinones are prepared from the unsubstituted pyrazinone by treatment with an electrophilic halogenating reagent such as NBS or NCS. Alternatively, the 6-chloropyrazinones are prepared from 2-chloro-3,5-dibromo-6-hydroxypyrazine by alkylation with an acetate equivalent such as ethylbromoacetate. Displacement with an amine then gives the ethyl 3-amino-5-bromo-1-carboxymethyl-6-chloropyrazinone. The bromine is reductively cleaved with tin hydride and a radical initiator. The 5,6-dichloropyrazinones are prepared from 2,3,5-trichloro-6-hydroxypyrazine using similar procedures. Obvious variations and modifications of the method to produce similar and obvious variants thereof, will be apparent to one skilled in the art.

Suitable carboxylic acid starting materials for

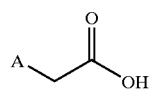

may be prepared according to the following procedures.

Carboxylic Acids

METHOD 1

Starting allylamine is condensed with acetaldehyde and cyanide in Step A to afford the aminonitrile. This is reacted in Step B with oxalyl chloride according to the method of Hoornaert [*J. Heterocyclic Chem.*, 20, 919, (1983)] to give the pyrazinone. The olefin is oxidatively cleaved with ruthenium tetraoxide and the resulting aldehyde is converted to the acid by an oxidizing agent such as chromic acid in Step C. The 3-chloro group is then displaced by an ammonia equivalent, in this case p-methoxybenzylamine in Step D. The remaining chlorine is removed by reduction with Raney nickel in Step E and in Step F the p-methoxybenzyl group is removed by treatment with a strong acid such as TFA.

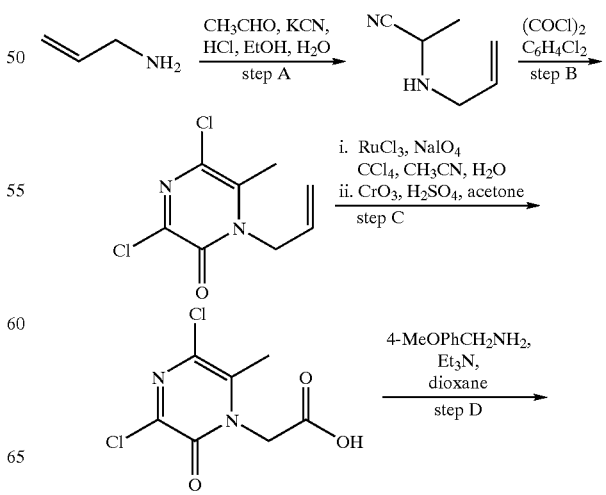

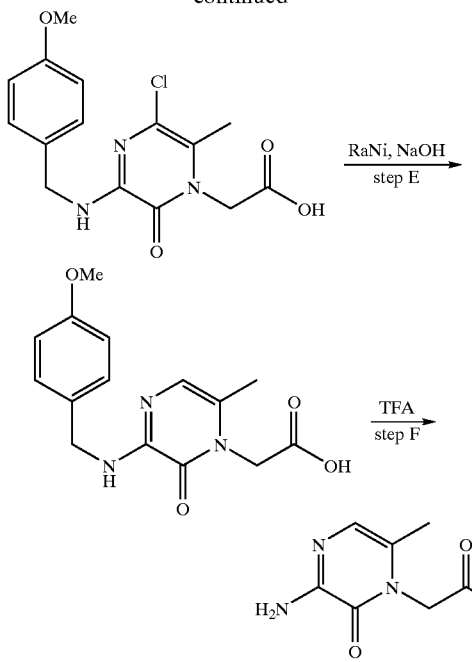

Typically, solution phase amide couplings may be used to form the final product, but solid-phase synthesis by classical Merrifield techniques may be employed instead. The addition and removal of one or more protecting groups is also typical practice.

Modifications of the method will allow different W, $R^3$, X and A groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. Obvious variations and modifications of the method to produce similar and obvious variants thereof, will be apparent to one skilled in the art.

METHOD 2

The acid from METHOD 1, Step C is coupled to the appropriate amine. The 3-chloro group is then displaced by the appropriate amine and a protecting group is then removed, if necessary, to give the final product.

Modifications of the method will allow different W, $R^3$, and X groups contemplated by the scope of the broad claim below to be present by the use of an appropriate reagent or appropriately substituted starting material in the indicated synthetic step. Obvious variations and modifications of the method to produce similar and obvious variants thereof, will be apparent to one skilled in the art.

METHOD 3

An ester of glycine, in this case the benzyl ester, is condensed with acetaldehyde and cyanide in Step A to afford the aminonitrile. This is reacted in Step B with oxalyl chloride to give the pyrazinone. The 3-chloro group is then displaced by the appropriate amine, in this case phenethylamine, in Step C. The ester is hydrolyzed in Step D and the remaining chlorine is then removed by hydrogenolysis in Step E.

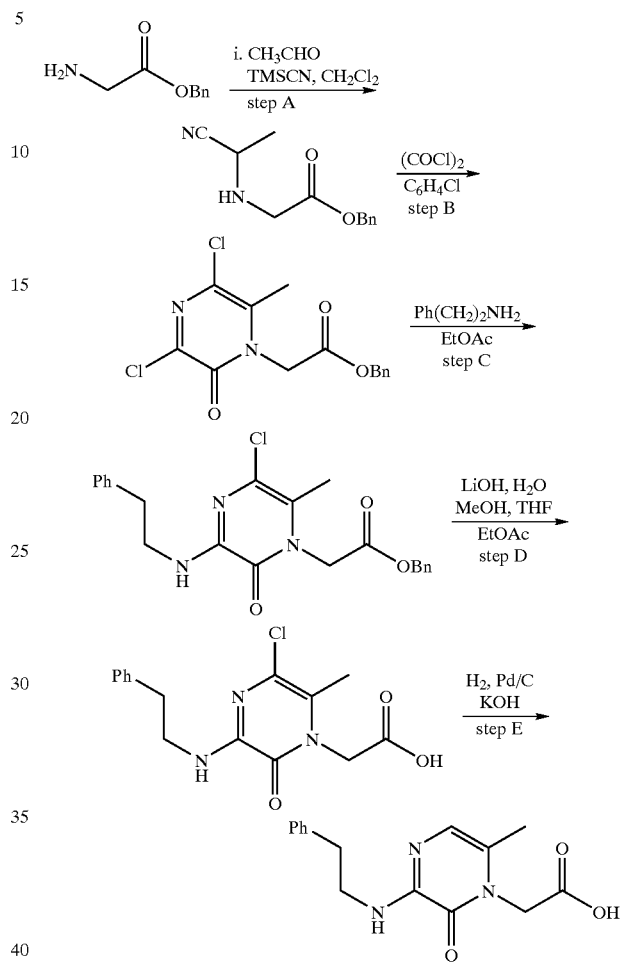

METHOD 4

Starting allylamine is condensed with acetaldehyde and cyanide in Step A to afford the aminonitrile. This is reacted in Step B with oxalyl chloride according to the method of Hoornaert [*J. Heterocyclic Chem.*, 20 919, (1983)] to give the pyrazinone. The olefin is oxidatively cleaved with ruthenium tetraoxide and the resulting aldehyde is converted to the acid by an oxidizing agent such as chromic acid in Step C. The 3-chloro group is then displaced by the appropriate amine, in this case phenethylamine, in Step D and the remaining chlorine is then removed by reduction with Raney nickel in Step E.

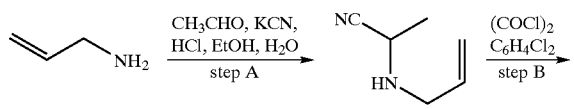

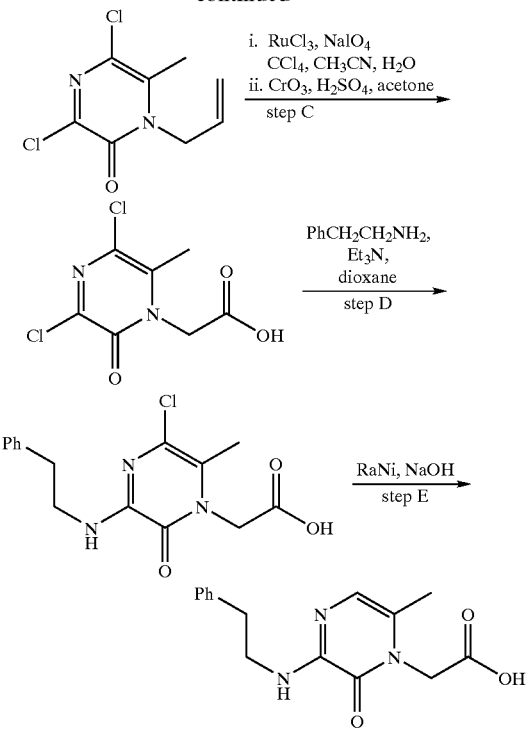

Amide couplings to form the compounds of this invention can be performed by the carbodiimide method. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of the method will allow different W, $R^3$, X and A groups contemplated by the scope of the broad claim below to be present by the use of an appropriate reagent or appropriately substituted starting material in the indicated synthetic step. For example the starting aldehyde in Step A can have as its side chain, ethyl, isopropyl, cyclopropyl, trifluoromethyl, and the like, to achieve the different operable values of $R^3$. Likewise, different W groups can be present by the use of an appropriate amine in Step D. Different X groups can be present by the omission of step E, and by the use of a reagent such as oxalyl bromide in step B. Obvious variations and modifications of the method to produce similar and obvious variants thereof, will be apparent to one skilled in the art.

METHOD 5

Formation of [RS]-3-benzyl-7-carboxymethyl-6-methyl-2-oxo-1,2,3,4-tetrahydro-1,7-naphthiridin-[7H]-8-one (5) is a useful intermediate for preparing compounds of the invention.

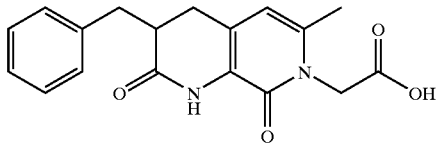

It is prepared as follows:
Step A: Ethyl 6-Methyl-3-nitropyridone 4-Carboxylate

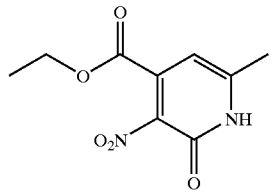

To a slurry nitroacetamide ammonia salt (70.3 g, 581 mmol) in 400, mL of deionized water was added 100 g (633 mmol, 1.09 equiv.) of ethyl 2,4-dioxovalerate followed by a solution of piperdinium acetate (prepared by adding 36 mL of piperdine to 21 mL of acetic acid in 100 mL of water). The resulting solution was stirred at 40° C. for 16 h then cooled in an ice bath. The precipitated product was filtered and washed with 50 mL of cold water to afford the above pyridone as a yellow solid.
$^1$H NMR (CDCl$_3$) d 6.43 (s, 1H), 4.35 (q, J=7 Hz, 2H), 2.40 (s, 3H), 1.35 (t, J=7 Hz, 3H).
Step B: Ethyl 2-Methoxy-6-methyl-3-nitropyridine 4-Carboxylate

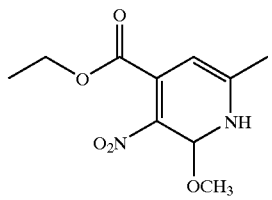

A solution of the pyridone from step A (6.2 g, 27.4 mmol) in 50 mL of DCM was treated with 4.47 g (30.2 mmol) of solid trimethyloxonium tetrafluoroborate and the mixture was stirred at 40° C. until the reaction was judged to be complete by HPLC (typically 24–72 h). The reaction mixture was concentrated to one-third volume, loaded onto a silica gel column and eluted with 2:3 EtOAc/Hexane to afford the methoxy pyridine as a yellow liquid.
$^1$H NMR (CDCl$_3$) d 7.2 (s, 1H), 4.35 (q, J=7 Hz, 2H), 4.05 (s, 3H), 2.55 (s, 3H) 1.35 (t, J=7 Hz, 3H).
Step C: 4-Hydroxymethyl-2-methoxy-6-methyl-3-nitropyridine

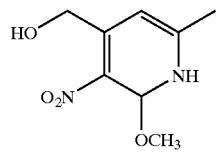

To a −70° C. solution of ester from step B (5.4 g, 22.5 mmol) in 140 mL of DCM was added 56.2 mL (56.2 mmol)

of DIBAL-H (1M in hexane) by dropping funnel. The resulting solution was stirred for 1 h then warrned to room temperature over an additional hour. The reaction mixture was quenched by the careful addition of saturated NaK tartrate. Stirring was continued for 30 min then the solid was filtered and washed with 100 mL of DCM. The filtrate was extracted with 2×50 mL of saturated NaK tartrate then brine (25 mL). The yellow solution was concentrated and chromatographed (2:3 EtOAc/Hexane) to afford the desired alcohol as a yellow solid.

$^1$H NMR (CDC13) d 7.00 (s, 1H), 4.70 (s, 2H), 4.05 (s, 3H), 2.50 (s, 3H), 2.10 (bs, 1H).

Step D: 4-Formyl-2-methoxy-6-methyl-3-nitropyridine

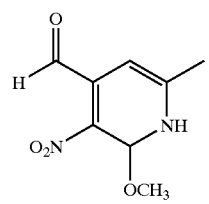

(5d)

To a −70° C. solution of oxalyl chloride (2.0 mL, 22 mmol) in 50 mL of DCM was added 3.4 mL (44 mmol) of DMSO in 10 mL of DCM by dropping funnel. After 2 min, the reaction mixture was treated with 3.99 g (20 mmol) of the alcohol from step C in 20 mL of DCM. The solution was stirred for an additional 15 min at −70° C., treated with 14 mL (50 mmol) of Et$_3$N and warmed to ambient temperature over 90 min. The reaction was quenched with 100 mL of water and the two phases were separated. The aqueous phase was extracted with 100 mL of DCM and the combined organic extracts were washed with 50 mL of brine and dried over MgSO$_4$. The yellow solution was concentrated and chromatographed (2:3 EtOAc/Hexane) to afford the aldehyde as a yellow solid.

1H NMR (CDCl$_3$) d 10.05 (s, 1H), 7.10 (s, 1H), 4.70 (s, 2H), 4.05 (s, 3H), 2.60 (s, 3H).

Step E: Methyl-2-benzyl-3-(4-[6-methyl-2-methoxy-3-nitropyridyl])-acrylate:

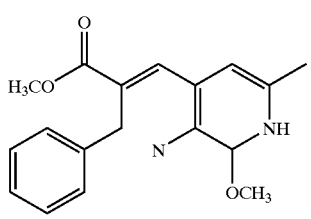

(5e)

To a 0° C. solution of 2-benzyl-trimethylphosphonoacetate (1.36 g, 5.0 mmol) in 25 mL of THF was added 145 mg (4.75 mmol) of NaH. The mixture was stirred for 30 min before the dropwise addition of 930 mg (4.75 mmol) of 4-forrnyl-2-methoxy-3-nitropyridine in 15 mL of THF. The solution was then heated at 50° C. for 3 h, cooled and evaporated. The residue was redissolved in 100 mL of EtOAc and quenched to pH=7 with saturated NH$_4$Cl. The organic phase was washed with brine and dried over MgSO$_4$. Column chromatography (2:3 EtOAc/Hexane) afforded the desired olefin as a mixture of E- and Z-isomers.

$^1$H NMR (CDCl$_3$) d 7.60 (s, 1H), 7.40–7.00 (m, 6H), 6.60 (2 singlets, 2H), 4.00 (2 singlets, 6H), 3.75 (2 singlets, 8H), 2.40 (2 singlets, 6H).

Step F: [RS]-3-Benzyl-6-methyl-8-methoxy-2-oxo-1,2,3,4-tetrahydro-1,7-naphthiridine:

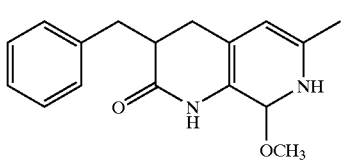

(5f)

To a solution of nitro olefin from step E (1.6 g, 4.75 mmol) in 50 mL of EtOAc was added 400 mg of 10% Pd(C). Hydrogen gas was added and the solution was heated at 50° C. for 16. The reaction mixture was filtered through Celite and the filtrate evaporated. Column chromatography (2:3 EtOAc/Hexane) afforded the bicyclic lactam as a white solid.

$^1$H NMR (CDCl$_3$) d 7.45 (bs, 1H), 7.40–7.20 (m, 5H), 6.45 (s, 1H), 3.95 (s, 3H), 3.35 (dd, 1H), 2.80 (m, 2H), 2.60 (m, 2H), 2.40 (s, 3H).

Step G: [RS]-3-Benzyl-6-methyl-2-oxo-1,2,3,4-tetrahydro-1,7-naphthiridin-[7H]-8-one:

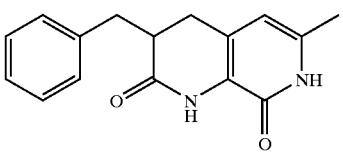

(5g)

To a 23° C. solution of methoxypyridine from step F (700 mg, 2.48 mmol) in 25 mL of dichloroethane was added 8.0 mL (8.0 mmol) of BB$_{r3}$ (1M in DCM). An insoluble gum precipitates within 5 min and the reaction was allowed to stir an additional 90 min before quenching to pH=8 with saturated NaHCO$_3$. The mixture was diluted with 100 mL of EtOAc and 10 mL THF. The aqueous phase was discarded and the organic solution was washed with 10 mL of water then 10 mL of brine. Evaporation of the solvent left a tan colored solid which was used without further purification.

$^1$H NMR (CDCl$_3$) d 8.20 (bs, 1H), 7.40–7.10 (m, 5H), 5.88 (s, 1H), 3.35 (dd, 1H), 2.80–2.50 (m, 4H), 2.25 (s, 3H).

Step H: [RS]-3-Benzyl-7-t-butoxycarbonylmethyl-6-methyl-2-oxo-1,2,3,4-tetrahydro-1,7-naphthiridin-[7H]-8-one:

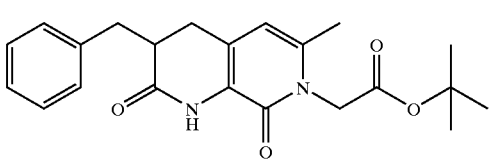

(5h)

To a 23° C. solution of pyridone from step G (630 mg, 2.5 mmol) in 20 mL of DMF was added 812 mg (2.5 mmol) of Cs$_2$CO$_3$ and 0.37 mL (2.5 mmol) of tert-butyl bromoacetate. The reaction mixture was allowed to stir for 16 h before removal of the solvent in vacuo. The mixture was diluted with 100 mL of EtOAc and 25 mL water. The aqueous phase was discarded and the organic solution was washed with 20 mL of brine. Evaporation of the solvent and chromatography (1:1 EtOAc/Hexane) of the resulting oil left the alkylated pyridone as a white solid.

$^1$H NMR (CDCl$_3$) d 7.84 (bs, 1H), 7.33–7.17 (m, 5H), 5.87 (s, 1H), 4.79 (q, J=17.2 Hz, 2H), 3.36 (dd, J=4.1,13.5

Hz, 1H), 2.79 (m, 1H), 2.65 (m, 2H), 2.48 (m, 1H), 2.23 (s, 3H), 1.48 (s, 9H).

Step I: [RS]-3-Benzyl-7-carboxymethyl-6-methyl-2-oxo-1,2,3,4-tetrahydro-1,7-naphthiridin-[7H]-8-one:

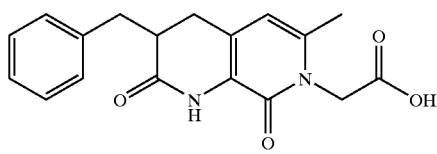

(5i)

To a 0° C. solution of ester from step H (310 mg, 0.85 mmol) in 30 mL of DCM was added 8 mL of trifluoroacetic acid. The reaction mixture was allowed to stir to ambient temperature over 5 h before removal of the solvent in vacuo. The resulting solid was azeotroped with benzene, EtOAc then ether. This process yielded the desired carboxylic acid as a white solid.

$^1$H NMR (DMSO-d6) d 8.92 (bs, 1H), 7.35–7.10 (m, 5H), 6.04 (s, 1H), 4.75 (q, J=17.2 Hz, 2H), 3.16 (dd, J=4.2,13.7 Hz, 1H), 2.79 (m, 1H), 2.65–2.40 (m, 3H), 2.1 (s, 3H).

Additional exemplary compounds of the invention, shown in Tables 2 and 3, can be prepared according to the general schemes which follow the table and which are subsequently exemplified.

TABLE 2

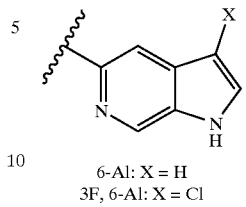

| R$^1$ | R$^2$ | R$^3$ | Ki, nM |
|---|---|---|---|
| H | i-Pr | 6-AZ | ** |
| H | i-Pr | 3-F, 7-AI | ** |
| H | i-Pr | 7-AI | ** |
| H | CF$_3$ | 6-AI | ** |
| COCH$_3$ | i-Pr | 6-AI | * |
| OH | i-Pr | 6-AI | * |
| OH | i-Pr | 3-Cl, 6-AI | * |

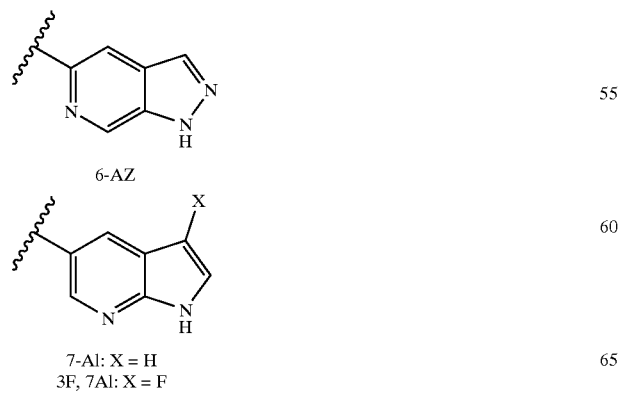

6-AZ

7-AI: X = H
3F, 7AI: X = F

6-AI: X = H
3F, 6-AI: X = Cl

TABLE 3

| R$^1$ | R$^2$ | R$^3$ | Ki, nM |
|---|---|---|---|
| EtNH— | (i-Pr)$_2$NCO— | IN | * |
| c-PrCH$_2$NH— | piperidine-NCO— | BI | ** |
| c-Pr(CH$_2$)$_2$NH— | piperidine-NCO— | BI | * |
| HO— | (i-Bu)$_2$NCO— | 4-AI | * |
| HO— | 2,6-dimethylpiperidine-NCO— | BI | * |
| H | (i-Bu)$_2$NCO— | 6-AI | * |
| c-Pr(CH$_2$)$_3$NH— | piperidine-NCO— | 6-AI | * |
| HO— | (i-Bu)$_2$NCO— | 6-AI | * |

6-AI: X = H

4-AI

TABLE 3-continued
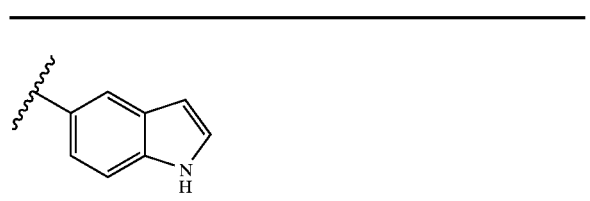
IN
BI
METHOD 6
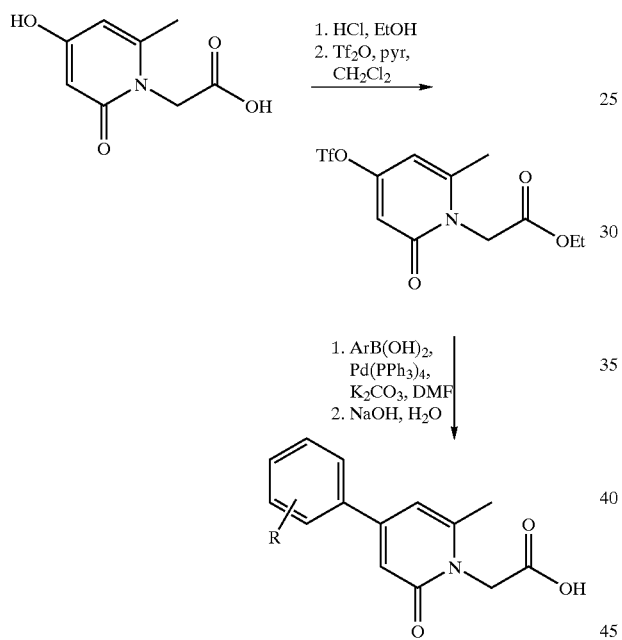
METHOD 7
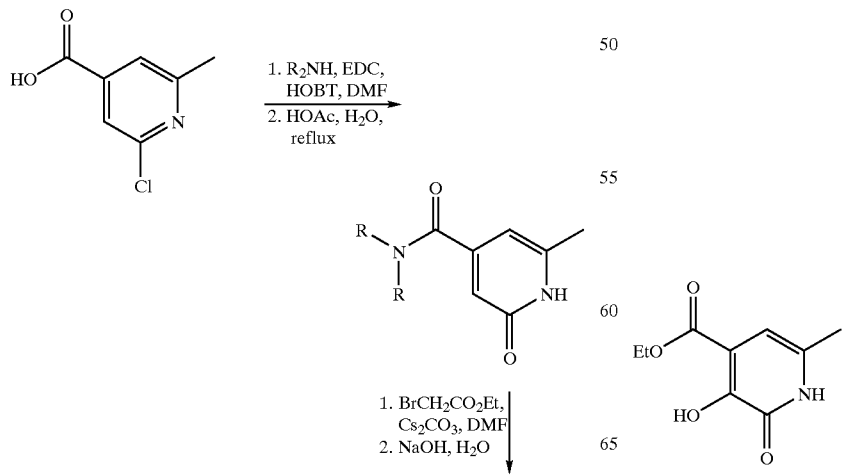
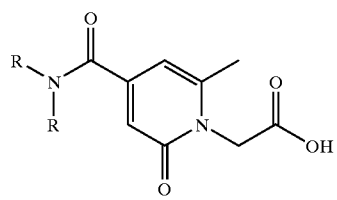
R is independently hydrogen, $C_{1-5}$ alkyl, or the two R groups may be joined together to formn a 5-, 6-, or 7-membered ring unsubstituted, mono-substituted, independently di-substituted, or independently tri-substituted with $C_{1-5}$ alkyl groups.
METHOD 8
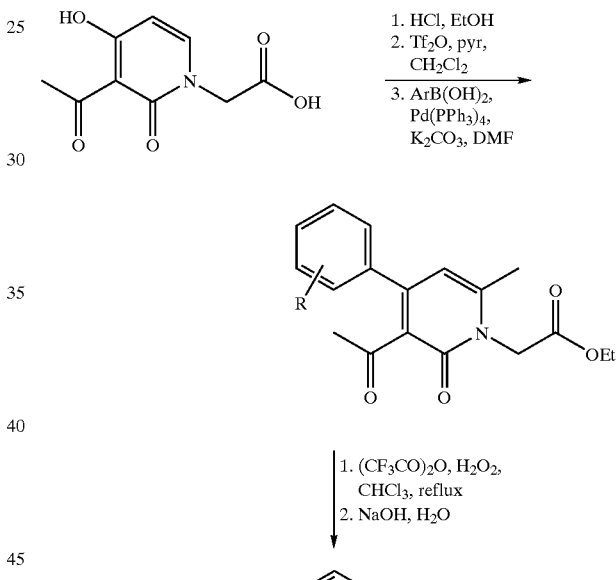
METHOD 9
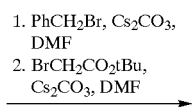

63

-continued

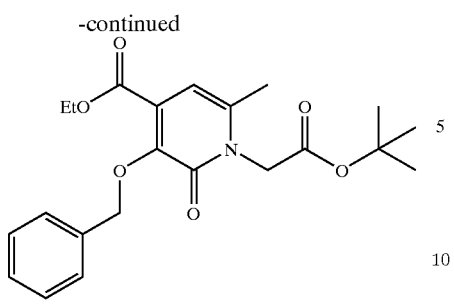

1. NaOH, H₂O
2. R²NH, EDC, HOBT, DMF
3. H₂, Pd—C, EtOH
4. TFA, CH₂Cl₂

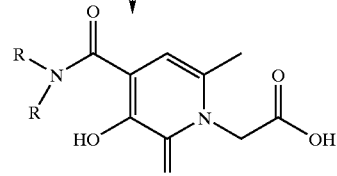

METHOD 10

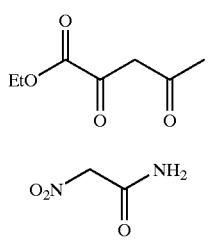

piperidine, HOAc

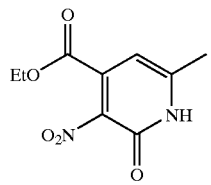

1. BrCH₂CO₂tBu, Cs₂CO₃, DMF
2. H₂Pd—C, EtOH

64

-continued

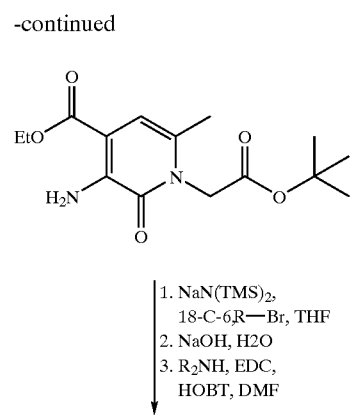

1. NaN(TMS)₂, 18-C-6,R—Br, THF
2. NaOH, H2O
3. R₂NH, EDC, HOBT, DMF

TFA, CH₂Cl₂

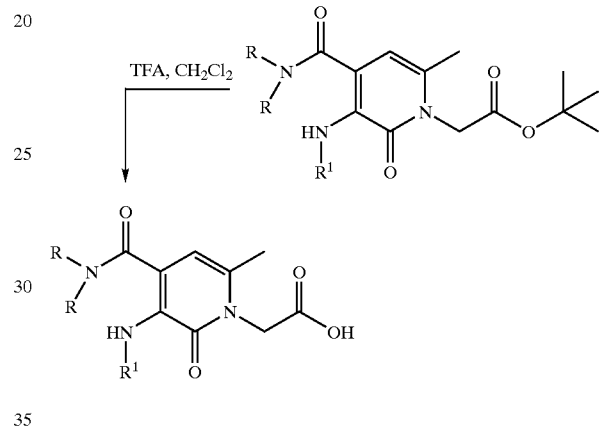

R is independently hydrogen, $C_{1-5}$ alkyl, or the two R groups may be joined together to form a 5-, 6-, or 7-membered ring unsubstituted, mono-substituted, independently di-substituted, or independently tri-substituted with $C_{1-5}$ alkyl groups.

$R^1$ is hydrogen or $C_{1-5}$ alkyl unsubstituted or substituted with cylopropane.

METHOD 11

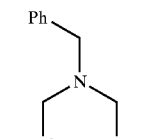

+

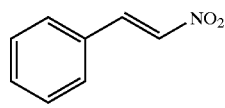

cat. TFA, CH₂Cl₂, 0° C.

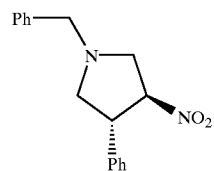

H₂, Raney Ni
EtOH

-continued
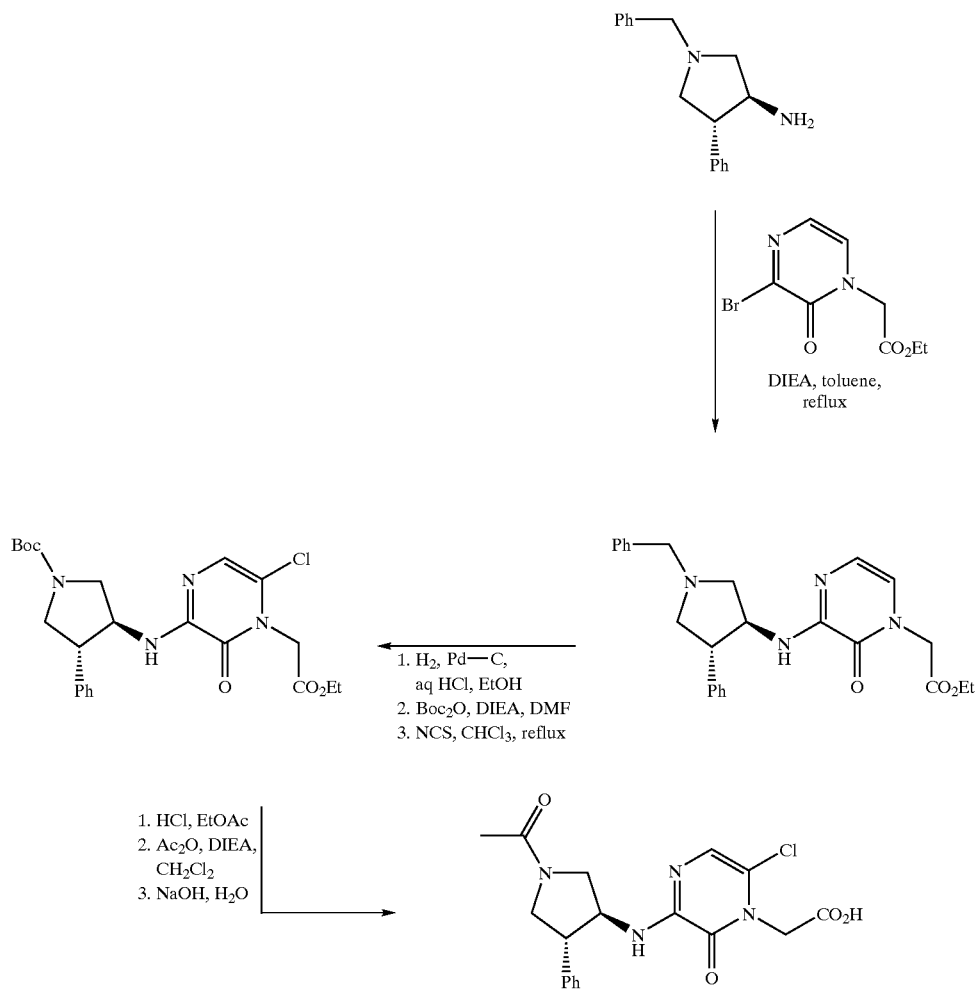
METHOD 12
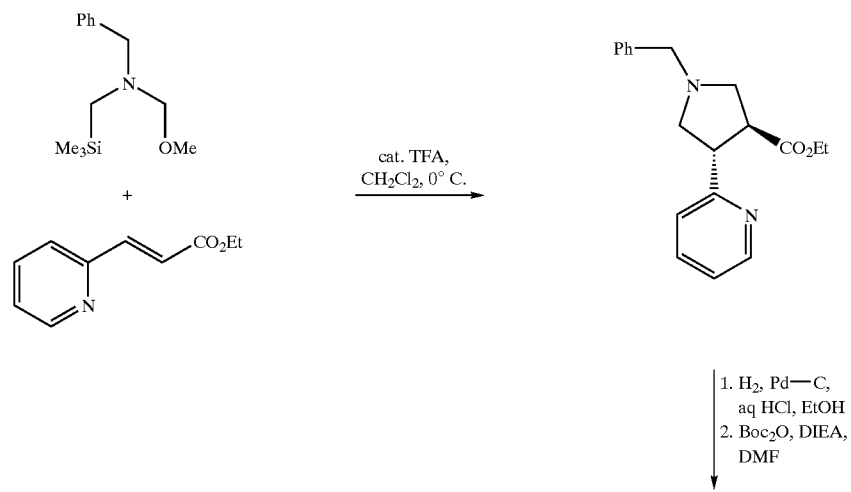

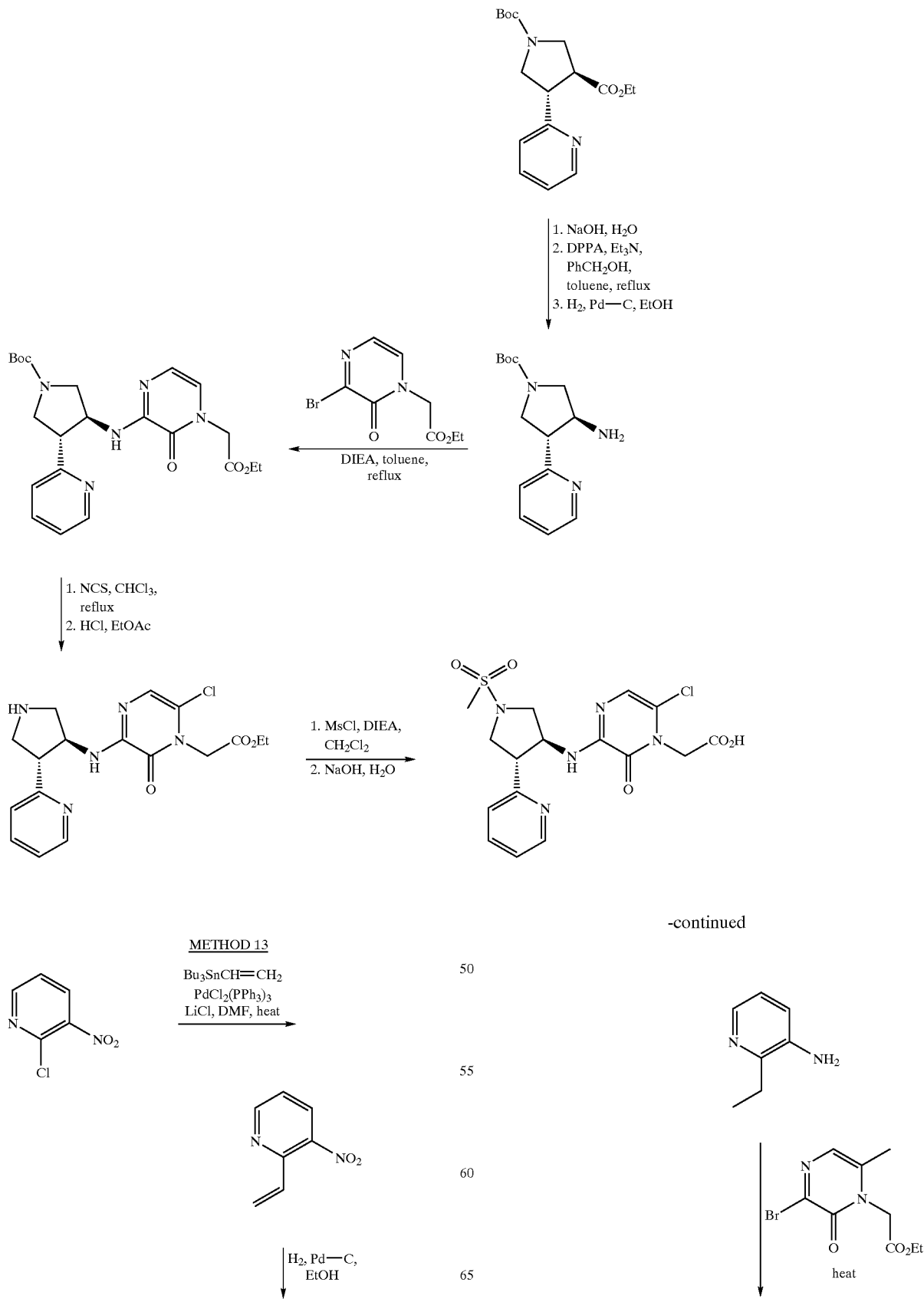

-continued
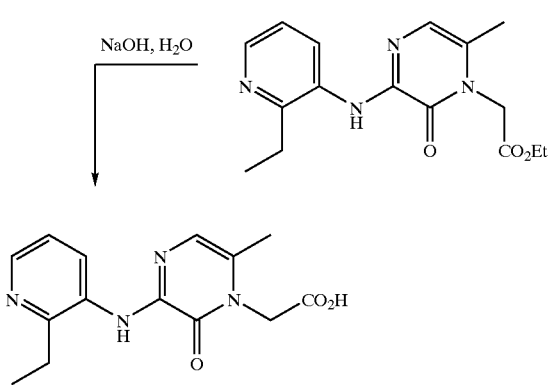
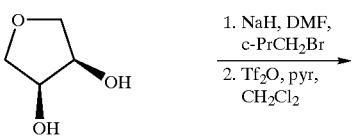
METHOD 14
1. NaH, DMF, c-PrCH₂Br
2. Tf₂O, pyr, CH₂Cl₂
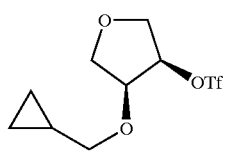
1. NaN₃, DMF
2. PPh₃, THF, H₂O
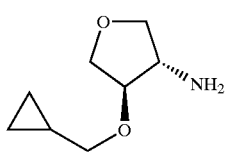
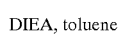
DIEA, toluene, reflux
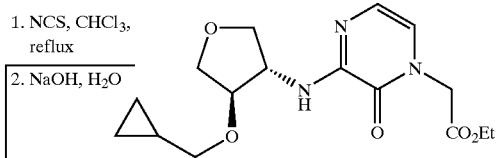
1. NCS, CHCl₃, reflux
2. NaOH, H₂O
-continued
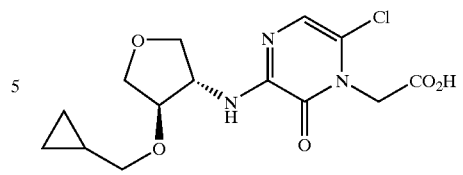
METHOD 15
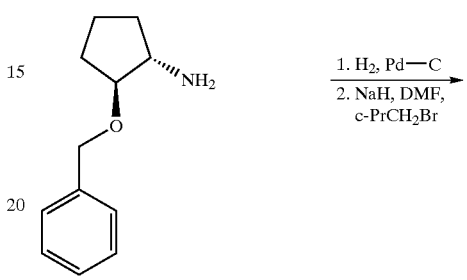
1. H₂, Pd—C
2. NaH, DMF, c-PrCH₂Br
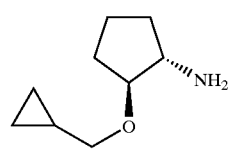
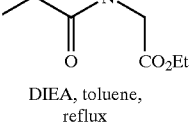
DIEA, toluene, reflux
1. NCS, CHCl₃, reflux
2. NaOH, H₂O
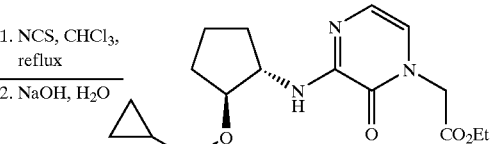
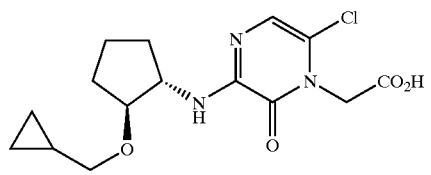

METHOD 16
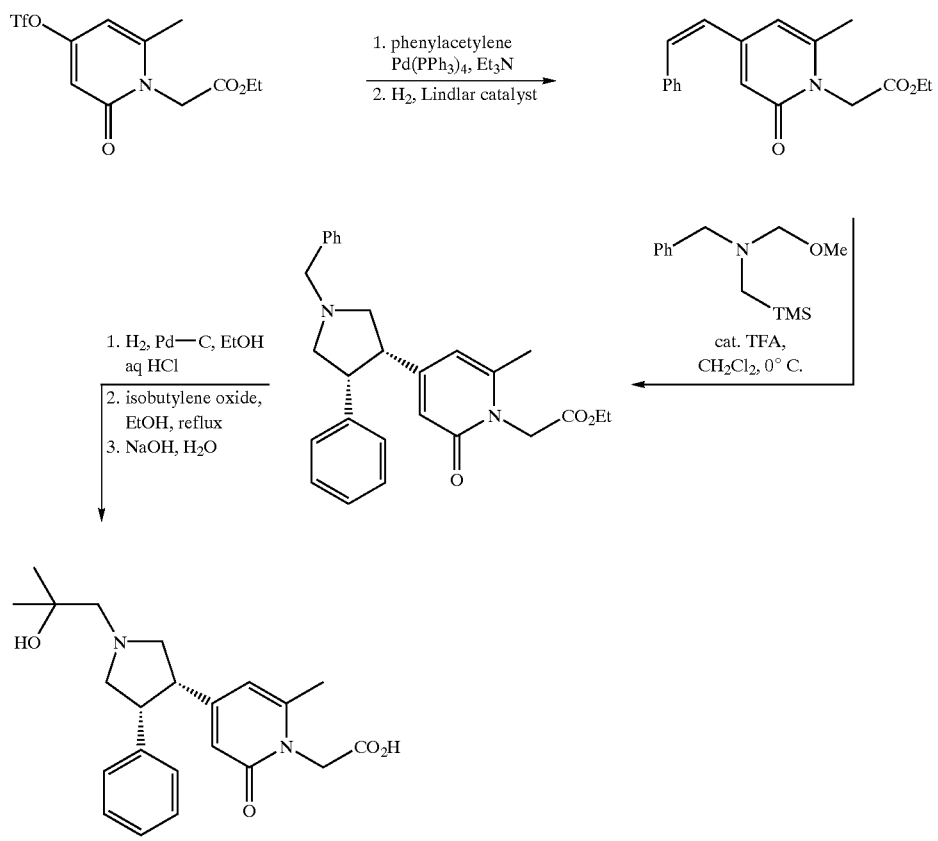
METHOD 17
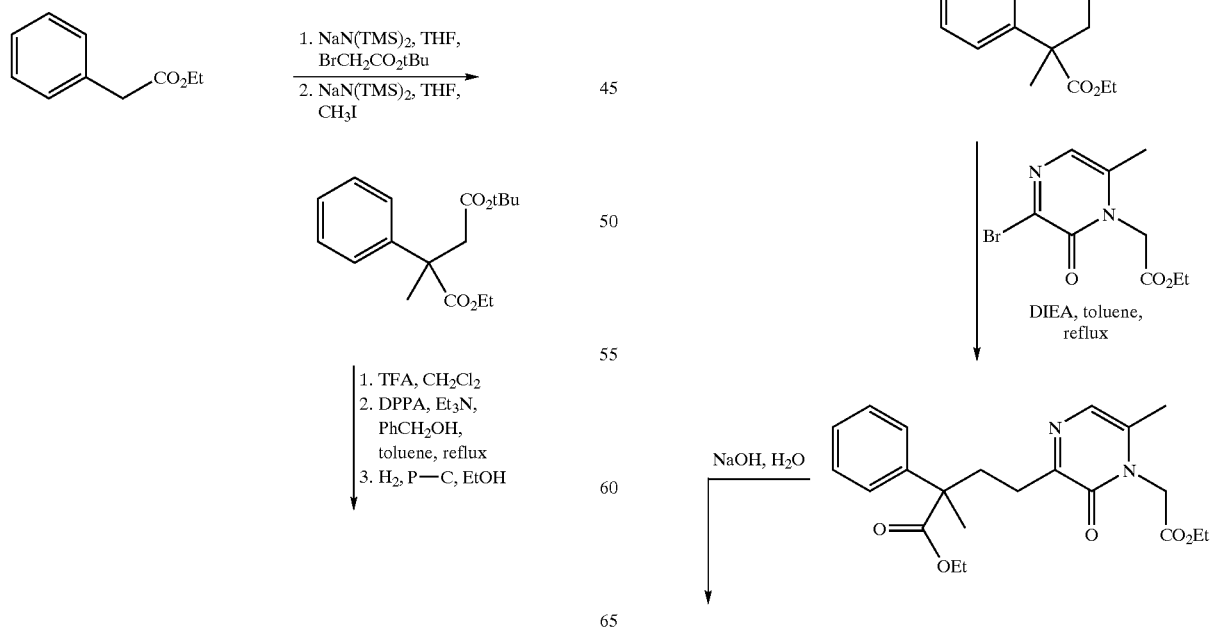

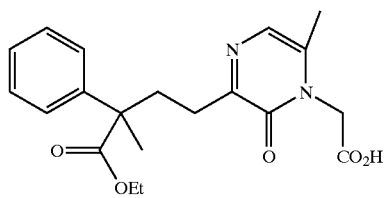
METHOD 18
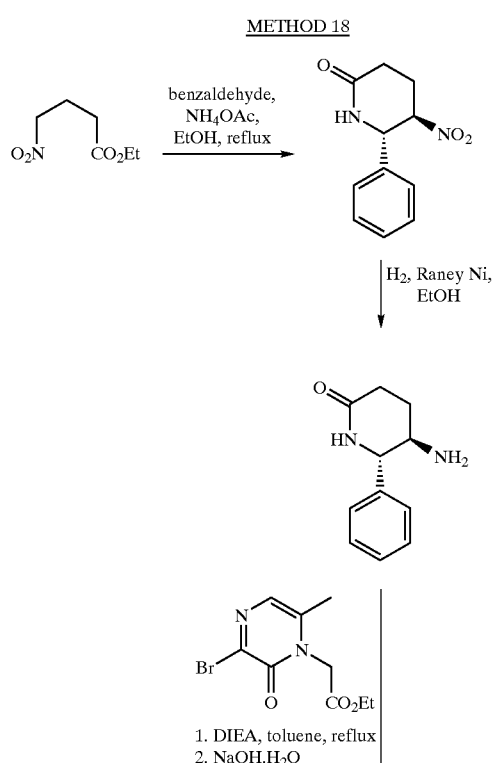
METHOD 19
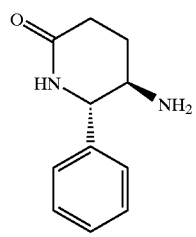
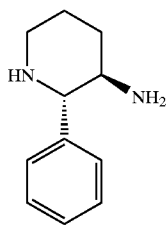
In the following Examples HPLC Method A and HPLC Method B refer to the following methods:
HPLC Method A:
Vydac C18 reverse phase column
95:5:0.1 to 0:100:0.1 H2O:CH3CN:TFA gradient over 15 minutes
flow rate 2 mL/min
HPLC Method B:
Vydac C18 reverse phase column
95:5:0.1 to 5:95:0.1 H2O:CH3CN:TFA gradient over 45 minutes flow rate 1.5 mL/min
EXAMPLE 1
Preparation of
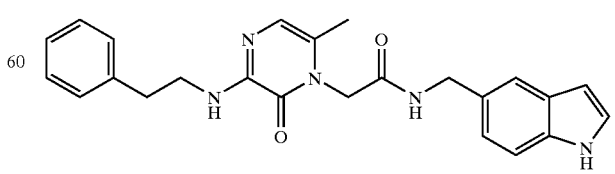

250 mg (0.870 mmoles) 3-(2-Phenethylwnino)-6-methyl-1-carboxymethylpyrazinone (1-1),

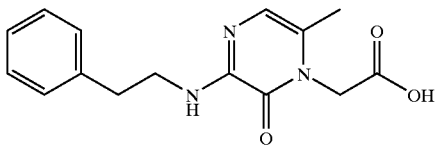

prepared according to Method 3 or Method 4 above, was combined with 110.6 mg (0.757 mmoles) of 5-aminomethyl indole (1-2), 123.4 mg (0.913 mmoles) of HOBT, 175.0 mg (0.913 mmoles) of EDC, and 176.1 mg (1.74 mmoles) of $Et_3N$ with DMF (4 mL) and stirred at room temperature. After 16 hours, the resulting material was concentrated and then diluted with EtOAc and 5% $NaHCO_3$. Insoluble precipitate was collected by filtration and was stirred as a suspension in 5 ml MeOH. EtOH/HCl was added dropwise until solution was acidic and became nearly homogeneous. After 5 minutes, the solution was concentrated, and azeotroped with MeOH two times. EtOAc was added to the resulting material. Solid was collected and dried 16 hours under high vacuum at 42° C., resulting in an off-white solid 1-3.

HRMS (FAB) $C_{24}H_{26}N_5O_2$ (M+1) calcd. 416.2081. Found: 416.2085.

EXAMPLE 2

Amides of 5-Aminomethyl-7-azaindole were Prepared as Follows

Step A: 7-Aza-5-bromoindoline

See Van Der Plas et al., *Tetrahedron* 1989,45, 803, and Taylor et al. ibid. 1987, 43, 5145. NBS (2.71 g, 15.2 mmol) was added to a stirred solution of 7-azaindoline (1.83 g, 15.2 mmol, in chloroform (200 mL). After 1 h, the reaction mixture was washed with 10% sodium metabisulfite solution, dried ($Na_2SO_4$), filtered through a pad of silica (eluting with ethyl acetate) and evaporated in vacuo to give the title compound:

$^1$H NMR ($CDCl_3$) δ 3.09 (t, J=8.5 Hz, 2H), 3.74 (t, J=8.5 Hz, 2H), 5.00 (br s, 1H), 7.32 (s, 1H), 8.13 (s, 1H).

Step B: 7-Aza-5-cyanoindoline

A stirred mixture of 7-aza-5-bromoindoline (171 mg, 0.86 mmol), zinc cyanide (61 mg, 0.52 mmol) and tetrakis(triphenylphosphine)palladium(0) (60 mg, 0.052 mmol) in DMF (1 mL) was heated to 80° C. under argon. After 5 h, the reaction mixture was partitioned between methylene chloride and water. The organic layer was dried ($MgSO_4$) and evaporated in vacuo. The crude product was purified by flash column chromatography on silica (80% ethyl acetate/hexanes) to give the title compound:

$^1$H NMR ($CDCl_3$) δ 3.07 (m, 2H), 3.65 (t, J=8.4 Hz, 2H), 4.52 (br s, 1H), 7.31 (s, 1H), 7.85 (s, 1H).

Step C: 5-Aminomethyl-7-azaindoline Dihydrochloride

A suspension of 7-aza-5-cyanoindoline (98 mg, 0.68 mmol) and 10% palladium on carbon (50 mg) in methanol (10 mL) and 6 M HCl (1 mL) was shaken on a Parr apparatus under hydrogen (55 psi) for 16 h. The mixture was filtered through celite and evaporated in vacito to give the title compound:

$^1$H NMR ($CD_3OD$) δ 3.30 (obscured t, 2H), 3.95 (t, J=8.2 Hz, 2H), 4.03 (s, 2H), 7.66 (s, 2H).

Step D: 3-(2-Phenethylamino)-6-methyl-1-(5-methylcarboxamido-methyl-7-azaindolinyl)-pyrazinone bis-TFA Salt The title compound was prepared using standard procedures from 3-(2-phenethylamino)-6-methyl-1-carboxymethylpyrazinone and 5-aminomethyl-7-azaindoline dihydrochloride.

Step E: 3-(2-Phenethylamino)-6-methyl-1-(5-methylcarboxamido-methyl-7-azaindolyl)-pyrazinone bis-TFA Salt

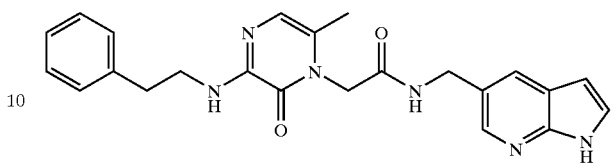

A mixture of manganese dioxide (9 mg, 0.1 mmol) and 3-(2-phenethylamino)-6-methyl-1-(5-methylcarboxamidomethyl-7-azaindolinyl)-pyrazinone bis-TFA salt (12.3 mg, 0.02 mmol) in DMF (1 mL) was stirred for 2 h. Methanol was added and the mixture was filtered through celite and evaporated in vacuo. The residue was dissolved in a mixture of methanol and 1 M HCl in ether and was evaporated in vacuo. The crude product was purified by preparative HPLC ($C_{18}$, acetonitrile/water, 0.1% TFA) to give the title compound:

$^1$H NMR ($CD_3OD$) δ 2.18 (s, 3H), 3.00 (t, J=7.4 Hz, 2H), 3.67 (t, J=7.4 Hz, 2H), 4.58 (s, 2H), 4.78 (s, 2H), 6.54 (s, 1H), 6.63 (d, J=3.7 Hz, 1H), 7.20–7.7.32 (m, 7.53 (d, J=3.7 Hz, 1H), 8.25 (s, 1H), 8.27 (s, 1H).

EXAMPLE 3

Amides of 5-Aminomethyl-6-azaindole were Prepared as Follows

Step A: 2-Bromo-4-methyl-5-nitropyridine

A solution of phosphorus oxybromide (14.4 g, 50 mmol) in 1,2-dichloroethane (50 mL) was added to a stirred suspension of 2-hydroxy-4-methyl-5-nitropyridine (5 g, 32.4 mmol) in 1,2-dichloroethane (50 mL) and the resulting mixture was heated to reflux. After 4 h, the reaction was cooled and quenched with water. The organic layer was dried ($Na_2SO_4$), filtered through a pad of silica eluting with chloroform and evaporated in vacuo to give the title compound as a yellow solid:

$^1$H NMR ($CDCl_3$) δ 2.64 (s, 3H), 7.53 (s, 1H), 8.96 (s, 1H).

Step B: 2-Cyano-4-methyl-5-nitropyridine

The title compound was prepared from 2-bromo-4-methyl-5-nitropyridine using the procedure of Example 2, Step B:

$^1$H NMR ($CDCl_3$) δ 2.72 (s, 3H), 7.74 (s, 1H), 9.21 (s, 1H).

Step C: 2-Cyano-4-(2-dimethylaminoethenyl)-5-nitropyridine

A stirred solution of 2-cyano-4-methyl-5-nitropyridine (2.48 g, 15.2 mmol) in DMF (10 mL) and DMF-dimethylacetal (2.7 mL, 20 mmol) was heated to 90° C. for two h. The solution was cooled and evaporated in vacuo to give the title compound as a deep red solid:

$^1$H NMR ($d_6$-DMSO) δ 2.94 (br s, 3H), 3.20 (br s, 3H), 5.87 (d, J=12.9 Hz, 1H), 8.24 (d, J=12.9 Hz, 1H), 8.29 (s, 1H), 8.83 (s, 1H).

Step D: 5-Aminomethyl-6-azaindole Dihydrochloride

A suspension of 2-cyano-4-(2-dimethylaminoethenyl)-5-nitropyridine (3.8 g) and 10% palladium on carbon (3 g) in 6 M HCl (10 mL) and methanol (50 mL) was shaken on a Parr apparatus under hydrogen (55 psi). After 16 h the mixture was filtered through celite, washing with methanol, and was basified with ammonium hydroxide and evaporated in vacuo. The crude product was purified by flash column chromatography (80:19:1 chloroform/methanol/ammonium hydroxide) to give the title compound as the free base. The free base was dissolved in a minimum volume of methanol and 1 M HCl in ether (2 equivalents) was added and after dilution with ether the solids were collected by filtration to give the title compound as a tan solid:

$^1$H NMR (CD$_3$OD) δ 4.57 (s, 2H), 7.05 (d, J=2.9 Hz, 1H), 8.23 (s, 1H), 8.27 (d, J=2.9 Hz, 1H), 9.14 (s, 1H).

Step E: 3-(2-Phenethylamino)-6-methyl-1-(5-methylcarboxamidomethyl-6-azaindolyl)-prazinone Dihydrochloride

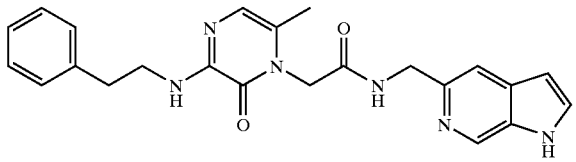

The title compound was prepared using standard procedures from 3-(2-henethylamino)-6-methyl-1-carboxymethylpyrazinone and 5-aminomethyl-6-zaindole dihydrochloride.

HRMS (FAB) C$_{23}$H$_{25}$N$_6$O$_2$ (M+1) calcd. 417.2033. Found: 417.2038.

EXAMPLE 4

Amides of 5-Aminomethyl-6-aza-3-chloroindole were Prepared as Follows

Step A: 5-t-Butoxycarbonylaminomethyl-6-azaindole

A solution of 5-aminomethyl-6-azaindole (220 mg, 1.0 mmol), di-t-butyl dicarbonate (240 mg, 1.1 mmol), triethylamine (307 μL, 2.2 mmol) and DMAP (10 mg) in methylene chloride (5 mL) was stirred for 16 h. The mixture was evaporated in vacuo and the residue was purified by flash column chromatography (5% methanol/chloroform) to give the title compound:

$^1$H NMR (CD$_3$OD) δ 1.47 (s, 9H), 4.41 (s, 2H), 6.53 (d, J=2.2 Hz, 1H), 7.53 (obscured d, 1H), 7.53 (s, 1H), 8.61 (s, 1H).

Step B: 5-Aminomethyl-6-aza-3-chloroindole Dihydrochloride

A solution of 5-t-butoxycarbonylaminomethyl-6-azaindole (89 mg, 0.36 mmol) and NCS (53 mg, 0.4 mmol) in methylene chloride (4 mL) was stirred for 64 h. Methanol (25 mL) and 1 M HCl in ether (5 mL) were added and the mixture was stirred for a further 3 h. The reaction was evaporated in vacuo and the residue was triturated with ethyl acetate to give the title compound as a tan solid:

$^1$H NMR (CD$_3$OD) δ 4.54 (s, 2H), 8.12 (s, 1H), 8.22 (s, 1H), 9.12 (s, 1H).

Step C: 3-(2-Phenethylamino)-6-methyl-1-(5-methylcarboxaminomethyl-6-aza-3-chloroindolyl)-pyrazinone bis-TFA Salt

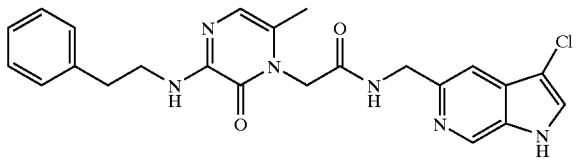

The title compound was prepared using standard procedures from 3-(2-phenethylamino)-6-methyl-1-carboxymethylpyrazinone and 5-aminomethyl-6-aza-3-chloroindole dihydrochloride.

HRMS (FAB) C$_{23}$H$_{24}$N$_6$O$_2$Cl (M+1) calcd. 451.1644. Found: 451.1648.

EXAMPLE 5

Amides of 5-Aminomethyl-4-aza-indole were Prepared as Follows

Step A: 5-Aminomethyl-4-aza-indole Dihydrochloride

The title compound was prepared from 2-cyano-6-methyl-5-nitropyridine (J. Med. Chem. 21, 194, 1978) using the procedures of Example 3, Steps C–D.

Step B: 3-(2-Phenethylamino)-6-methyl-1-(5-methylcarboxamidomethyl-4-azaindolyl)-pyrazinone bis-TFA Salt

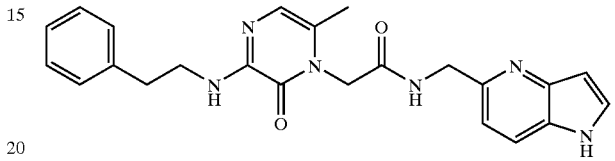

The title compound was prepared using standard procedures from 3-(2-phenethylamino)-6-methyl-1-carboxymethylpyrazinone and 5-aminomethyl-4-azaindole dihydrochloride.

HRMS (FAB) C$_{23}$H$_{25}$N$_6$O$_2$ (M+1) calcd. 417.2033. Found: 417.2037.

EXAMPLE 6

Preparation of 3-(2-phenethylamino)-6-methyl-1-(5-methylcarboxamido-methyl-7-aza-4-methylindolyl)-pyrazinone Dihydrochloride

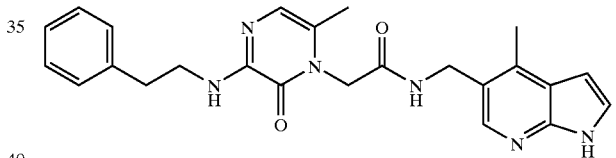

Step A: 2-(Pent-4-ynylamino)pyrimidine

A mixture of 2-chloropyrimidine (4.0 g, 35 mmol), 5-aminopent-2-yne (10.5 g, 88 mmol), triethylamine (12.3 mL, 88 mmol) in ethanol (50 mL) was heated in a sealed tube at 90° C. for 16 h. The mixture was cooled and evaporated in vaciio. The residue was taken up in ethyl acetate and was filtered through a plug of silica gel, eluting with ethyl acetate, and evaporated in vacuo to give the title compound:

$^1$H NMR (CDCl$_3$) δ 1.77 (t, J=2.7 Hz, 3H), 2.44 (m, 2H), 3.53, (q, J=6.3 Hz, 2H) 5.44 (br s, 1H), 6.53 (t, J=4.9 Hz, 1H), 8.27 (d, J=4.9 Hz, 2H).

Step B: 2-(N-Acetyl-N-pent-4-ynylamino)pyrimidine

A mixture of 2-(pent-4-ynylamino)pyrimidine (4.25 g, 26.4 mmol) and concentrated sulfuric acid (5 drops) in acetic anhydride (100 mL) was heated to 90° C. for 16 h. The mixture was cooled and partitioned between water and methylene chloride. The organic layer was dried (Na$_2$SO$_4$), filtered through a pad of silica and evaporated in vacuo to give the title compound:

$^1$H NMR (CDCl$_3$) δ 1.67 (t, J=2.6 Hz, 3H), 2.42 (s, 3H), 2.50 (m, 2H), 4.22, (t, J=7.4 Hz, 2H), 7.04 (t, J=4.8 Hz, 1H), 8.65 (d, J=4.8 Hz, 2H).

Step C: N-Acetyl-4-methyl-7-azaindoline

A solution of 2-(N-acetyl-N-pent-4-ynylamino) pyrimidine (3.49 g, 17.2 mmol) in nitrobenzene (35 mL) was heated under argon at 180° C. for 2 days. The reaction mixture was cooled and loaded directly onto a dry silica gel column. The column was first eluted with methylene chloride to wash off the nitrobenzene and then was eluted with ether to give after evaporation in vacuo to give the title compound as a pale yellow solid:

$^1$H NMR (CDCl$_3$) δ 2.24 (s, 3H), 2.68 (s, 3H), 2.97 (t, 2H), 4.11, (t, 2H), 6.72 (d, 1H), 8.00 (d, 1H).

Step D: 4-Methyl-7-azaindoline

Potassium hydroxide (1 M, 5 mL) was added to a stirred solution of N-acetyl-4-methyl-7-azaindoline (0.78 g, 4.75 mmol) in methanol (10 mL) and the resulting mixture was heated to 55° C. for 4 h. The mixture was cooled and partitioned between methylene chloride and dilute ammonium hydroxide solution. The organic layer was dried (Na$_2$SO$_4$) and evaporated in vacuo to give the title compound as a yellow solid:

$^1$H NMR (CDCl$_3$) δ 2.16 (s, 3H), 3.00 (t, J=8.4 Hz, 2H), 3.61, (m, 2H), 4.37 (br s 1H), 6.35 (d, J=5.4 Hz, 1H), 8.00 (d, J=5.4 Hz, 1H).

Step E: 5-Bromo-4-methyl-7-azaindoline

The title compound was prepared from 4-methyl-7-azaindoline using the procedures of Example 2, Step A:

$^1$H NMR (CDCl$_3$) δ 2.22 (s, 3H), 3.05 (t, J=8.5 Hz, 2H), 3.65 (t, J=8.5 Hz, 2H), 4.42 (br s, 1H), 7.27 (obscured s, 1H), 7.88 (s, 1H).

Step F: 5-Cyano-4-methyl-7-azaindoline

A stirred mixture of 5-bromo-4-methyl-7-azaindoline (270 mg, 1.27 mmol) and copper (I) cyanide (135 mg, 1.5 mmol) in DMF (0.3 mL) was heated to 180° C. for 4 h. The reaction mixture was cooled and partitioned between 5% potassium cyanide solution and ethyl acetate. The organic layer was dried (Na$_2$SO$_4$) and evaporated in vacuo. The residue was purified by flash column chromatography (50% ethyl acetate/hexanes) to give the title compound:

$^1$H NMR (CDCl$_3$) δ 2.30 (s, 3H), 3.07 (t, J=8.5 Hz, 2H), 3.75 (t, J=8.5 Hz, 2H), 4.93 (br s, 1H), 7.27 (obscured s, 1H), 8.10 (s, 1H).

Step G: 5-Cyano-4-methyl-7-azaindole

A mixture of 5-cyano-4-methyl-7-azaindoline (52 mg, 0.33 mmol) and manganese dioxide (130 mg, 1.5 mmol) in chloroform (10 mL) was stirred for 16 h and then was filtered through celite, washing through with chloroform followed by methanol. The filtrate was evaporated in vacuo to give the title compound as a tan solid:

$^1$H NMR (CDCl$_3$) δ 2.78 (s, 3H), 6.65 (dd, J=3.4 and 2.1 Hz, 1H), 7.41 (d, J=3.4 Hz, 1H), 8.51 (s, 1H), 8.97 (br s, 1H).

Step H: 5-Aminomethyl-4-methyl-7-azaindole Dihydrochloride

A suspension of 5-cyano-4-methyl-7-azaindole (48 mg, 0.31 mmol) and 10% palladium on carbon (25 mg) in methanol (10 mL) and concentrated HCl (0.5 mL) was shaken on a Parr apparatus under hydrogen (50 psi) for 6 h. The mixture was filtered through celite and evaporated in vacuo. The residue was dissolved in a minimum volume of methanol, ether was added and the solids collected by filtration to give the title compound as a pale yellow solid:

$^1$H NMR (CD$_3$OD) δ 2.84 (s, 3H), 4.43 (s, 2H), 6.93 (d, J=3.5 Hz, 1H), 7.64 (d, J=3.5 Hz, 1H), 8.45 (br s, 1H).

Step 1: 3-(2-Phenethylamino)-6-methyl-1-(5-methylcarboxamidomethyl-7-aza-4-methylindolyl)-pyrazinone bis-TFA Salt The title compound was prepared using standard procedures from 3-(2-phenethylamino)-6-methyl-1-carboxymethylpyrazinone and 5-aminomethyl-7-aza-4-methylindole dihydrochloride.

HRMS (FAB) C$_{24}$H$_{27}$N$_6$O$_2$ (M+1) calcd. 431.2190. Found: 431.2202.

EXAMPLE 7

Preparation of 3-(2-Phenethylamino)-6-methyl-1-(5-methylcarboxamido-methyl-1,2,3-benzotriazolyl)-pyrazinone

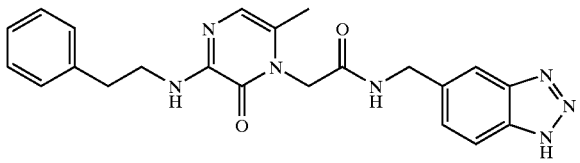

Step A: 5-Azidomethyl-1,2,3-benzotriazole

To a solution of 5-chloromethyl-1,2,3-benzotriazole (2.2 g, 12.2 mmol, Katritzky et al. *Synth. Commun*. 1993, 23, 2019) dissolved in DMF (25 mL) was added sodium azide (2.4 g, 36.5 mmol). The resulting mixture was stirred under Ar for 16 h and the precipitated product was filtered and air dried to afford the title compound:

$^1$H NMR (DMSO, 400 MHz) δ 7.75 (d, 2H), 7.18 (d, 1H), 4.52 (s, 2H).

Step B: 5-Aminomethyl-1,2,3-benzotriazole Hydrochloride

To a solution of 5-azidomethyl-1,2,3-benzotriazole (730 mg, 4.56 mmol) in THF (7 mL) was added water (123 mL, 6.8 mmol) and triphenylphosphine (314 mg, 5.47 mmol). The resulting mixture was stirred under Ar for 16 h. The solution was concentrated in vacuo, diluted with ethyl acetate (20 mL) and extracted with 0.1N HCl (3×5 mL). The aqueous phase was removed in vacio to give the title compound:

$^1$H NMR (D$_2$O, 400 MHz) δ 7.95 (m, 2H), 7.36 (d, 1H), 4.30 (s, 1H).

Step C: 3-(2-Phenethylamino)-6-methyl-1-(5-methylcarboxamidomethyl-1,2,3-benzotriazolyl)-pyrazinone To a solution of 3-(2-phenethylamino)-6-methyl-1-carboxymethylpyrazinone (532 mg, 1.85 mmol) in of DMF (1 mL) was added 5-aminomethyl-1,2,3-benzotriazole hydrochloride (300 mg, 1.85 mmol), EDC (355 mg, 1.85 mmol), HOBT (250 mg, 1.85 mmol) and N-methylmorpholine (406 µL, 3.7 mmol). The resulting mixture was stirred for 16 h then was filtered to give the title compound as a white solid:

$^1$H NMR (DMSO, 400 MHz) δ 8.81 (br, 1H), 7.75 (br, 1H), 7.25 (m, 8H), 6.83 (br, 1H), 6.65 (s, 1H), 4.66 (s, 2H), 4.46 (s, 2H), 3.49 (t, 2H), 3.31 (t, 2H), 2.850 (s, 3H). LRMS=418 (M+1).

EXAMPLE 8

Amides of 3-Amino-5-aminomethyl-7-azaindazole were Prepared as Follows

Step A: 2-Amino-3,5-dicyanopydridine

A mixture of 2-amino-6-chloro-3,5-dicyanopyridine (*Synth. Comm*. 1993, 2605, 15.0 g, 84 mmol) and 10% palladium on carbon (10.0 g) in dioxane (150 mL) was shaken on a Parr apparatus under hydrogen (55 psi) for 16 h. More catalyst (7.5 g) was added and after a further 4 h the reaction mixture was filtered through celite washing through with ethanol and evaporated in vacuo. The residue was partitioned between methylene chloride and 1 M HCl. The insoluble material was collected by filtration and dried to give the title compound. The methylene chloride layer was washed with brine, dried (Na$_2$SO$_4$) and evaporated in vacuo to give additional product:

$^1$H NMR (DMSO) δ 7.93 (br s, 2H), 8.41 (d, J=2.2 Hz, 1H), 8.56 (d, J=2.2 Hz, 1H).

Step B: 2-Chloro-3,5-dicyanopyridine

Acetic acid (37 mL) was added over 10 min to sodium nitrite (13.4 g, 0.194 mol) with stirring. Concentrated sulfuric acid (12.3 mL) was added over 5 min to the resulting thick slurry which was then cooled to 0° C. In a separate flask, pyridinium hydrochloride (14.4 g, 0.125 mol) was added to a stirred mixture of 2-amino-3,5-dicyanopyridine (4.0 g, 27.75 mmol) in acetic acid (55 mL) and the resulting mixture was cooled to 0° C. to give a thick slurry. The nitrite slurry was added to the aminopyridine slurry over 5 min with stirring at 0° C. Acetic acid (50 mL) was added and the thick slurry was warmed to rt. After 1 h at rt the mixture was warmed to 50° C. and after a further 1 h, it was poured into an ice/water mixture (500 mL). The aqueous mixture was extracted with methylene chloride (4 times) and the. combined extracts were dried ($Na_2SO_4$) and evaporated to a yellow solid. The crude product was purified by chromatography on silica (chloroform/methanol gradient, 1–3% methanol) to give the title compound as a solid:

$^1$H NMR ($CDCl_3$) δ 8.34 (d, J=2.2 Hz, 1H), 8.88 (d, J=2.2 Hz, 1H).

Step C: 5-Cyano-3-amino-7-azaindole

Hydrazine hydrate (55%, 125 mL, 2.20 mmol) was added to a stirred suspension of 2-chloro-3,5-dicyanopyridine (240 mg, 1.47 mmol) and triethylamine (205 μL, 1.47 mmol) in ethanol (3 mL) and the resulting red mixture was heated to 60° C. After 16 h the mixture was cooled and filtered to give the title compound:

$^1$H NMR (DMSO) δ 5.94 (s, 2H), 8.61 (d, J=1.8 Hz, 1H), 8.66 (d, J=1.8 Hz, 1H), 12.63 (s, 1H).

Step D: 5-Aminomethyl-3-amino-7-azaindazole Hydrochloride

The title compound was prepared from 5-cyano-3-amino-7-azaindazole using the procedures of Example 2, Step C, as a red solid:

LRMS=163.2 (M)$^+$.

Step E: 3-(2-Phenethylamino)-6-methyl-1-(5-methylcarboxamidomethyl-3-amino-7-azaindazolyl)-pyrazinone

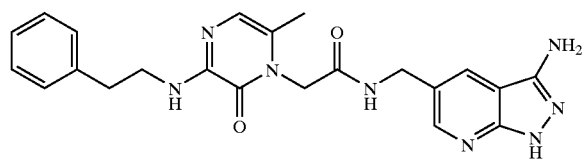

The title compound was prepared using standard procedures from 3-(2-phenethylamino)-6-methyl-1-carboxymethylpyrazinone and 5-aminomethyl-3-amino-7-azaindazole hydrochloride:

LRMS=433.2 (M+1).

EXAMPLE 9

Amides of 3-amino-5-aminomethylindazole were Prepared a Follows

Step A: 3-Amino-5-aminomethylindazole

The title compound was prepared from 2,4-dibromofluorobenzene using the procedures of Example 2, Step B followed by Example 8, Steps C, and D.

Step B: 3-(2-Phenethylamino)-6-methyl-1-(3-amino-5-methylcarbox-amidomethylindazolyl)-pyrazinone bis-TFA Salt

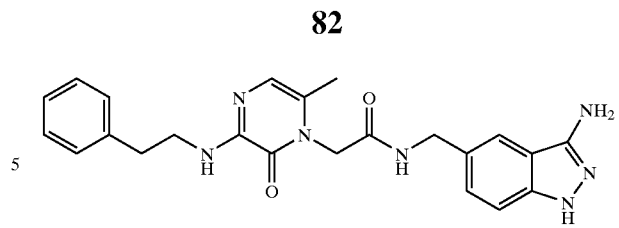

The title compound was prepared using standard procedures from 3-(2-phenethylamino)-6-methyl-1-carboxymethylpyrazinone and 5-aminomethyl-3-aminoindazole hydrochloride:

HRMS (FAB) $C_{23}H_{26}N_7O_2$ (M+1) calcd. 432.2142. Found: 432.2119.

EXAMPLE 10

Amides of 5-(Aminomethyl)benzimidazole were Prepared as Follows

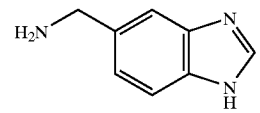

Step A: Ethyl-5-benzimidazole Carboxylate

To a stirred solution of benzimidazole-5-carboxylic acid (Aldrich, 10 g, 61.7 mmol) in EtOH (200 mL) was added dropwise conc. $H_2SO_4$ (8 mL), and the solution was heated to reflux. After 1 h the solution was cooled to 60° C. and stirred for 16 h. The solution was then concentrated in vacuo and the residue was partitioned between EtOAc and saturated $Na_2CO_3$ solution. The layers were separated and the aqueous layer was extracted with EtOAc. The combined organic layers were washed with brine, dried ($Na_2SO_4$), and concentrated in vacuo to afford the title compound as a brown solid:

$^1$H NMR (400 MHz, $CDCl_3$): δ 1.42 (t, J=7.1 Hz, 3H), 4.41 (q, J=7.1 Hz, 2H), 7.68 (d, J=8.4 Hz, 1H), 8.04 (dd, J=8.5 Hz, J=1.5 Hz, 1H), 8.23 (s, 1H), 8.43 (s, 1H); HRMS (FAB) $C_{10}H_{11}N_2O_2$ calcd. 191.2096 (M+1). Found 191.0541.

Step B: 5-(Hydroxymethyl)-benzimidazole

To a cooled (0° C.) suspension of ethyl-benzimidazole-5-carboxylate (4.76 g, 25 mmol) in $CH_2Cl_2$ (100 mL) was added a 1 M solution of DIBAL in $CH_2Cl_2$ (100 mL) and the mixture was stirred for 4 h. The reaction was quenched by the sequential addition of MeOH (8 mL), 1 M NaOH (16 mL), and 30% sodium potassium tartrate (40 mL). The mixture was warmed to RT and filtered, and the solid residue was washed with $CH_2Cl_2$. The filtrate was concentrated in vacuo to afford the title compound as a brown solid:

$^1$H NMR (400 MHz, DMSO-d6): δ 4.58 (s, 1H), 7.14 (m, 1H), 7.46 (s, 1H), 7.51 (m, 1H), 8.15 (s, 1H); HRMS (FAB) $C_8H_9N_2O$ calcd. 149.1723 (M+1). Found 149.1045.

Step C: 5-(Azidomethyl)-benzimidazole

To a cooled (0° C.) suspension of 5-(hydroxymethyl)-benzimidazole (920 mg, 6.2 mmol) in THF (12 mL) was added sequentially DPPA (1.46 mL, 6.8 mmol) and DBU (1.11 mL, 7.4 mmol). The resulting solution was heated to reflux for 5 h, cooled to RT, and concentrated in vacuo. The residue was partitioned between sodium bicarbonate and ethyl acetate. The organic layer was washed with brine, dried ($Na_2SO_4$), and concentrated in vacuo. Silica gel chromatography (15% MeOH—$CHCl_3$), afforded the title compound as a brown solid:

$R_f$(8:1:1 EtOAc-MeOH—$NH_4OH$)=0.31; m.p. 110–114° C.; $^1$H NMR (400 MHz, DMSO-d6): δ 8.25 (s, 1H), 7.27 (d,

J=8.4, 1H), 7.62–7.60 (m, 2H), 7.20 (d, J=8.2 Hz, 1H), 8.24 (s, 1H); HRMS (FAB) C$_8$H$_8$N$_5$ calcd. 174.1847 (M+1). Found 174.1222.

Step D: 5-(Aminomethyl)-benzimidazole Dihydrochloride

To a stirred solution of 5-(azidomethyl)benzimidazole (990 mg, 5.8 mmol) in THF (50 mL), was added Ph$_3$P (3.04 g, 11.6 mmol) followed by H$_2$O (99 μL) and the solution allowed to stir at RT for 16 h. The solution was concentrated in vacuo and EtOAc was added to the residue. The mixture was warmed gently until the solids dissolved. A saturated solution of HCl in EtOAc was added dropwise until precipitation began. The suspension was stirred for a few minutes to allow for complete precipitation and was filtered to afford the title compound as a white solid:

$^1$H NMR (400 MHz, DMSO-d6): δ 4.08 (s, 2H), 7.27 (d, J=8.4, 1H), 7.60 (d, J=6.2, 1H), 7.70 (s, 1H), 8.24 (s, 1H).

EXAMPLE 11

Amides of 5-(Aminomethyl)-2-methylbenzimidazole were Prepared as Follows

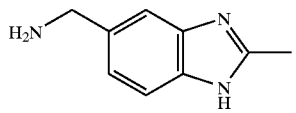

Step A: Ethyl-(2-methyl-5-benzimidazole)-carboxylate

The title compound was prepared from 2-methyl-5-benzimidazole carboxylic acid (Acros) according to the procedure of Example 10, Step A:

R$_f$(10% MeOH—CHCl$_3$)=0.31. $^1$H NMR (300 MHz, CD$_3$OD): δ (8.18, br s, 1H), 7.91 (dd, J=1.5, 8.4 Hz, 1H), 7.54 (br m, 1H), 4.38 (q, J=7.5 Hz, 2H), 2.60 (s, 3H), 1.41 (t, J=7.2 Hz, 3H).

Step B: 5-(Hydroxymethyl)-2-methylbenzimidazole

To a stirred suspension of LAH (397 mg, 10.5 mmol) in dry THF (100 mL) at 0° C. was added in portions ethyl-[2-methylbenzimidazole-5]-carboxylate (1.0.1 g, 4.95 mmol). After 1 h an additional 1.19 g of LAH was added and the mixture was allowed to come to room temperature. After 1 h the mixture was cooled to 0° C. and quenched by the sequential addition of H$_2$O (1.6 mL), 3N NaOH (1.6 mL) and H$_2$O (4.8 mL). The mixture was diluted with EtOAc (125 mL) and stirred at room temperature for 10–15 min until a fine gray suspension was obtained. This suspension was filtered through a small pad of Celite. The filtrate was dried (MgSO$_4$) and concentrated to afford the title compound as a white solid:

R$_f$(8:1:1 EtOAc:NH$_4$OH:MeOH)=0.43. $^1$H NMR (400 MHz, CD$_3$OD): δ 7.47 (s, 1H), 7.43(d, J=8.4 Hz, 1H), 7.19 (d, J=8.4 Hz, 1H), 4.68(s, 2H), 2.55 (s, 3H).

Step C: 5-(Aminomethyl)-2-methylbenzimidazole

The title compound was prepared from 5-(hydroxymethyl)-2-methylbenzimidazole according to the procedures of Example 14, Steps C and D:

R$_f$(8:1:1 EtOAc:MeOH:NH$_4$OH)=0.15. $^1$H NMR (300 MHz, CD$_3$OD): δ 7.45 (m, 2H), 7.20 (d, J=8.1 Hz, 1H), 3.90 (s, 2H), 2.56 (s, 3H).

Step D: 3-(2,2-Difluoro-2-phenethylamino)-6-methyl-1-(2-methyl-5-methylcarboxamidomethylbenzimidazolyl)-pyrazinone Bistrifluoroacetate

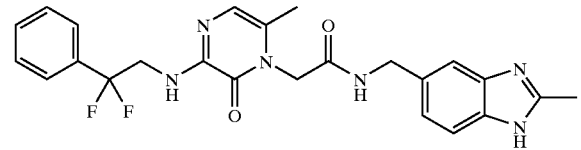

The title compound was prepared from 5-aminomethyl-2-methylbenzimidazole using standard procedures:

$^1$H NMR (400 MHz, CD$_3$OD): δ 8.97 (s, 1H), 7.48–7.69 (m, 8H), 6.66 (d, J=0.8 Hz, 1H), 4.82 (s, 2H), 4.60 (d, J=4.0 Hz, 2H), 4.15 (t, J=14.6 Hz, 2H), 2.84 (s, 3H), 2.20 (s, 3H); HRMS (FAB) C$_{24}$H$_{25}$F$_2$N$_6$O$_2$ calcd. 467.2001 (M+1). Found 467.2013.

EXAMPLE 12

Amides of 5-(Aminomethyl)-1-trityl-7-azabenzimidazole were Prepared as Follows

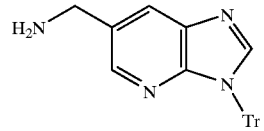

Step A: 5,6-Diaminonicotinic Acid

See Markwald, W. Chem. Ber. 1984, 27, 1317. To a stirred solution of SnCl$_2$ (4.16 g, 22.0 mmol) in concentrated HCl (11 mL) at 0° C. was added in portions 5-nitro-6-aminonicotinic acid (1.01 g, 5.5 mmol). The resulting orange mixture was then heated to 100° C. under argon for 75 min. The mixture was then cooled to RT and was then placed in an ice bath and neutralized with concentrated aqueous ammonia (to pH 6–7), resulting in a thick cream-colored mixture. The mixture was then acidified to pH 4 with acetic acid and the precipitate collected by filtration, washed with H$_2$O and dried under vacuum overnight to afford the title compound:

$^1$H NMR (300 MHz, DMSO-d6): δ 7.98 (d, J=2.1 Hz, 1H), 7.21 (d, J=2.1 Hz, 1H), 6.24 (br s, 2H), 5.00 (br s, 2H).

Step B: Methyl-5,6-diaminonicotinate

A solution of 5,6-diaminonicotinic acid (5.5 mmol) in saturated methanolic HCl was heated to reflux for 3 h. The yellow solution was cooled to RT and treated with solid sodium carbonate until basic (pH 9). The mixture was filtered through Celite and the filter cake was rinsed well with methanol. The filtrate was concentrated to an oily green solid. Silica gel chromatography (16:1:1 EtOAc-MeOH—NH$_4$OH) afforded the title compound as a pale pink solid:

R$_f$(8:1:1 EtOAc-MeOH—NH$_4$OH)=0.54; $^1$H NMR (400 MHz, DMSO-d6): δ 7.94 (d, J=2.0 Hz, 1H), 7.15 (d, J=2.0 Hz, 1H), 6.24 (s, 2H), 4.90 (s, 2H), 3.73 (s, 3H).

Step C: Methyl-7-azabenzimidazole-5-carboxylate

A mixture of methyl-5,6-diaminonicotinate (461 mg, 2.76 mmol), formic acid (250 μL) and triethyl orthoformate (7.5 mL) was heated to 100° C. for 2 h. The mixture was then concentrated to an oily solid. Silica gel chromatography (8:1:1 EtOAc-MeOH—NH$_4$OH) afforded the title compound as a cream-colored solid:

R$_f$(8:1:1 EtOAc-MeOH—NH$_4$OH)=0.22; $^1$H NMR (400 MHz, DMSO-d6): δ 8.94 (d, J=2.0 Hz, 1H), 8.64 (s, 1H), 8.50 (d, J=2.0 Hz, 1H), 3.91 (s, 3H).

Step D: Methyl-(1-trityl-7-azabenzimidazole)-5-carboxylate

To a stirred suspension of methyl-7-azabenzimidazole-5-carboxylate (410 mg, 2.32 mmol) in $CH_2Cl_2$ (6.5 mL) was added $Et_3N$ (646 μL, 4.63 mmol) and triphenylmethyl chloride (Aldrich, 775 mg, 2.78 mmol). The mixture was stirred at RT for 16 h and was then partitioned between $CH_2Cl_2$ and $H_2O$. The layers were separated and the aqueous layer was extracted once with $CH_2Cl_2$. The combined organic layers were washed with brine, dried ($Na_2SO_4$) and concentrated to an oily solid. Silica gel chromatography (gradient elution with hexanes, 25% EtOAc-hexanes, 50% EtOAc-hexanes and finally 10% MeOH—$CH_2Cl_2$) afforded the title compound as a white foam:

$R_f$(1:1 hexanes-EtOAc)=0.12; [1] H NMR (400 MHz, $CD_3OD$): δ 8.99 (d, J=1.6 Hz, 1H), 8.40 (s, 1H), 7.47 (d, J=1.6 Hz, 1H), 7.41–7.39 (m, 9H), 7.23–7.21 (m, 6H), 3.80 (s, 3H).

Step E: 5-Aminomethyl-1-trityl-7-azabenzimidazole

The title compound was prepared from methyl-(1-trityl-7-azabenzimidazole)-5-carboxylate (530 mg, 1.26 mmol) according to the procedures of Example 11, Step B, and Example 10, Steps C and D:

$^1$H NMR (300 MHz, $CDCl_3$): δ 8.42 (d, J=2.1 Hz, 1H), 8.12 (s, 1H),), 7.35–7.32 (m, 9H), 7.18–7.15 (m, 6H), 6.66 (d, J=1.8 Hz, 1H), 3.71 (s, 2H).

Step G: 3-(2-Phenethylamino)-6-methyl-1-(5-methylcarboxamidomethyl-7-azabenzimidazolyl)-pyrazinone Bistrifluoroacetate

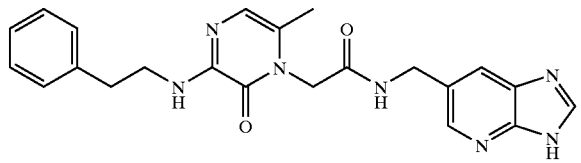

EDC coupling using standard procedures of 3-(2-phenethylamino)-6-methyl-1-methylenecarboxypyrazinone and 5-aminomethyl-1-trityl-7-azabenzimidazole afforded the trityl-protected title compound as an oily solid. The crude product (0.067 mmol) was dissolved in $CH_2Cl_2$ (4.9 mL) and treated with TFA (2.4 mL) dropwise. The resulting bright yellow solution was stirred at RT for 30 min, and was then treated with triethylsilane dropwise until the color was discharged (8–10 drops). The mixture was stirred at RT for 16 h and was then concentrated to a yellow oily solid. Purification by HPLC (40 min gradient elution 95:5 to 20:80 $H_2O/0.1\%$ TFA:$CH_3CN$) afforded the title compound as an oil:

$^1$H NMR (400 MHz, $CD_3OD$): δ 9.01 (t, J=4.0 Hz, 1H), 8.79 (s, 1H), 8.51 (d, J=1.6 Hz, 1H), 8.17 (m, 1H), 7.32–7.20 (m, 5H), 6.55 (s, 1H), 4.79 (s, 2H), 4.63 (d, J=4.0 Hz, 2H), 3.67 (t, J=7.4 Hz, 2H), 2.99 (t, J=7.6 Hz, 2H), 2.18 (s, 3H) MS (ES) $C_{22}H_{24}N_7O_2$ calcd. 418.42 (M+1). Found 418.20.

EXAMPLE 13

Amides of 5-(Aminomethyl)-1-trityl-6-azabenzimidazole were Prepared as Follows

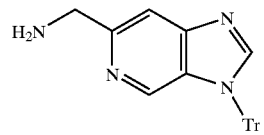

Step A: Methyl-6-azabenzimidazole-5-carboxylate

See Guzman, F. et al. *J. Med. Chem.* 1984, 27, 564. To a stirred solution of methyl-4,5,6,7-tetrahydro-6-azabenzimidazole-5-carboxylate (886 mg, 4.89 mmol) in acetic acid (15 mL) was added $SeO_2$ (2.17 g, 19.6 mmol). The reaction was stirred at 90° C. under inert atmosphere for 15 h. The mixture was then cooled and filtered through a Celite pad. The filter cake was washed with methanol. The filtrate was evaporated in vacuo to afford a solid. Silica gel chromatography eluting with 8:1:1 EtOAc:MeOH: $NH_4OH$ afforded the light yellow solid:

$^1$H NMR (300 MHz, $CD_3OD$): δ 9.00 (d, J=0.9 Hz, 1H), 8.54 (s, 1H), 8.46 (d, J=0.9 Hz, 1H), 4.01 (s, 3H).

Step B: 5-Aminomethyl-1-trityl-6-azabenzimidazole

The title compound was prepared from methyl-6-azabenzimidazole-5-carboxylate according to procedures of Example 12, Steps D and E:

$^1$H NMR (400 MHz, $CDCl_3$): δ 8.01 (s, 1H), 7.75 (d, J=0.8 Hz, 1H), 7.64 (s, 1H), 7.16–7.36 (m, 15H), 4.02 (s, 2H), 2.00 (br s, 2H).

Step C: 3-(2-Phenethylamino)-6-methyl-1-(5-methylcarboxamidomethyl-6-azabenzimidazolyl)pyrazinone Bistrifluoroacetate

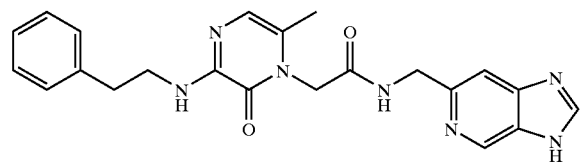

The title compound was prepared from 5-aminomethyl-1-trityl-6-azabenzimidazole using the procedures of Example 12, Step F:

$^1$H NMR (400 MHz, $CD_3OD$): δ 9.24 (d, J=0.8, 1H), 8.81 (s, 1H), 8.13 (s, 1H), 7.27–7.29 (m, 5H), 6.57 (d, J=0.8 Hz, 1H), 4.86 (s, 2H), 3.68 (t, J=7.4 Hz, 2H), 3.00 (t, J=7.4 Hz, 2H), 2.21 (d, J=0.8 Hz, 3H); HRMS (FAB) $C_{22}H_{24}N_7O_2$ calcd. 418.1986 (M+1). Found 418.1987.

EXAMPLE 14

Preparation of 3-(2-Phenethylamino)-6-methyl-1-(6-methyl-5-methylcarboxamidomethyl-7-azabenzotriazolyl)-pyrazinone Dihydrochloride

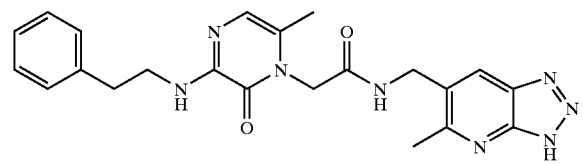

Step A: 2-Amino-6-methyl-5-(phyhtalimidomethy)pyridine

To a stirred solution of $Na_2CO_3$ (7.57 g, 71.4 mmol) and 2-amino-5-(aminomethyl)-6-methylpyridine bis-hydrochloride (5.00 g, 23.8 mmol) in water (200 mL) was added carbethoxyphthalimide (5.74 g, 26.2 mmol). The grainy mixture was stirred for 45 min. during which time the consistency became milky. The suspension was filtered and washed with water to afford the title compound as an off-white solid.

$^1$H NMR (400 MHz,DMSO-d6): δ 7.86–7.81 (m, 4H), 7.20 (d, J=8.4 Hz, 1H), 6.20 (d, J=8.4 Hz, 1H), 5.75 (br s, 2H), 4.58 (s, 2H), 2.34 (s, 3H).

Step B: 2-Amino-6-methyl-3-nitro-5-(phthalimidomethyl) pyridine

To a stirred solution of 2-amino-6-methyl-5-(phthalimidomethyl)pyridine (3.00 g, 11.2 mmol) in $H_2SO_4$ (17 mL) at 0° C. was added $HNO_3$ (583 μL) dropwise. The solution was stirred for 1 h at 0° C. and was then warmed to room temperature at which it was stirred for an additional 3 h. The reaction was diluted with water and neutralized with solid $Na_2CO_3$. The resulting orange precipitate was filtered and washed with water. Silica gel chromatography (gradient 3% MeOH/CHCl3 to 4% MeOH/CHCl$_3$) afforded the title compound as a bright yellow solid.

$^1$H NMR (300 MHz, CDCl$_3$): δ 8.41 (s, 1H), 7.90–7.87 (m, 2H), 7.77–7.74 (m, 2H), 4.80 (s, 2H), 2.62 (s, 3H).

Step C: 2-Amino-5-(aminomethyl)-6-methyl-3-nitropyridine Hydrochloride

To a stirred solution of 2-amino-6-methyl-3-nitro-5-(phthalimidomethyl)pyridine (1.28 g, 4.11 mmol) in EtOH (12 mL) was added hydrazine hydrate (200 μL, 4.11 mmol). The mixture was stirred at reflux for 1 h. The reaction was cooled followed by addition of 12N HCl (342 μL, 4.11 mmol). EtOH was evaporated in vacuo to give a thick residue. The residue was taken up in $^1$M HCl and heated for 10 min at 50° C. after which it was cooled, filtered, and washed with 1 M HCl. The filtrate was washed twice with $CH_2Cl_2$ and evaporated in vacuo azeotroping with a toluene/EtOH mixture. The off-white solid was dried under high vacuum.

$^1$H NMR (300 MHz,CD$_3$OD): δ 8.97 (s, 1H), 4.20 (s, 2H), 2.71 (s, 3H).

Step D: 3-(2-Phenethylamino)-6-methyl-1-(2-amino-6-methyl-5-methylcarboxamidomethyl-3-nitropyridyl)-4-pyrazin-2-one Dihydrochloride The title compound was prepared using standard procedures.

Step E: 3-(2-Phenethylamino)-6-methyl-1-(2,3-diamino-6-methyl-5-methylcarboxamidomethylpyridyl)-4-pyrazin-2-one:

To a flask charged with 10% Pd/C (130 mg) under inert atmosphere was added degassed EtOH (8 mL) and 3-(2-phenethylamino)-6-methyl-1-(2-amino-6-methyl-5-methylcarboxamidomethyl-3-nitropyridyl)-4-pyrazin-2-one (128 mg, 0.245 mmol). The reaction was placed under 1 atm of H$_2$ (balloon) and the reaction was stirred for 4 h. The mixture was thoroughly degassed and filtered through a pad of celite washing with EtOH. The filtrate was evaporated in vacuo to afford the title compound as a white solid:

$^1$H NMR (400 MHz, CD$_3$OD): δ 8.79 (m, 1H), 7.33–7.22 (m, 5H), 6.57 (s, 1H), 4.75 (s, 2H), 4.27 (m, 2H), 3.67 (t, J=7.5 Hz, 2H), 2.99 (t, J=7.4 Hz, 2H), 2.41 (s, 3H), (2.18 (s, 3H).

Step F: 3-(2-Phenethylamino)-6-methyl-1-(6-methyl-5-methyl Carboxamidomethyl-7-azabenzotriazolyl)-perazinone Dihydrochloride To a stirred solution of 3-(2-phenethylamino)-6-methyl-1-(2,3-diamino-6-methyl-5-methylcarboxamidomethylpyridyl)-pyrazinone (38.4 mg, 0.078 mmol) in 1 M hydrochloric acid (780 μL) at 0° C. was added sodium nitrate (5.4 mg, 0.078 mmol). The reaction was stirred at 0° C. for 1.5 h during which time a precipitate formed. The suspension was filtered and washed with water. The solid was collected and dried under high vacuum to afford the title compound as the bis-HCl salt:

$^1$H NMR (400 MHz,CD$_3$OD): δ 8.99 (s, 2H), 8.30 (s, 1H), 7.20–7.28 (m, 5H,), 6.55 (s, 1H), 4.76 (s, 2H), 4.62 (d, J=5.6 Hz, 2H), 3.68 (t, J=7.4 Hz, 2H), 3.01 (t, J=7.4 Hz, 2H), 2.72 (s, 3H), 2.23 (s, 3H); HRMS (FAB) $C_{22}H_{25}N_8O_2$ calcd. 433.2094 (M+1). Found 433.2096.

EXAMPLE 15

3-Amino-4-cyclobutylmethylsulfonyl-6-methyl-1-(3-amino-5-methylcarboxamidomethylindazolyl)-2-pyridinone Trifluoroacetate

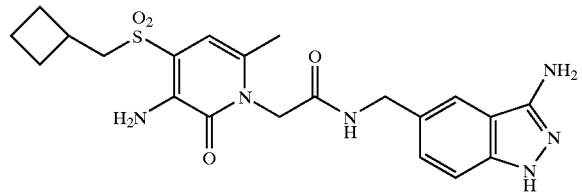

The title compound was prepared from 3-amino-5-aminomethylindazole using standard procedures:

$^1$H NMR (300 MHz, CD$_3$OD): δ 8.81 (s, 1H), 7.85 (s, 1H), 7.59–7.63 (m, 1H), 7.40–7.43 (m, 1H), 6.29 (s, 1H), 4.52 (d, J=5.7 Hz, 2H), 3.29 (d, J=6.4 Hz, 2H), 2.73–2.79 (m, 1H), 2.28 (s, 3H), 1.81–2.13 (m, 6H); HRMS (FAB) $C_{21}H_{27}N_6O_4S$ calcd. 459.1809 (M+1). Found 459.1806.

EXAMPLE 16

3-(2,2-Difluoro-2-phenethylamino)-6-methyl-1-(3-amino-5-methylcarboxamidomethylindazolyl)-pyrazinone Bistrifluoroacetate

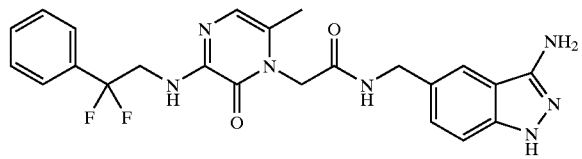

The title compound was prepared from 3-amino-5-aminomethylindazole using standard procedures:

$^1$H NMR (300 MHz, CD$_3$OD): δ 7.37–7.82 (m, 8H), 6.66 (d, J=1.0 Hz, 1H), 4.75 (s, 2H), 4.51 (d, J=3.7 Hz, 2H), 4.07 (t, J=14.6 Hz, 2H), 2.16 (s, 3H); HRMS (FAB) $C_{23}H_{24}N_7O_2F_2$ calcd. 468.1954 (M+1). Found 468.1953.

EXAMPLE 17

3-(2,2-Difluoro-2-phenethylamino)-6-methyl-1-(5-methylcarboxamidomethylbenzimidazolyl)-pyrazinone Dihydrochloride

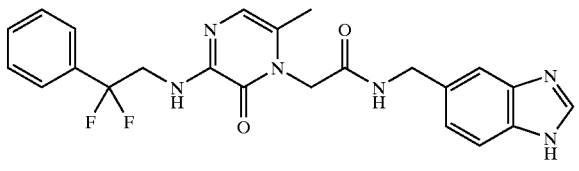

The title compound was prepared from 5-aminomethyl-benzimidazole using standard procedures:

$^1$H NMR (300 MHz, CD$_3$OD): δ 9.39 (s, 1H), 7.52–7.85 (m, 9H), 6.67 (d, J=1.0 Hz, 1H), 4.88 (s, 2H), 4.65 (d, J=3.9 Hz, 2H), 4.21 (t, J=14.8 Hz, 2H), 2.25 (s, 3H); HRMS (FAB) C$_{23}$H$_{23}$F$_2$N$_6$O$_2$ calcd. 453.1845 (M+1). Found 453.1857.

EXAMPLE 18

3-(2,2-Difluoro-2-phenethylamino)-6-methyl-1-(5-methylcarbox-amidomethyl-7-azabenzimidazolyl)-pyrazinone Bistrifluoroacetate

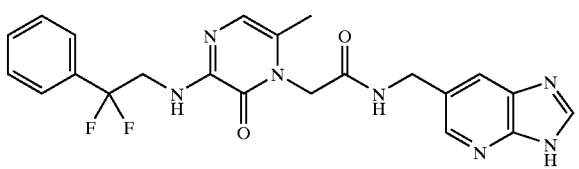

The title compound was prepared from 5-aminomethyl-7-azabenzimidazole using the procedures of Example 12, Step F:

$^1$H NMR (300 MHz, CD$_3$OD): δ 9.40 (s, 1H), 8.73 (d, J=1.5 Hz, 1H), 8.41 (s, 1H), 7.52–7.67 (m, 5H), 6.67 (s, 1H), 4.88 (s, 2H), 4.71 (s, 2H), 4.21 (t, J=14.7 Hz, 2H), 2.25 (s, 3H); HRMS (FAB) C$_{22}$H$_{22}$F$_2$N$_7$O$_2$ calcd. 454.1797 (M+1). Found 454.1790.

EXAMPLE 19

3-(2,2-Difluoro-2-pyridylethylamino)-6-methyl-1-(5-methylcarboxamido-methyl-7-azabenzimidazolyl)-pyrazinone Tristrifluoroacetate

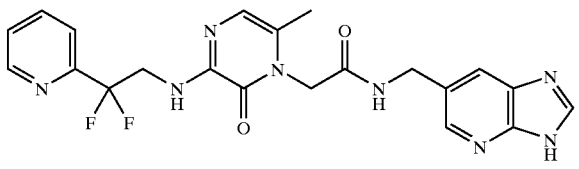

The title compound was prepared from 5-aminomethyl-7-azabenzimidazole using the procedures of Example 12, Step F:

$^1$H NMR (300 MHz, CD$_3$OD): δ 9.10 (s, 1H), 9.05 (m, 1H), 8.68 (m, 1H), 8.61 (s, 1H), 8.28 (s, 1H), 7.99 (m, 1H), 7.78 (m, 1H), 7.58 (m, 1H), 6.67 (s, 1H), 4.79 (s, 2H), 4.65 (m, 2H), 4.35 (t, J=14.1 Hz, 2H), 2.195 (s, 3H); HRMS (FAB) C$_{21}$H$_{21}$F$_2$N$_8$O$_2$ calcd. 455.1750 (M+1). Found 455.1734.

EXAMPLE 20

3-Amino-4-cyclobutylmethylsulfonyl-6-methyl-1-(5-methylcarbox-amidomethyl-7-azabenzimidazolyl)-2-pyridinone Trifluoroacetate

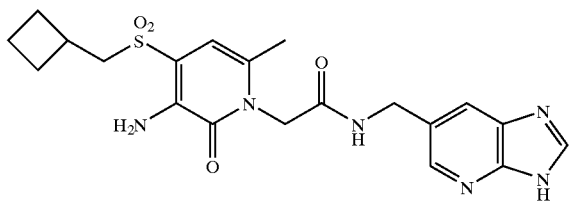

The title compound was prepared from 5-aminomethyl-7-azabenzimidazole using the procedures of Example 12, Step F:

$^1$H NMR (300 MHz, CD$_3$OD): δ 9.27 (s, 1H), 8.67 (d, J=2.1 Hz, 1H), 8.38 (d, J=1.8 Hz, 1H), 6.28 (d, J=0.9 Hz, 1H), 4.83 (s, 2H), 4.67 (s, 2H), 3.28 (d, J=7.5 Hz, 2H), 2.29 (s, 3H), 1.82–2.11 (m, 6H); HRMS (FAB) C$_{20}$H$_{25}$N$_6$O$_4$S calcd. 445.1652 (M+1). Found 445.1658.

EXAMPLE 21

3-Amino-4-cyclopropylmethylsulfonyl-6-methyl-1-(5-methylcarbox-amidomethyl-7-azabenzimidazolyl)-2-pyridinone Trifluoroacetate

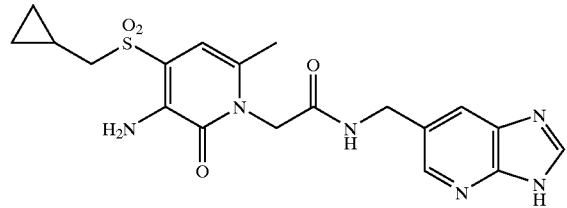

The title compound was prepared from 5-aminomethyl-7-azabenzimidazole using the procedures of Example 12, Step F:

$^1$H NMR (300 MHz, CD$_3$OD): δ 9.25 (s, 1H), 8.67 (d, J=1.8 Hz, 1H), 8.38 (s, 1H), 6.33 (s, 1H), 4.84 (s, 2H), 4.67 (s, 2H), 3.11 (d, J=7.2 Hz, 2H), 2.29 (s, 3H), 0.57–0.60 (m, 2H), 0.27–0.30 (m, 2H); HRMS (FAB) C$_{19}$H$_{23}$N$_6$O$_4$S calcd. 431.1496 (M+1). Found 431.1487.

EXAMPLE 22

3-Amino-4-cyclobutylmethylsulfonyl-6-methyl-1-(5-methylcarboxamidomethylbenzimidazolyl)-2-pyridinone Trifluoroacetate

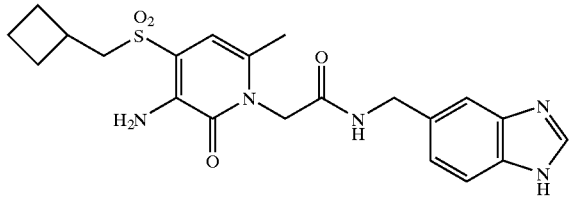

The title compound was prepared from 5-aminomethylbenzimidazole using standard procedures:

¹H NMR (400 MHz, CD₃OD): δ 9.34 (s, 1H), 7.78–7.82 (m, 2H), 7.58–7.61 (m, 1H), 6.27 (d, J=0.8 Hz, 1H), 4.88 (s, 2H), 4.61 (s, 2H), 3.28 (d, J=7.2 Hz, 2H), 2.73–2.77 (m, 1H), 2.28 (s, 3H), 1.80–2.13 (m, 6H); HRMS (FAB) $C_{21}H_{26}N_5O_4S$ calcd. 444.1700 (M+1). Found 444.1712.

EXAMPLE 23

3-Amino-4-cyclopropylmethylsulfonyl-6-methyl-1-(5-methylcarboxamidomethylbenzimidazolyl)-2-pyridinone Trifluoroacetate

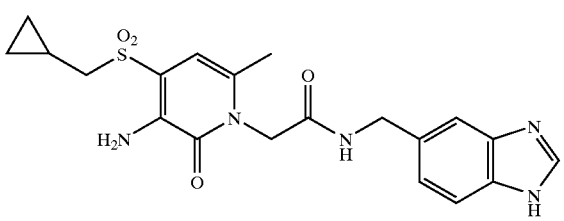

The title compound was prepared from 5-aminomethylbenzimidazole using standard procedures:

¹H NMR (400 MHz, CD₃OD): δ 9.34 (s, 1H), 7.79–7.83 (m, 2H), 7.61 (d, J=8.41 Hz, 1H), 6.30–6.32 (m, 1H), 4.81 (s, 2H), 4.62 (s, 2H), 3.12 (d, J=1.2 Hz, 2H), 2.27 (s, 3H), 1.03–1.07 (m, 1H), 0.56–0.61 (m, 2H), 0.26–0.30 (m, 2H); HRMS (FAB) $C_{20}H_{24}N_5O_4S$ calcd. 430.1543 (M+1). Found 430.1542.

EXAMPLE 24

Amides of 5-aminomethylindazole were Prepared as Follows

Step A: 5-Cyano-2-fluorobenzaldehyde

To a solution of 5-bromo-2-fluorobenzaldehyde (1.93 g, 9.51 mmol) in DMF (4 mL) was added copper(I) cyanide (0.98 g, 10.93 mmol). The mixture was heated to 190° C. and stirred for 5 h. The dark brown reaction mixture was poured into a solution containing ferric chloride (3.0 g), conc. HCl (0.93 mL) and water (6 mL) and warmed to 65° C. for 20 min. The mixture was partitioned between toluene (20 mL) and water (20 mL). The organic was washed with diluted HCl (25 mL), water (20 mL), 10% sodium hydroxide (25 mL), dried over magnesium sulfate, and concentrated to provide a solid product:

¹H NMR (CDCl₃) δ 10.34 (m, 1H), 8.21 (m, 1H), 7.90 (m, 1H), 7.35 (m, 1H).

Step B: 5-Cyanoindazole

5-Cyano-2-fluorobenzaldehyde (512 mg, 3.43 mmol) was dissolved in hydrazine hydrate (25 mL) at room temperature and the solution left to stand overnight. To this reaction mixture was added methylene chloride (30 mL). The mixture was purified by filtration through a pad of silica eluting with methylene chloride, concentrated in vacuo to afford a white solid:

¹H NMR (DMSO) δ 8.40 (s, 1H), 8.25 (s, 1H), 7.69 (m, 2H).

Step C: 5-Aminomethylindazole

To a solution of LiAlH₄ (0.76 g, 20.1 mmol) in THF (10 mL) cooled to 0° C. was added a solution of 5-cyanoindazole (0.64 g, 4.47 mmol) in THF (10 mL) dropwise. After 0.5 h the reaction mixture was warmed to reflux for 2 h, then cooled to 0° C. and quenched by the careful addition of water (0.76 mL), 1.0 N sodium hydroxide (0.76 mL), and water (2.28 mL). This mixture was filtered through a pad of celite and washed with THF/MeOH (3:1, 300 mL). Removal of the solvent in vacuo provided a solid which was purified via flash column chromatography (25× 150 mm column; elution with MeOH:CH₂Cl₂:CH₂Cl₂ saturated with NH₃, 10:60:30). This afforded the title compound as a light yellow solid:

¹H NMR (CDCl₃) δ 10.0 (s, 1H), 8.61 (s, 1H), 8.15 (s, 1H), 7.90–7.60 (m, 2H), 4.92 (s, 2H).

Step D: 3-(2-Phenylethylamino)-6-methyl-1-(5-methylenecarboxamidomethylindazolyl)-pyrazinone

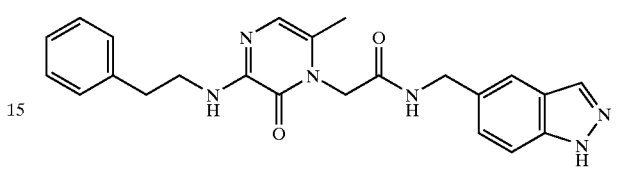

The title compound was prepared from 5-aminomethylindazole using standard procedures:

HRMS (FAB-POS M+1): calcd 417.2033 found 417.2043; Analysis: calculated for $C_{23}H_{24}N_6O_2$· 0.1 TFA; C, 65.12; H, 5.68; N, 19.64. Found: C, 65.49; H, 5.62; N, 19.28.

EXAMPLE 25

3-[2-(2-Pyridyl)ethylamino]-6-methyl-1-(5-methylene-carboxamidomethylindazolyl)-pyrazinone

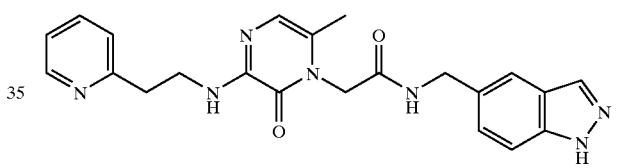

The title compound was prepared from 5-aminomethylindazole using standard procedures:

HRMS (FAB-POS M+1): calcd 418.1986 found 418.1987; Analysis: calculated for $C_{22}H_{23}N_7O_2$· 0.65 H2O; C, 61.56; H, 5.71 N, 22.85. Found: C, 61.56; H, 5.42 N, 22.72.

EXAMPLE 26

3-[2-(3,4-Dioxyphenyl)ethylamino]-6-methyl-1-(5-methylenecarboxamidomethylindazolyl)-pyrazinone

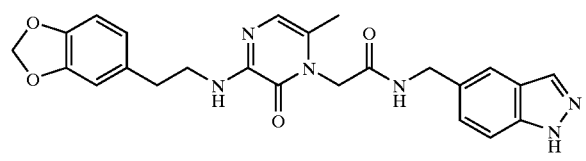

The title compound was prepared from 5-aminomethylindazole using standard procedures:

HRMS (FAB-POS M+1): calcd 461.1932 found 461.1927; Analysis: calculated for $C_{24}H_{24}N_6O_4$· 0.30 HOAc; C, 61.74; H, 5.31 N, 17.56. Found: C, 61.96; H, 5.13; N, 17.25.

EXAMPLE 27

3-[2-phenyl-(2,2-difluoroethylamino)]-6-methyl-1-(5-methylenecarboxamidomethylindazolyl)-pyrazinone

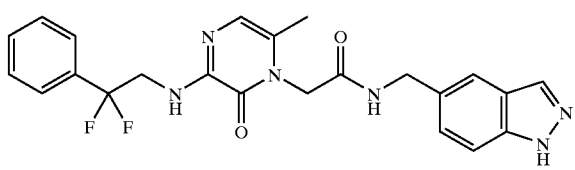

The title compound was prepared from 5-aminomethylindazole using standard procedures:

HRMS (FAB-POS M+1): calcd 453.1845 found 453.1822; Analysis: calculated for $C_{23}H_{22}N_6O_2$. 0.2; THF, 0.25 TFA; C, 58.91; H, 4.85; N, 16.97. Found: C, 59.00; H, 4.66; N, 16.96.

EXAMPLE 28

Amides of 5-aminomethyl-1-methylindazole were Prepared as Follows

Step A: 5-Cyano-1-methylindazole

To a solution of 5-cyano-2-fluorobenzaldehyde (0.50 g, 3.35 mmol) in ether (5 mL) was added methyl hydrazine (0.178 μL, 3.35 mmol) dropwise at room temperature. The mixture was stirred at room temperature for 1 h and concentrated in vacuo to give the hydrazone as a yellow solid. This solid was fused at 230° C. for 10 min, cooled to rt, dissolved in $CH_2Cl_2$ and purified by filtration through a pad of silica (eluant $CH_2Cl_2$:MeOH; 19:1) to afford the title compound as a light yellow solid: $^1$H NMR (DMSO) δ 8.38 (s, 1H), 8.23 (s, 1H), 7.84 (d, J=8.8 Hz, 1H), 7.71 (d, J=8.8 Hz, 1H), 4.09 (s, 3H).

Step B: 5-Aminomethyl-1-methylindazole

The title compound was prepared according to the method described in Example 24, Step C, 5-cyano-1-methylindazole as a starting material:

$^1$H NMR (CDCl$_3$) δ 7.93 (s, 1H), 7.63 (s, 1H), 7.36 (s, 2H), 4.72 (s, 3H), 4.07 (s, 2H); CI-MS: m/e=162.10 (M+1).

Step C: 3-(2-Phenylethylamino)-6-methyl-1-(1-methyl-5-methylenecarboxamidomethylindazolyl)-pyrazinone

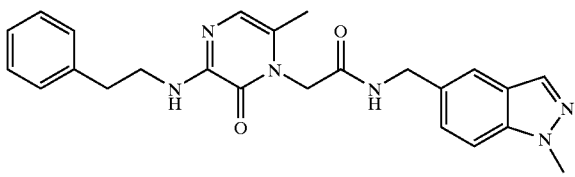

The title compound was prepared from 5-aminomethyl-1-methylindazole using standard procedures:

HRMS (FAB-POS M+1): calcd 431.2190 found 431.2179; Analysis: calculated for $C_{24}H_{26}N_6O_2$. 0.30 H2O; C, 66.12; H, 6.15; N, 19.28. Found: C, 66.07; H, 5.91; N, 18.95.

EXAMPLE 29

3-[2-(2-Pyridyl)ethylamino]-6-methyl-1-(1-methyl-5-methylenecarboxamidomethylindazolyl)-pyrazinone

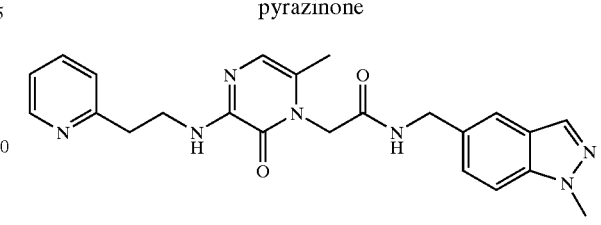

The title compound was prepared from 5-aminomethyl-1-methylindazole using standard procedures:

HRMS (FAB-POS M+1): calcd 432.2142 found 432.2145; Analysis: calculated for $C_{23}H_{25}N_7O_2$. 0.30 CH3OH; C, 63.44; H, 5.99; N, 22.23. Found: C, 63.44; H, 5.84; N, 21.84.

EXAMPLE 30

Amides of 5-Aminomethyl-3-methylindazole were Prepared as Follows

Step A: 4-Fluoro-3-(1-hydroxyethyl)benzonitrile

To a solution of 5-cyano-2-fluorobenzaldehyde (1.50 g, 10.06 mmol) in THF (15 mL) cooled to 0° C. was added methyllithium (7.90 mL, 11.06 mmol). The mixture was stirred at room temperature for 2 h and quenched by the addition of saturated NH$_4$Cl (10 mL). The mixture was partitioned between ethyl acetate (50 mL) and water (20 mL), the organic was washed with water (20 mL), dried over magnesium sulfate and concentrated in vacuo to provide a residue. Purification via flash column chromatography (30× 150 mm column; elution with EtOAc: Hex, 1:2) afforded pure compound:

$^1$H NMR (CDCl$_3$) δ 7.89 (dd, J=2.2; 6.7 Hz, 1H), 7.57 (m, 1H), 7.12 (t, J=9.1 Hz, 1H), 5.22 (m, 1H), 1.93 (d, J=4.4 Hz, 1H), 1.51 (d, J=6.4 Hz, 3H).

Step B: 5'-Cyano-2'-fluoroacetophenone

To a solution of pyridine (3.52 mL, 43.6 mmol) in CH$_2$Cl$_2$ (10 mL) was added dry chromium trioxide (2.18 g, 21.80 mmol) at 0° C. The reaction mixture was warmed to room temperature and stirred for 30 min. 4-fluoro-3-(1-hydroxyethyl)benzonitrile (600 mg, 3.63 mmol) dissolved in CH$_2$Cl$_2$ (10 mL) was added via canula. The reaction mixture was stirred for 10 min. and was diluted with ether and celite and stirred for an additional 20 min. The reaction mixture was filtered through a pad of celite and washed with ethyl acetate. The organic was washed then with 5% HCl and sat'd NaHCO$_3$, brine, dried over MgSO$_4$, and concentrated in vacuo to provide product:

$^1$H NMR (CDCl$_3$) δ 8.22 (dd, J=2.2; 6.6 Hz, 1H), 7.82 (m, 1H), 7.29 (m, 1H), 2.67 (d, J=5.0 Hz, 3H).

Step C: 5-Cyano-3-methylindazole

The title compound was prepared according to the method described in Example 24, Step B, 5'-cyano-2'-fluoroacetophenone as a starting material:

$^1$H NMR (CDCl$_3$) δ 10.02 (s, 1H), 8.09 (s, 1H), 7.60–7.50 (m, 2H), 2.62 (s, 3H).

Step D: Preparation of 5-aminomethyl-3-methylindazole

The title compound was prepared according to the method described in Example 24, Step C, 5-cyano-3-methylindazole as a starting material:

$^1$H NMR (CDCl$_3$) δ 9.77 (s, 1H), 7.61 (s, 1H), 7.38–7.26 (m, 2H), 4.00 (s, 2H), 2.59 (s, 3H).

Step E: 3-(2-Phenylethylamino)-6-methyl-1-(3-methyl-5-methylenecarboxamidomethylindazolyl)-pyrazinone

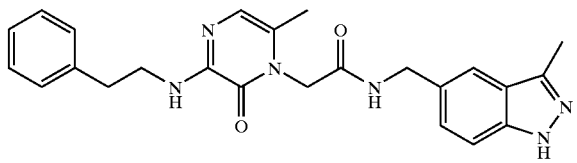

The title compound was prepared from 6-aminomethyl-1-methylindazole using standard procedures:
HRMS (FAB-POS M+1): calcd 431.2190 found 431.2194; Analysis: calculated for $C_{24}H_{26}N_6O_2$. 0.45 THF; C, 66.93; H, 6.44; N, 18.15. Found: C, 66.97; H, 6.32; N, 18.09.

EXAMPLE 31

3-[2-(2-Pyridyl)ethylamino]-6-methyl-1-(3-methyl-5-methylenecarboxamidomethylindazolyl)-pyrazinone

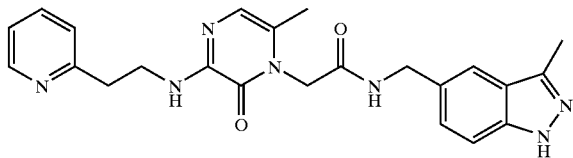

The title compound was prepared from 6-aminomethyl-3-methylindazole using standard procedures:
HRMS (FAB-POS M+1): calcd 432.2172 found 432.2153; Analysis: calculated for $C_{23}H_{25}N_7O_2$. 0.1H2O 0.15 TFA; C, 62.13; H, 5.67; N, 21.77. Found: C, 62.09; H, 5.59; N, 21.65.

EXAMPLE 32

3-[2-(2-Pyridyl)ethylamino]-6-methyl-1 -(3-methyl-5-methylenecarboxamidomethyl-1,2-benzisoxazolyl)-pyrazinone

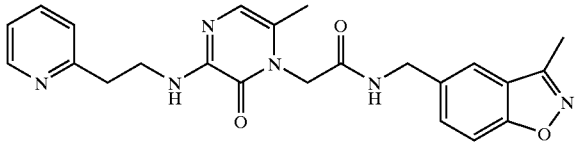

Step A: 5-Cyano-3-methyl-1,2-benzisoxazole
To a solution of 5'-cyano-2'-fluoroacetophenone (500 mg, 3.06 mmol) in MeOH (5 mL) was added hydroxyamine HCl salt (223 mg, 3.22 mmol) and sodium hydroxide (129 mg, 3.22 mmol). The reaction mixture was stirred at room temperature for 0.5 h and concentrated in vacuo to afford a solid product. This solid was added to a suspension of sodium hydroxide (147 mg, 3.68 mmol) in DMF (5 mL) at 0° C. After 0.5 h the reaction mixture was warmed to room temperature for 4 h and poured into cold brine. The mixture was extracted with ethyl acetate, the organic layer was dried over MgSO$_4$, and concentrated in vacuo to provide a residue. Purification via flash column chromatography (15×150 mm column; gradient elution with MeOH:CH$_2$Cl$_2$:CH$_2$Cl$_2$ saturated with NH$_3$, 5:65:30 to 10:60:30 300 mL each) afforded of a solid:

$^1$H NMR (CDCl$_3$) δ 8.03 (s, 1H), 7.82–7.65(m, 2H), 2.63 (s, 3H).
Step B: 5-Aminomethyl-3-methyl-1,2-benzisoxazole
The title compound was prepared according to the method described in Example 24, Step C, 5-cyano-3-methyl-1,2-benzisoxazole as a starting material:
$^1$H NMR (CDCl$_3$) δ 7.62–7.22 (m, 3H), 4.05 (s, 2H), 2.59 (s, 3H).
Step C: 3-[2-(2-Pyridyl)ethylamino]-6-methyl-1-(3-methyl-5-methylenecarboxamidomethyl-1,2-benzisoxazolyl)-pyrazinone
The title compound was prepared from 5-aminomethyl-3-methyl-1,2-benzisoxazole using standard procedures:
HRMS (FAB-POS M+1): calcd 433.1983 found 433.1999; Analysis: calculated for $C_{23}H_{24}N_6O_3$. 0.25 THF, 0.20 TFA; C, 60.92; H, 5.72; N, 18.22. Found: C, 61.20; H, 5.53; N, 18.27.

EXAMPLE 33

Amides of 5-Aminomethyl-6-methylbenzimidazole were Prepared as Follows
Step A: 6-Methyl-5-benzimidazole Carboxylic Acid
A 1L three neck round bottom flask equiped with an addition funnel and condenser was charged with a solution of 5,6-dimethylbenzimidazole (2.00 g, 13.69 mmol) dissolved in water (400 mL). The mixture was warmed to reflux and KMnO4 (8.60 g, 54.4 mmol) dissolved in water (200 mL) was added over a 0.5 h period. The reaction stirred for 0.5 h at reflux and was filtered hot through a plug a celite, washed with water (2×100 mL), acidified to pH 1 with 3N HCl and concentrated to 50 mL volume. The solution was aged for 2 h, filtered, washed with cold water and the solid was dried overnight at 50° C. under 25 mm vacuum to provide a white solid:
$^1$H NMR (CD$_3$OD) δ 9.43 (s, 1H), 8.39 (s, 1H), 7.73 (s, 1H), 2.77 (s, 3H).
Step B: 5-Hydroxymethyl-6-methylbenzimidazole
To a solution of 6-methyl-5-benzimidazole carboxylic acid (1.18 g, 5.55 mmol) dissolved in MeOH: CHCl3 (30 mL each) was added (trimethylsilyl)diazomethane (2.0 M in hexanes, 3.0 mL, 6 mmol). The mixture stirred for 0.5 h and was quenched with two drops of formic acid and concentrated in vacuo to a white solid which was used directly in the next step. To the crude ester dissolved in CH$_2$Cl$_2$ (30 mL), cooled to 0° C. was added Dibal-H (1.0 M in hexanes, 12.21 mL, 12.21 mmol). The mixture stirred for 1 h and was quenched with Rochelle salts (8.0 mL) and stirred overnight. Filtered solids through a plug of celite and washed with MeOH (150 mL), concentrated filtrate to a residue which was purified via column chromatography (30×150 mm column; gradient elution with MeOH:CH$_2$Cl$_2$: CH$_2$Cl$_2$ saturated with NH$_3$, 4:66:30 to 10:60:30 500 mL each) to provide a white solid:
TLC (MeOH:CH$_2$Cl$_2$:CH$_2$Cl$_2$ saturated with NH$_3$ 10:60:30) Rf=0.25; $^1$H NMR (CD$_3$OD) δ 8.06 (s, $^1$H), 7.61 (s, 1H), 7.39 (s, 1H), 4.72 (s, 2H), 2.44 (s, 3H).
Step C: 5-Azidomethyl-6-methylbenzimidazole
To a solution of 5-methanol-6-methylbenzimidazole (0.455 g, 2.81 mmol) dissolved in DMF (6 mL) and cooled to 0° C. was added diphenylphosphoryl azide (1.2 mL, 5.57 mmol) over 0.5 h and then added 1,8-diazabicyclo[4.3.0] undec-7-ene (0.50 mL, 3.37 mmol). The mixture stirred for 0.5 h and warmed to rt overnight. The volitiles were removed in vacuo and the resulting oil was purified via column chromotography (30×150 mm column; gradient elution with MeOH:CH$_2$Cl$_2$: CH$_2$Cl$_2$ saturated with NH$_3$, 1:69:30 to 3:67:30 500 mL each) to provide a white solid:

TLC (MeOH:CH₂Cl₂:CH₂Cl₂ saturated with NH₃ 10:60:30) Rf=0.50; ¹H NMR (CDCl₃) δ 7.93 (s, 1H), 7.51 (s, 1H), 7.42 (s, 1H), 4.41 (s, 2H), 2.43 (s, 3H).

Step D: 5-Aminomethyl-6-methylbenzimidazole

To a solution of 5-azidomethyl-6-methylbenzimidazole (0.365 g, 1.95 mmol) dissolved in THF (5 mL) was added triphenylphosphine (1.53 g, 5.85 mmol). The mixture stirred for 5 h, water (0.5 mL) was added and the reaction stirred overnight. The volitiles were removed in vacuo and the resulting solid was purified via column chromotography (25×150 mm column; gradient elution with MeOH:CH₂Cl₂:CH₂Cl₂ saturated with NH₃, 8:62:30 to 10:60:30 500 mL each) to provide a white solid:

TLC (MeOH:CH₂Cl₂:CH₂Cl₂ saturated with NH₃ 10:60:30) Rf=0.16; ¹H NMR (CDCl₃) δ 7.91 (s, 1H), 7.50 (s, 1H), 7.40 (s, 1H), 4.72 (s, 2H), 2.41 (s, 3H).

Step E: 3-[2-(2-Pyridyl)ethylamino]-6-methyl-1-(5-methylenecarboxamidomethyl-6-methylbenzimidazolyl)-pyrazinone

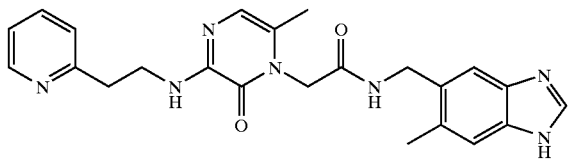

The title compound was prepared from 5-aminomethyl-6-methylbenzimidazole using standard procedures:

HRMS (FAB-POS; M+1) calcd 432.2142 found 432.2131; mp: 175–184° C. (deform); Analysis calculated for C₂₃H₂₅N₇O₂· 0.25 CH₂Cl₂; C, 61.68; H, 5.68; N, 21.66. Found: C, 61.95; H, 5.72; N, 21.44.

EXAMPLE 34

3-[1-(2-Pyridyl)-cyclopropylmethylamino]-6-methyl-1-(5-methylenecarboxamidomethyl-6-methylbenzimidazolyl)-pyrazinone

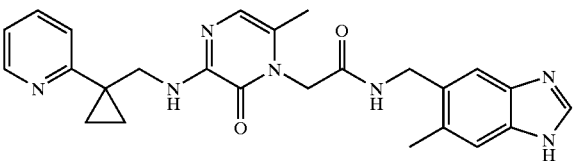

The title compound was prepared from 5-aminomethyl-6-methylbenzimidazole using standard procedures:

HRMS (FAB-POS; M+1) calcd 458.2304 found 458.2312; mp: 146–154° C.; Analysis calculated for C₂₅H₂₇N₇O₂· 0.50 H₂O; C, 64.36; H, 6.05; N, 21.02. Found: C, 64.00; H, 5.91; N, 20.73.

EXAMPLE 35

Amides of 3-Chloro-5-aminomethylindole were Prepared as Follows

Step A: 5-(t-Butoxycarbonylaminomethyl)-indole:

To 5-aminomethylindole (1.27 g, 8.68 mmol) dissoved in t-BuOH (80 mL) was added H₂O (4.6 mL), Et₃N (1.25 mL, 8.94 mmol) and (Boc)₂O (3.33 g, 15.28 mmol) was then added portionwise. The reaction was stirred for 2.5 h, concentrated in vacuo, diluted with EtOAc (120 mL), washed with 5% Na₂CO₃ (1×20 mL), H₂O (1×30 mL), and brine (1×30 mL). The organic layer was dried over MgSO₄, filtered and concentrated in vacuo to provide a pale orange oil. Purification by flash chromatography (25×150 mm column; gradient elution with EtOAc: hexanes, 1:5 to 1:3) afforded a yellow oil:

¹H NMR (CDCl₃) δ 8.27 (br s, 1H, NH), 7.54 (s, 1H, 4-H), 7.34 (d, J=8.4 Hz, 1H, 7-H), 7.20 (t, J=2.8 Hz, 1H, 2-H), 7.12 (d, J=8.1 Hz, 1H, 6-H), 6.51 (t, J=2.2 Hz, 1H, 3-H), 4.82 (br s, 1H, NH), 4.39 (d, J=5.3 Hz, 2H, CH₂), 1.47 (s, 9H).

Step B: 3-Chloro-5-(t-butoxycarbonylaminomethyl)-indole:

To a solution of 5-(t-butoxycarbonylaminomethyl)-indole (0.51 g, 2.05 mmol) in CH₂Cl₂ (12 mL) under Argon at 15°–20° C. was added N-chlorosuccinimide (0.245 g, 1.82 mmol) portionwise over 1 hr. The reaction stirred 0.5 h and was partitioned with H₂O and CH₂Cl₂. The aqueous layer was extracted with CH₂Cl₂ (2×), dried over MgSO₄, filtered, and concentrated in vacuo to a brown residue. Purification via flash chromatography (25×150 mm column; gradient elution with EtOAc: hexanes, 1:4 to 1:3) yielded a colorless oil:

¹H NMR (CDCl₃) δ 9.18 (br s, 1H, NH), 7.51 (s, 1H, 4-H), 7.31 (d, J=8.4 Hz, 1H, 7-H), 7.17 (s, 1H, 6-H), 7.16 (s, 1H, 2-H), 5.05 (br s, 1H, NH), 4.40 (s, 2H, CH₂), 1.48 (s, 9H).

Step C: 3-Chloro-5-aminomethylindole:

To a solution of 3-chloro-5-(t-butoxycarbonylaminomethyl)-indole (2.62 g, 9.33 mmol) in CH₂Cl₂ (25 mL), cooled to 0° C. was added trifluoroacetic acid (10 mL). After 1 h the reaction was basified with aqueous NaOH (1 N) to pH=10, extracted with CH₂Cl₂ (3×) and then with CH₂Cl₂:MeOH (3:1). The combined organics were dried over MgSO₄, filtered, and concentrated in vacuo. Purification of the resulting orange residue by flash chromatography (30×150 mm column; gradient elution with MeOH:CH₂Cl₂:CH₂Cl₂ saturated with NH₃, 4:66:30 to 10:60:30 500 mL each) afforded the title compound as a yellow oil:

¹H NMR (CDCl₃) δ 8.83 (br s, 1H, NH), 7.54 (s, 1H, 4-H), 7.28 (d, J=8.4 Hz, 1H, 7-H ), 7.17 (dd, J=8.4 Hz, 1.7 Hz, 1H, 6-H), 7.13 (s, 1H, 2-H), 3.98 (s, 2H, CH₂), 1.70 (br s, 2H, NH₂); Low Res MS: (M+1) 181.05.

Step D: 3-[2-(2-Pyridyl)ethylamino]-6-methyl-1-(3-chloro-5-methylene-carboxamidomethylindolyl)-pyrazinone

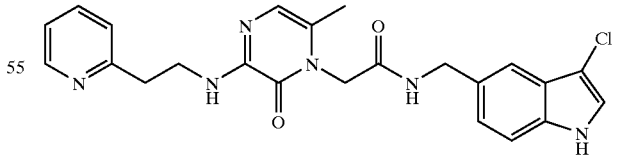

The title compound was prepared from 5-aminomethyl-3-chloroindole using standard procedures:

HRMS (FAB-POS; M+1) calcd 451.1644 found 451.1653; mp: 224–226° C. Analysis calculated for C₂₃H₂₃N₆O₂Cl; C, 61.26; H, 5.14; N, 18.64. Found: C, 61.27; H, 5.28; N, 18.34.

EXAMPLE 36

3-(2-Phenethylamino)-6-methyl-1-(3-chloro-5-methylenecarboxamidomethylindolyl)-pyrazinone

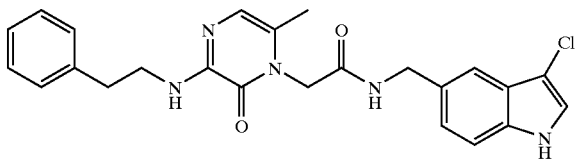

The title compound was prepared from 5-aminomethyl-3-chloroindole using standard procedures:

HRMS (FAB-POS; M+1) calcd 450.1691 found 450.1696; mp: 223–226° C.; Analysis calculated for $C_{24}H_{24}N_5O_2Cl$. 0.60; H, 20; C, 62.56; H, 5.51; N, 15.20. Found: C, 62.60; H, 5.46; N, 14.81.

EXAMPLE 37

3-[2-(2-Pyridyl)ethylamino]-6-methyl-1-(5-methylene-carboxamidomethylindolyl)-pyrazinone

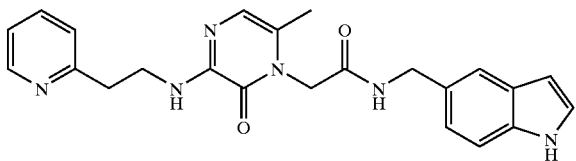

The title compound was prepared from 5-aminomethylindole using standard procedures:

HRMS (FAB-POS; M+1) calcd 417.2039 found 417.2051; mp: 208–212° C.; Analysis calculated for $C_{23}H_{24}N_6O_2$. 0.35 $H_2O$; C, 65.33; H, 5.89; N, 19.88. Found: C, 64.97; H, 5.67; N, 19.85.

EXAMPLE 38

3-[2-(3-Pyridyl)ethylamino]-6-methyl-1-(5-methylene-carboxamidomethylindolyl)-pyrazinone

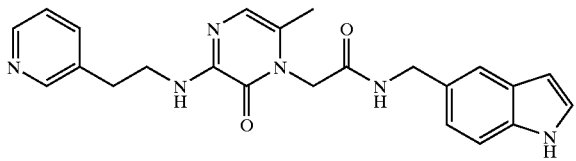

The title compound was prepared from 5-aminomethylindole using standard procedures:

HRMS (FAB-POS M+1): calcd 417.2033 found 417.2036; Analysis: calculated for $C_{23}H_{24}N_6O_2$; C, 64.78; H, 5.93; N, 19.71. Found: C, 64.80; H, 5.95; N, 19.71.

EXAMPLE 39

3-[1-(2-Pyridyl)cyclopropylmethylamino]-6-methyl-1-(5-methylenecarboxamidomethylindolyl)-pyrazinone

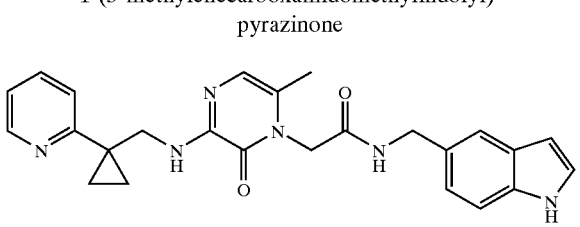

The title compound was prepared from 5-aminomethylindole using standard procedures:

HRMS (FAB-POS; M+1) calcd 443.2190 found 443.2198; mp: 212–215° C.; Analysis calculated for $C_{25}H_{26}N_6O_2$; C, 67.85; H, 5.92; N, 18.99. Found: C, 67.68; H, 6.12; N, 19.17.

EXAMPLE 40

3-[2-(3,4-Methylenedioxyphenyl)ethylamino]-6-methyl-1-(5-methylenecarboxamidomethylindolyl)-pyrazinone

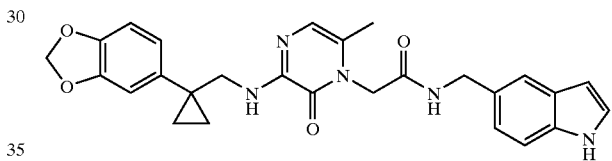

The title compound was prepared from 5-aminomethylindole using standard procedures:

HRMS (FAB-POS; M+1) calcd 460.1985 found 460.1971; mp: 245–247° C.; Analysis calculated for $C_{25}H_{25}N_5O_4$. 0.30; $H_2O$; C, 64.58; H, 5.55; N, 15.07. Found: C, 64.30; H, 5.52; N, 15.18.

EXAMPLE 41

3-[1-(2-Pyridyl)cyclopropylmethylamino]-6-methyl-1-(5-methylenecarboxamidomethyl-benzimidazolyl)-pyrazinone

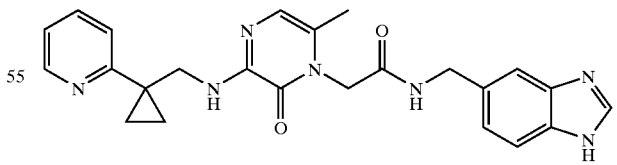

The title compound was prepared from 5-aminomethylbenzimidazole using standard procedures:

HRMS (FAB-POS; M+1) calcd 444.2142 found 444.2150; mp: 134–139° C.; Analysis calculated for $C_{24}H_{25}N_7O_2$. 0.40 $H_2O$; C, 63.95; H, 5.77; N, 21.76. Found: C, 63.59; H, 5.84; N, 21.51.

EXAMPLE 42

3-[2-(2-Pyridyl)ethylamino]-6-methyl-1-(5-methylenecarboxamidomethylbenzimidazolyl)-pyrazinone

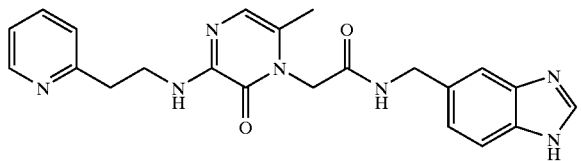

The title compound was prepared from 5-aminomethylbenzimidazole using standard procedures:

HRMS (FAB-POS; M+1) calcd 418.1986 found 418.1989.

EXAMPLE 43

3-(2-Phenethylamino)-6-methyl-1-(5-methylcarboxamidomethyl-7-azaindolyl)-pyrazinone Dihydrochloride

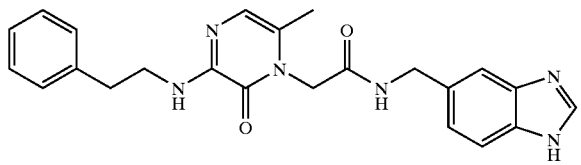

The title compound was prepared from 5-aminomethylbenzimidazole using standard procedures:

HRMS (FAB) $C_{23}H_{25}N_6O_2$ (M+1) calcd. 417.2033. Found: 417.2029.

EXAMPLE 44

3-[2-(2-Pyridyl)ethylamino]-6-methyl-1-(5-methylcarboxamidomethyl-7-azaindolyl)-pyrazinone Trihydrochloride

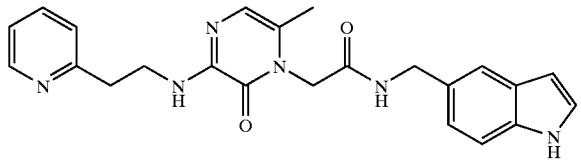

The title compound was prepared from 5-aminomethyl-7-azaindole using standard procedures:

HRMS (FAB) $C_{22}H_{24}N_7O_2$ (M+1) calcd. 418.1986. Found: 418.1993.

EXAMPLE 45

3-[2-(2-Pyridyl)ethylamino]-6-methyl-1-(5-methylcarboxamidomethyl-4-azaindolyl)-pyrazinone Trihydrochloride

The title compound was prepared from 5-aminomethyl-4-azaindole using standard procedures:

HRMS (FAB) $C_{22}H_{24}N_7O_2$ (M+1) calcd. 418.1986. Found: 418.1975.

EXAMPLE 46

3-[2,2-Difluoro-2-phenethylamino)-6-methyl-1-(5-methylcarboxamidomethyl-4-azaindolyl)-pyrazinone Dihydrochloride

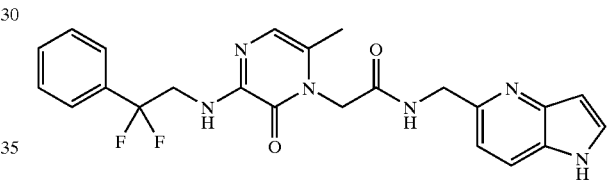

The title compound was prepared from 5-aminomethyl-4-azaindole using standard procedures:

HRMS (FAB) $C_{23}H_{23}N_6O_2F_2$ (M+1) calcd. 453.1845. Found: 453.1835.

EXAMPLE 47

3-[2-(2-Pyridyl)ethylamino]-6-methyl-1-(5-methylcarbox-amidomethyl-6-azaindolyl)-pyrazinone Trihydrochloride

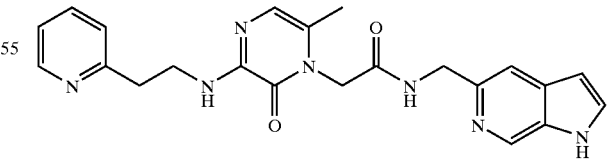

The title compound was prepared from 5-aminomethyl-6-azaindole using standard procedures:

HRMS (FAB) $C_{22}H_{24}N_7O_2$ (M+1) calcd. 418.1986. Found: 418.1981.

EXAMPLE 48

3-[2,2-Difluoro-2-phenethylamino)-6-methyl-1-(5-methylcarboxamidomethyl-6-azaindolyl)-pyrazinone Dihydrochloride

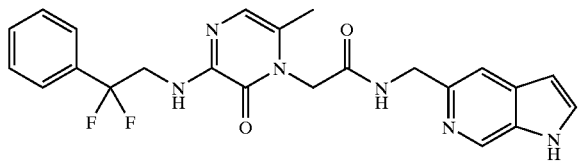

The title compound was prepared from 5-aminomethyl-6-azaindole using standard procedures:

HRMS (FAB) C$_{23}$H$_{23}$N$_6$O$_2$F$_2$ (M+1) calcd. 453.1845. Found: 453.1860.

EXAMPLE 49

3-[2-(2-Pyridyl)ethylamino]-6-methyl-1-(3-chloro-5-methylcarboxamidomethyl-6-azaindolyl)-pyrazinone Dihydrochloride Trihydrochloride

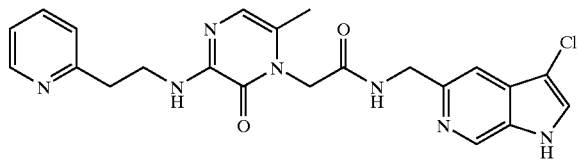

The title compound was prepared from 5-aminomethyl-3-chloro-6-azaindole using standard procedures:

HRMS (FAB) C$_{23}$H$_{23}$N$_6$O$_2$F$_2$ (M+1) calcd. 452.1596. Found: 452.1600.

EXAMPLE 50

[R]-7-(5-Methylenecarboxamidomethylindolyl)-6-methyl-2-oxo-3-propyl-1,2,3,4-tetrahydro-1,7-naphthiridine-[7H]-8-one

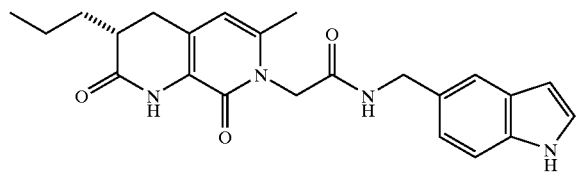

The title compound was prepared from 5-aminomethylindole using standard procedures:

LRMS (FAB) 407 (M+1).

EXAMPLE 51

[R]-7-(5-Methylenecarboxamidomethylindolyl)-3-cyclo-butylmethyl-6-methyl-2-oxo-1,2,3,4-tetrahydro-1,7-naphthiridine-[7H]-8-one

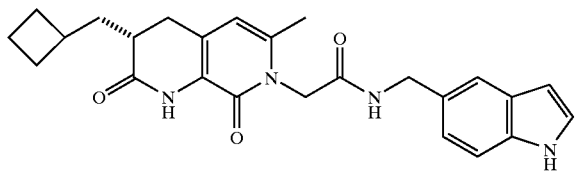

The title compound was prepared from 5-aminomethylindole using standard procedures:

LRMS (FAB) 433.2 (M+1).

EXAMPLE 52

[R]-7-(4-aza-5-Methylenecarboxamidomethylindolyl)-3-cyclo-butylmethyl-6-methyl-2-oxo-1,2,3,4-tetrahydro-1,7-naphthiridine-[7H]-8-one

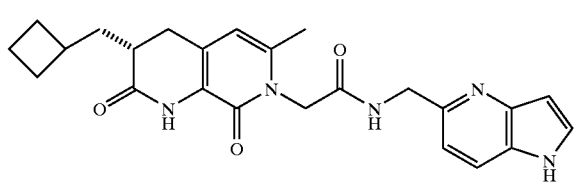

The title compound was prepared from 5-aminomethyl-4-azaindole using standard procedures:

LRMS (FAB) 434.2 (M+1).

EXAMPLE 53

[R]-7-(5-Methylenecarboxamidomethylindazolyl)-3-cyclo-butylmethyl-6-methyl-2-oxo-1,2,3,4-tetrahydro-1,7-naphthiridine-[7H]-8-one

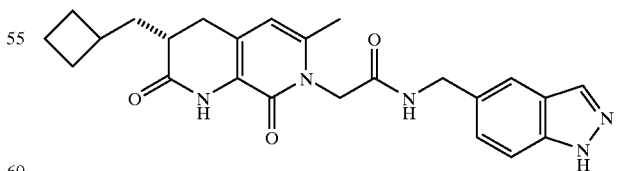

The title compound was prepared from 5-aminomethylindazole using standard procedures:

LRMS (FAB) 434.2 (M+1).

EXAMPLE 54

[R]-7-(7-aza-5-Methylenecarboxamidomethylindolyl)-3-cyclobutylmethyl-6-methyl-2-oxo-1,2,3,4-tetrahydro-1,7-naphthiridine-[7H]-8-one

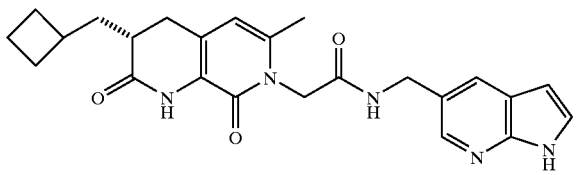

The title compound was prepared from 5-aminomethyl-7-azaindole using standard procedures:

LRMS (FAB) 434.2 (M+1).

EXAMPLE 55

[R]-7-(4-aza-5-Methylenecarboxamidomethylindolyl)-3-cyclopropylmethyl-6-methyl-2-oxo-1,2,3,4-tetrahydro-1,7-naphthiridine-[7H]-8-one

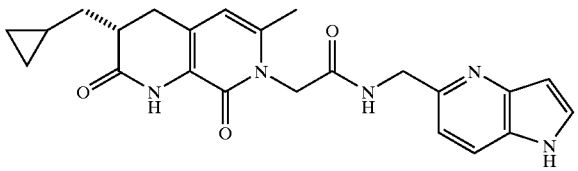

The title compound was prepared from 5-aminomethyl-4-azaindole using standard procedures:

LRMS (FAB) 420.2 (M+1).

EXAMPLE 56

Preparation of [R]-7-(4-aza-5-Methylenecarboxamidomethylindolyl)-3-(2-methyl-1-propyl)-6-methyl-2-oxo-1,2,3,4-tetrahydro-1,7-naphthiridine-[7H]-8-one

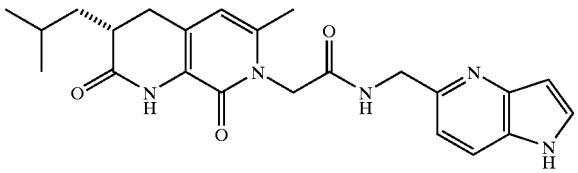

The title compound was prepared from 5-aminomethyl-4-azaindole using standard procedures:

LRMS (FAB) 422.1 (M+1).

EXAMPLE 57

[R]-7-(6-aza-5-Methylenecarboxamidomethylindolyl)-3-cyclobutylmethyl-6-methyl-2-oxo-1,2,3,4-tetrahydro-1,7-naphthiridine-[7H]-8-one

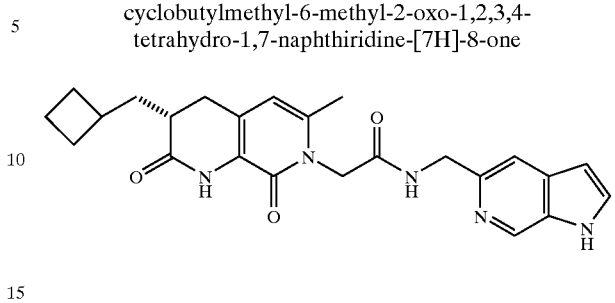

The title compound was prepared from 5-aminomethyl-6-azaindole using standard procedures:

LRMS (FAB) 434.2 (M+1).

EXAMPLE 58

Amides of 3-(2,2-Difluoro-2-(2-pyridylethylamino)-6-methylpyrazin(1H)-2-one-1-acetic Acid were Prepared as Follows Step A: 2,2-Difluoro-2-(2-pyridyl)ethanol To a 0° C. stirred solution of 3.97 g (19.7 mmol) of ethyl 2-pyridyldifluoroacetate (prepared according to T. Taguchi, et al., *Tetrahedron Lett.* 1986, 27, 6103) in 40 mL of methanol was added 757 mg (20 mmol) of sodium borohydride in several portions. After stirring for 0.5 h, the cold bath was removed, and stirring continued another 0.5 h. The reaction was quenched with 2M HCl, and the solvents removed under reduced pressure. The residue was partitioned between ether and 10% $Na_2CO_3$, the aqueous layer extracted with several portions of ether and the combined organic layers washed with brine, dried over $MgSO_4$ and the solvents removed to give 2.97 g of a yellow oil that was chromatographed on 65 g of fine $SiO_2$ using 99:1 to 97:3 $CH_2-Cl_2-CH_3OH$ to give the title compound as an almost colorless solid:

$^1$H NMR (CDCl$_3$) δ 8.61 (d, 1H, 4.5 Hz), 7.88 (td, 1H, 8.0, 1.7 Hz), 7.73 (d, 1H, 7.8 Hz), 7.4–7.45 (m, 1H), 4.25 (td, 2H, 12.5, 7.1 Hz), 3.46 (t, 1H, 6.6 Hz).

Step B: 2,2-Difluoro-2-(2-pyridyl)ethyl Trifluoromethanesulfonate

To a stirred −78° solution of 50 mg (0.31 mmol) of 2,2-difluoro-2-(2-pyridyl)ethanol and 100 mg (0.49 mmol) of 2,6-di-t-butyl-4-methylpyridine in 1.0 mL of $CH_2Cl_2$ was added 79 µL (0.47 mmol) of trifluoromethansulfonic anhydride dropwise under Ar. After the addition, the cold bath was removed, and stirring continued for 0.5 h. The reaction was diluted with 2 mL of pentane, and the resulting precipitate washed with pentane. The filtrate was evaporated in vacuo to dryness to give the title compound as a yellow solid:

$^1$H NMR (CDCl$_3$) δ 8.66 (d, 1H, 4.9 Hz), 7.89 (td, 1H, 7.7, 1.7 Hz), 7.76 (d, 1H, 7.9 Hz), 7.45–7.49 (m, 1H), 5.12 (t, 2; H, 11.9 Hz).

Step C: 2,2-Difluoro-2-(2-pyridyl)ethylazide

A solution of 105 mg (0.31 mmol) of 2,2-difluoro-2-(2-pyridyl)ethyl trifluoromethanesulfonate and 43 mg (0.66 mmol) of sodium azide in 1.0 mL of DMF was heated at 60° C. under Ar. After 1.5 h, the mixture was cooled to rt, diluted with water and extracted with two portions of ether. The combined organic layers were washed twice with water, brine and dried over $MgSO_4$. The solvents were removed at reduced pressure and a bath temperature of 20° C. to give the title compound as a brown oil:

¹H NMR (CDCl₃) δ 8.68 (d, 1H, 4.2 Hz), 7.86 (td, 1H, 7.8, 1.5 Hz), 7.72 (d, 1H, 7.8 Hz), 7.40–7.45 (m, 1H), 4.03 (t, 2H, 13.2 Hz).

Step D: 2.2-Difluoro-2-(2-pyridyl)ethylamine

A stirred solution of 100 mg of 2,2-difluoro-2-(2-pyridyl) ethylazide was hydrogenated in 10 mL of ethyl acetate over 100 mg of 10% palladium on carbon using a balloon for 1 h. The catalyst was removed by filtration and the solvents removed at reduced pressure to give the title compound as a yellow oil:

¹H NMR (CDCl₃) δ 8.66 (d, 1H, 4.2 Hz), 7.82 (td, 1H, 7.7, 1.7 Hz), 7.68 (d, 1H, 8.1 Hz), 7.37–7.40 (m, 1H), 3.44 (t, 2H, 14.3 Hz), 1.41 (br s, 2H).

Step E: Ethyl 3-(2,2-Difluoro-2-(2-pyridylethylamino)-6-methylpyrazin(1H)-2-one-1-acetate A solution of 683 mg (4.32 mmol) of 2,2-difluoro-2-(2-pyridyl)ethylamine and 792 mg (2.88 mmol) of ethyl 3-bromo-6-methylpyrazin(1H)-2-one-1-acetate was heated to 110° in a sealed tube overnight in 15 mL of toluene. The reaction was concentrated to approx half volume, and heating continued for 3 days. A 616 mg (3.0 mmol) portion of 2,6-di-t-butyl-4-methylpyridine was added, and heating continued for 2 days. After cooling to rt, the reaction was diluted with ethyl acetate, washed with 10% Na₂CO₃ and the aqueous layers washed with 3 portions of ethyl acetate. The combined organic layers were dried over MgSO₄ and the solvents removed at reduced pressure to give an oil that was chromatographed on SiO₂ using 85:15 hexane-EtOAc to give the title compound as a pale yellow solid:

¹H NMR (CDCl₃) δ 8.67 (d, 1H, 4.8 Hz), 7.80 (t, 1H, 7.9 Hz), 7.68 (d, 1H, 7.9 Hz), 7.36–7.39 (m, 1H), 6.71 (s, 1H), 6.31 (br t, 1H), 4.69 (s, 2H), 4.35 (td, 2H, 14.1, 6.6 Hz), 4.24 (q, 2H, 7.1 Hz), 2.11 (s, 3H), 1.29 (t, 3H, 6.8 Hz).

Step F: 3-(2,2-Difluoro-2-(2-pyridylethylamino)-6-methylpyrazin(1H)-2-one-1-acetic Acid To a stirred solution of 257 mg (0.73 mmol) of ethyl 3-(2,2-difluoro-2-(2-pyridylethylamino)-6-methylpyrazin (1H)-2-one-1-acetate in 10 mL of methanol was added 122 mg (2.19 mmol) of potassium hydroxide in 2 mL of water. After 45 min, the solution was concentrated at reduced pressure, and the residue dissolved in 3 mL of water. This solution was acidified to pH=3 using 10% HCl, and concentrated at reduced pressure to give a white solid containing potassium chloride and the title compound: ¹H NMR (CD₃OD) δ 8.65 (d, 1H, 4.7 Hz), 7.95 (td, 1H, 7.9, 1.8 Hz), 7.72–7.74 (m, 1H), 7.50–7.54 (m, 1H), 6.64 (d, 1H, 1.09 Hz), 4.78 (s, 2H), 4.31 (t, 2H, 14.1 Hz), 2.16 (s, 3H).

Step G: 3-(2,2-Difluoro-2-(2-pyridylethylamino)-6-methyl-1-(5-methylenecarboxamidomethylindolyl)-pyrazinone

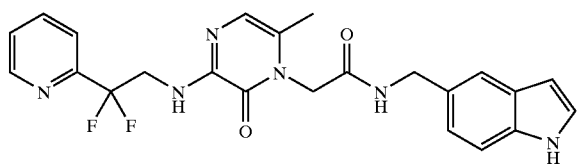

The title compound was prepared from 5-aminomethylindole using standard procedures:
LRMS (FAB) 453 (M+1).

EXAMPLE 59

3-(2,2-Difluoro-2-(2-pyridylethylamino)-6-methyl-1-(5-methylenecarboxamidomethylbenzimidazolyl)-pyrazinone

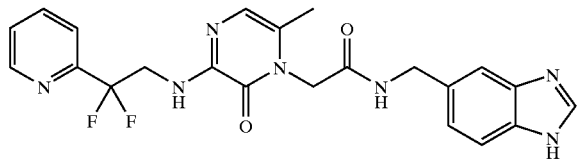

The title compound was prepared from 5-aminomethylbenzimidazole using standard procedures:
LRMS (FAB) 454 (M+1).

EXAMPLE 60

3-(2,2-Difluoro-2-(2-pyridylethylamino)-6-methyl-1-(4-aza-5-methylenecarboxamidomethylindolyl)-pyrazinone

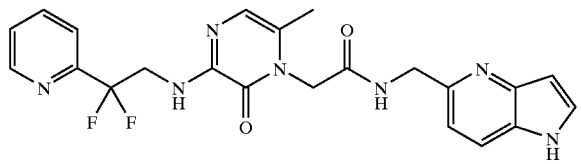

The title compound was prepared from 5-aminomethyl-4-azaindole using standard procedures: LRMS (FAB) 454.2 (M+1).

EXAMPLE 61

3-(2,2-Difluoro-2-(2-pyridylethylamino)-6-methyl-1-(6-aza-5-methylenecarboxamidomethylindolyl)-pyrazinone

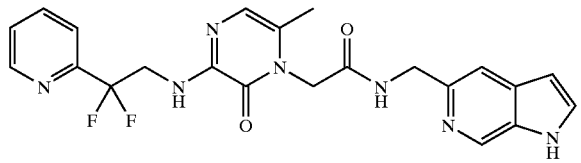

The title compound was prepared from 5-aminomethyl-6-azaindole using standard procedures:
LRMS (FAB) 454.2 (M+1).

EXAMPLE 62

3-(4-Cyclopropylbutylamino)-6-methyl-1-(6-aza-5-methylenecarboxamidomethylindolyl)-pyrazinone

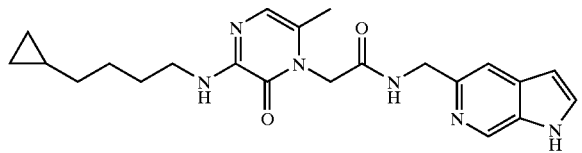

Step A: 4-Cyclopropylbutanol

A solution of 65 mL of a 1.1 M solution of diethylzinc in toluene was diluted with 140 mL of dry 1,2-dichloroethane and cooled to 0° C. To this stirred solution was added 25 g (142 mmol) of chloroiodomethane via syringe in a slow stream under Ar. A 4.26 mL portion (35.4 mmol) of 5-hexen-1-ol was added dropwise via syringe, and the cold bath allowed to expire over a 3 h period. The reaction was carefully quenched by the addition of 25 mL of sat. NH$_4$Cl and stirred overnight. The reaction was diluted with water and extracted with three portions of ether, the combined organic layers washed with water, brine, dried over Na$_2$SO$_4$ and the solvents removed to give the title compound as a colorless oil:

$^1$H NMR (CDCl$_3$) δ 3.61–3.69 (m, 2H), 1.55–1.65 (m, 2H), 1.40–1.55 (m, 2H), 1.18–1.26 (m, 2H), 0.6–0.73 (m, 1H), 0.37–0.43 (m, 2H), −0.03–0.03 (m, 2H).

Step B: 4-Cyclopropylbutyl Methanesulfonate

To a stirred 0° C. solution of 683 mg (6.0 mmol) of 4-cyclopropylbutanol and 1.25 mL (9.0 mmol) of triethylamine in 10 mL of CH$_2$Cl$_2$ was added 697 µL (9.0 mmol) of methanesulfonyl chloride dropwise under Ar. The cold bath was allowed to expire over a 2 h period at which time the reaction mixture was diluted with CH$_2$Cl$_2$, washed with cold 1M HCl, water, sat. NaHCO$_3$, brine, dried over MgSO$_4$ and the solvents removed to give the title compound as a yellow oil:

$^1$H NMR (CDCl$_3$) δ 4.24 (t, 2H, 6.4 Hz), 3.01 (s, 3H), 1.72–1.84 (m, 2H) 1.45–1.58 (m, 2H), 1.20–1.29 (m, 2H), 0.6–0.73 (m, 1H), 0.37–0.43 (m, 2H), −0.03–0.03 (m, 2H).

Step C: 4-Cyclopropylbutylazide

A solution of 880 mg (4.6 mmol) of 4-cyclopropylbutyl methanesulfonate and 585 mg (9.0 mmol) of sodium azide in 6.0 mL of DMF was heated at 60° C. under Ar overnight. After cooling to rt, the mixture was diluted with water, and extracted with two portions of ether. The combined organic layers were washed twice with water, brine, and dried over MgSO$_4$. The solvents were concentrated by distillation at atmospheric pressure to give a solution of the title compound in ether that was used directly in the next step.

Step D: 4-Cyclopropylbutylamine

The solution of 4-cyclopropylbutylazide from the previous step was diluted with 15 mL of THF, and 1.8 g (9.45 mmol) of triphenylphosphine and 165 µL (9.14 mmol) of water were added. After the gas evolution had ceased, the reaction was heated to 40° C. overnight. The reaction mixture was treated with 5.0 mL of 2M HCl and the solvents removed at reduced pressure. The residue was partitioned between 10% Na$_2$CO$_3$ and ether, the aqueous layer extracted with ether, and the combined organic layers washed with brine, dried over Na$_2$SO$_4$, and filtered. A 4.5 mL portion of 1.2 M HCl in ethyl acetate was added dropwise, and the ppt stirred for 5 min. The solids were removed by filtration and washed with ether to give 267 mg of the title compound as a colorless solid. This material was partitioned between 10% Na$_2$CO$_3$ and ether, the aqueous layer extracted with ether, the combined organic layers washed with brine, dried over Na$_2$SO$_4$ and the solvents removed by distillation at atmospheric pressure to give the title compound as a colorless oil:

$^1$H NMR (CDCl$_3$) δ 2.66 (t, 2H, 7 Hz), 1.35–1.60 (m, 6H), 0.6–0.73 (m, 1H), 0.37–0.43 (m, 2H), −0.03–0.03 (m, 2H).

Step E: 3-(4-Cyclopropylbutylamino)-6-methyl-1-(6-aza-5-methylenecarboxamidomethylindolyl)-pyrazinone The title compound was prepared using the procedures of Example 58, Steps E and F followed by a standard coupling procedure.

EXAMPLE 63

3-(3-Cyclopropyl-2,2-difluoropropylamino)-6-methyl-1-(4-aza-5-methylenecarboxamidomethylindolyl)-pyrazinone

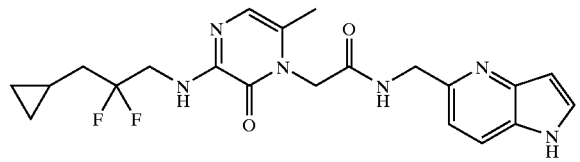

Step A: Methyl 3-Cyclopropyl-2,2-difluoropropionate

To a 0° C. solution of 2.95 g (21.7 mmol) of 2,2-difluoro-4-pentenoic acid (prepared according to Tang et al, Chem. Res. Tox. 8, 671 (1995)) in 18.5 mL of ether and 1.5 mL of methanol was added 7.0 mL (14 mmol) of a 2.0 M solution of trimethylsilyldiazomethane in hexane via syringe over a 5 min period until a yellow color persisted. Stirred for 15 min in the cold. In a separate flask, 3.3 g of KOH was dissolved in 8.0 mL of cold water, diluted with 23 mL of ether, and cooled in an ice bath. To this stirred mixture was added 2.65 g (18 mmol) of 1-methyl-3-nitro-1-nitrosoguanidine in portions over a 5 min period. Stirred in the cold for 10 min, removed the aqueous layer by pipette, and added the yellow organic layer to the solution of ester prepared earlier. To this 0° C. solution under Ar was added a very small portion of Pd(OAc)$_2$ which caused vigorous gas evolution. After the reaction had subsided, the flask was removed from the cold bath and the reaction stirred for 0.5 h. The reaction was then poured through a 10 g pad of SiO$_2$ and eluted with 40 mL of ether to give the title compound as a solution that was used directly in the next step. An aliquot was removed and concentrated to give the title compound as a pale yellow oil:

$^1$H NMR (CDCl$_3$) δ 3.88 (s, 3H), 2.0 (td, 2H, 15.8, 7.0 Hz), 0.75–0.85 (m, 1H), 0.50–0.58 (m, 2H), 0.12–0.19 (m, 2H).

Step B: 3-Cyclopropyl-2,2-difluoropropanol

The solution containing the methyl 3-cyclopropyl-2,2-difluoropropionate from the previous step was diluted with 20 mL of ethanol and cooled to 0° C. under Ar. To this stirred solution was added 605 mg (16 mmol) of sodium borohydride in small portions under Ar. The reaction was stirred in the cold for 1 h and then stored in the freezer for several days. The cold reaction mixture was quenched by the dropwise addition of 2M HCl until no further gas evolution was observed. The reaction was extracted with four portions of ether, the combined organic layers washed with water, brine, dried over Na$_2$SO$_4$ and the solvents removed by distillation at atm. pressure to give a solution of the product in ethanol. This solution was partitioned between pentane and water, the aqueous layer extracted with three portions of pentane, the combined organic layers dried over MgSO$_4$ and the solvents removed by distillation at atm. pressure to give the title compound as a colorless oil:

$^1$H NMR (CDCl$_3$) δ 3.84 (td, 2H, 12.9, 7.1 Hz), 1.85 (td, 2H, 15.9, 7.1 Hz), 0.80–0.90 (m, 1H), 0.53–0.58 (m, 2H), 0.17–0.23 (m, 2H).

Step C: 3-Cyclopropyl-2,2-difluoropropyl trifluoromethanesulfonate

To a 0° C. solution of 952 mg (7.0 mmol) of 3-cyclopropyl-2,2-difluoropropanol and 5.0 g (18 mmol) of 2,6-di-t-butyl-4-methylpyridine in 7 mL of CH$_2$Cl$_2$ was added 5.0 g of trifluoromethanesulfonic anhydride dropwise under Ar. The cold bath was removed and the mixture stirred overnight. The reaction mixture was diluted with 100 mL of pentane, and the precipitate removed by filtration. The filter cake was washed with pentane, and the filtrate washed with two portions of cold 1M HCl, brine, dried over $Na_2SO_4$ and the solvents removed at reduced pressure to give the title compound as an oil:

$^1$H NMR (CDCl$_3$) δ 4.62 (t, 2H, 11.4 Hz), 1.91 (td, 2H, 15.6, 7.1 Hz), 0.79–0.88 (m, 1H), 0.58–0.63 (m, 2H), 0.17–0.23 (m, 2H).

Step C: 3-Cyclopropyl-2,2-difluoropropylazide

A solution of 1.68 g (6.3 mmol) of 3-cyclopropyl-2,2-difluoropropyl trifluoromethanesulfonate and 820 mg (12.6 mmol) of sodium azide in 6.0 mL of DMF was heated at 50° C. under Ar overnight. After cooling to rt, the mixture was diluted with 40 mL of water, and extracted with two 75 mL portions of ether. The combined organic layers were washed thrice with water, brine, and dried over $MgSO_4$. The solvents were concentrated by distillation at atmospheric pressure to give a solution of the title compound in ether that was used directly in the next step.

Step D: 3-Cyclopropyl-2,2-difluoroproipylamine Hydrobromide

The solution of 3-cyclopropyl-2,2-difluoropropylazide from the previous step was diluted with 22 mL of ether, and 2.48 g (9.45 mmol) of triphenylphosphine was added. After the gas evolution had ceased, 227 µL (12.6 mmol) of water was added, and the reaction was heated to reflux under Ar for 6 h. The reaction mixture was dried over $MgSO_4$ and concentrated to approx. 10 mL by distillation at atm. pressure. This solution was treated with HBr gas which caused a ppt that was collected by filtration and washed with ether to give the title compound as a colorless solid:

$^1$H NMR (DMSO-d6) δ 8.24 (br s, 3H), 3.47 (t, 2H, 16.1 Hz), 1.92 (td, 2H, 16.8, 6.8 Hz), 0.75–0.85 (m, 1H), 0.47–0.57 (m, 2H), 0.17–0.23 (m, 2H).

Step E: Ethyl 3-(3-Cyclopropyl-2,2-difluoropropylamino)-6-methylpyrazin(1H)-2-one-1-acetate A mixture of 190 mg (1.0 mmol) of 3-cyclopropyl-2,2-difluoropropylamine hydrobromide, 302 mg (1.1 mmol) of ethyl 3-bromo-6-methylpyrazin(1H)-2-one-1-acetate and 304 mg (2.2 mmol) of finely ground potassium carbonate was heated to 85° C. in 3.5 mL of 1-methylpyrolidinone under Ar for 5 days. After cooling to rt, the reaction was partitioned between water and EtOAc, and the aqueous layer extracted with two portions of EtOAc. The combined organic layers were washed with three portions of water, brine, dried over $Na_2SO_4$ and the solvents removed by distillation at atm. pressure to give a concentrated solution of the title compound and starting materials. This solution was diluted with 2.0 mL of pyridine and heated to 100° C. under Ar overnight. After cooling to rt, the reaction was worked up as above and the solvents removed to give a dark brown oil that was chromatographed on 7 g of fine $SiO_2$ using 1:5 EtOAc-CHCl$_3$ to give the title compound as a yellow solid:

$^1$H NMR (CDCl$_3$) δ 6.72 (s, 1H), 6.09 (br t, 1H), 4.72 (s, 2H), 4.24 (q, 2H, 7.1 Hz 3.90 (td, 2H, 14.4, 6.1 Hz), 2.13 (s, 3H), 1.91 (td, 2H, 15.6, 7.1 Hz), 0.79–0.88 (m, 1H), 0.58–0.63 (m, 2H), 0.17–0.23 (m, 2H).

Step F: 3-(3-Cyclopropyl-2,2-difluoropropylamino)-6-methyl-1-(4-aza-5-methylenecarboxamidomethylindolyl)-pyrazinone bis TFA Salt The title compound was prepared using the procedures of Example 58, Step F followed by a standard coupling procedure:

Analysis calculated for $C_{21}H_{24}F_2N_6O_2 \cdot 2.3$ TFA, 0.75 H2O C, 43.54; H, 3.97; N, 11.90. Found: C, 43.55; H, 3.95; N, 11.90.

EXAMPLE 64

Tablet Preparation

Tablets containing 25.0, 50.0, and 100.0 mg., respectively, of the following active compounds are prepared as illustrated below (compositions A-I). Active I is 3-(2-Phenethylamino)-6-methyl-1-(5-methylcarboxamido-methyl-1,2,3-benzotriazolyl)-pyrazinone; Active II is 3-(2-Phenethylamino)-6-methyl-1-(5-methylcarboxamido-methyl-7-azaindolyl)-pyrazinone bis-TFA salt; Active III is 3-(2-Phenethylamino)-6-methyl-1-(5-methylcarboxamido-methyl-6-azaindolyl)-pyrazinone dihydrochloride; and Active IV is 3-(2-Phenethylamino)-6-methyl-1-(5-methylcarboxamido-methyl-6-aza-3-chloroindolyl)-pyrazinone bis-TFA salt.

|  | Amount-mg | | | | | | | | |
| --- | --- | --- | --- | --- | --- | --- | --- | --- | --- |
| Component | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 65

Tablet Preparation

Exemplary compositions of 3-(2-Phenethylamino)-6-methyl-1-(5-methylcarboxamido-methyl-6-aza-3- chloroindolyl)-pyrazinone bis-TFA Salt tablets are shown below:

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified particle size. The granules are then mixed with magnesium stearate and tabletted as stated above.

EXAMPLE 66

Intravenous Formulations

Intravenous formulations of were prepared according to general intravenous formulation procedures.

| Component | Estimated range |
|---|---|
| Active IV | 0.12–0.61 mg |
| D-glucuronic acid* | 0.5–5 mg |
| Mannitol NF | 50–53 mg |
| Water for injection | q.s. 1.0 mL |

1N Sodium hydroxide is used to achieve a solution pH in the range of between 3.9–4.1.
Exemplary compositions A–C are as follows:

| Component | A | B | C |
|---|---|---|---|
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |

-continued

| Component | A | B | C |
|---|---|---|---|
| 1N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base; 0.25 mg free base; *0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

EXAMPLE 67

5-Aminomethyl-1H-pyrazolo[3,4-c]pyridine Dihydrochloride

Step 1: 2,4-Dimethyl-5-nitropylidine

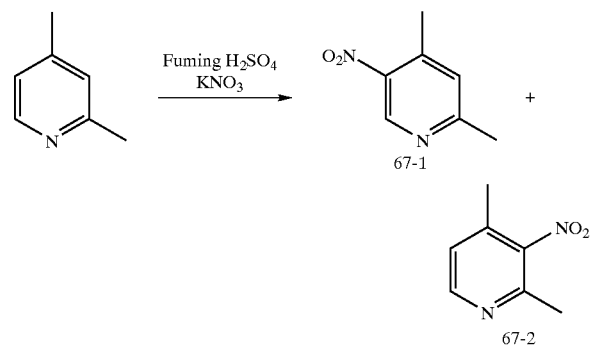

To 80 mL of fuming sulfuric acid at 0° C. was added in small portions 27 mL(233.3 mMol) of 2,4-lutidine. To this solution was added in small portions 47.2 g(466.6 mMol, 2 eq.) of potassium nitrate and the resulting solution was heated at 170° C. for 0.5 h. This was then poured into 1 L of ice and solid sodium bicarbonate was added in small portions with vigorous stirring until the pH was neutral. This was extracted with diethyl ether which was dried($Na_2SO_4$) and concentrated in vacuo. Purification by flash silica gel chromatography using methylene chloride as the eluent afforded a 3/2 mixture of 2,4-dimethyl-5-nitropyridine(1) and 2,4-dimethyl-3-nitropyridine(2) in the form of a yellow oil.

Step 2: 2,4-Dimethyl-5-aminopyridine

A 5.2 g(34.2 mMol) mixture of 2,4-dimethyl-5-nitropyridine(1) and 2,4-dimethyl-3-nitropyridine(2) dissolved in 100 mL of ethanol was shaken under 55 psi of hydrogen with 1.0 g of 10% palladium on carbon until hydrogen uptake ceased. The reaction was filtered through a bed of celite and the filtrate concentrated in vacuo. Purification by flash silica gel chromatography using methanol/methylene chloride as the eluent afforded 2,4-dimethyl-5-aminopyridine(3) in the form of a clear colorless oil.

Step 3: 2,4-Dimethyl-5-acetamidopyridine

To 2.5 g(20.5 mMol) of 2,4-dimethyl-5-aminopyridine(3) dissolved in 100 mL of chloroform at 25° C. under nitrogen atmosphere was added 2.0 mL(21.5 mMol, 1.05 eq) of acetic anhydride. The solution was stirred for 0.5 h and then was partitioned between methylene chloride and saturated sodium bicarbonate solution. The organic phase was dried (Na$_2$SO$_4$) and concentrated in vacuo to afford 2,4-dimethyl-5-acetamidopyridine(4) in the form of a yellow oil.

Step 4: 1-Acetyl-5-methylpyrazolo[3,4-c]pyridine

To 3.4 g(20.7 mMol) of 2,4-dimethyl-5-acetamidopyridine(4) dissolved in 140 mL of acetic anhydride and 55 mL of acetic acid at 25° C. under nitrogen atmosphere was added 3.05 g(31.1 mMol, 1.5 eq) of potassium acetate followed by 3.12 g(47.7 mMol, 2.3 eq) of nitrosyl chloride dissolved in 10 mL of acetic anhydride. The solution was stirred for 0.5 h and was then poured into a vigorously stirred suspension of solid sodium carbonate in 100 mL of benzene. The solid was filtered off and the filtrate refluxed for 1.5 h. The solution was concentrated in vacuo and the residue purified by flash silica gel chromatography using methanol/methylene chloride as the eluent to afford 1-acetyl-5-methylpyrazolo[3,4-c]pyridine(5) in the form of a yellow crystalline solid.

Step 5: 1-Acetyl-5-bromomethylpyrazolo[3,4-c]pyridine

To 2.0 g( 11.4 mMol) of 1-acetyl-5-methylpyrazolo[3,4-c]pyridine(5) in 300 mL of carbon tetrachloride under nitrogen atmosphere was added 2.03 g(11.4 mMol) of N-bromosuccinimide and 50 mg(0.3 mMol, 2.6 Mol %) of 2,2'-azobisisobutyronitrile. The solution was refluxed for 1 h and then concentrated in vacuo. Purification by flash silica gel chromatography using methanol/methylene chloride as the eluent afforded 1-acetyl-5-bromomethylpyrazolo[3,4-c]pyridine(6) in the form of an off white crystalline solid.

Step 6: 1-Acetyl-5-azidomethylpyrazolo[3,4-c]pyridine

To 1.4 g(5.51 mMol) of 1-acetyl-5-bromomethylpyrazolo[3,4-c]pyridine(6) in 8 mL of anhydrous N,N-dimethylformamide at 25° C. under nitrogen atmosphere was added 1.8 g(27.55 mMol, 5 eq) of sodium azide. The solution was stirred for 18 h at 25° C., concentrated in vacuo, then partitioned between methylene chloride and water. The organic phase was dried(Na$_2$SO$_4$) and concentrated in vacuo. Purification by flash silica gel chromatography using methanol/methylene chloride as the eluent afforded 1-acetyl-5-azidomethylpyrazolo[3,4-c]pyridine(7) in the form of a white crystalline solid.

Step 7: 5-Aminomethyl-1H-pyrazolo[3,4-c]pyridine Dihydrochloride

To 1.0 g(4.62 mMol) of 1-acetyl-5-azidomethylpyrazolo[3,4-c]pyridine(7) in 10 mL of tetrahydrofuran at 25° C. was added 5.5 mL(5.5 mMol, 1.2 eq) of 1 N sodium hydroxide solution. The solution was stirred for 0.5 h, 1.46 g(5.5 mMol, 1.2 eq) of triphenylphosphine was added, and the solution was refluxed for 2 h. The reaction was partitioned between diethyl ether and 1 N hydrochloric acid solution. The aqueous layer was concentrated in vacuo several times from methanol and the residue was triturated with diethyl ether and a minimal amount of methanol. The precipitate was filtered off to afford 5-aminomethyl-1H-pyrazolo[3,4-c]pyridine dihydrochloride(8) in the form of a yellow powder. $^1$H nmr (methanol-$d_4$): δ 9.59 (s, 1H), 8.65 (s, 1H), 8.51 (s, 1H), 4.64 (s, 2H).

EXAMPLE 68

3-Hydroxy-4-diisobutylaminocarbonyl-6-methyl-1-(4-azaindol-5-ylmethylaminocarbonylmethyl)-2-pyridinone

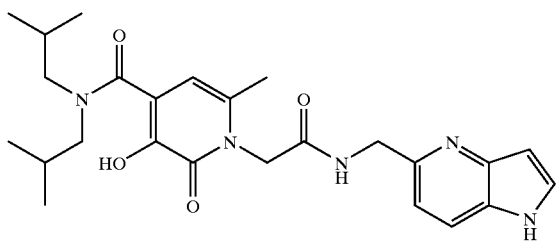

Step 1 3-Benzyloxy-4-ethoxycarbonyl-6-methyl-2-pyridinone

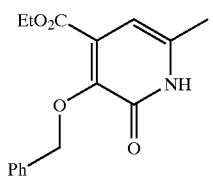

To a stirred solution of 3-hydroxy-4-ethoxycarbonyl-6-methyl-2-pyridinone (prepared by the method of Feist et al., Chem. Ber., 1902, vol. 35, p. 1545; 23.9 g, 121 mmol) and benzyl bromide (14.4 mL, 121 mmol) in DMF (400 mL) at 0° C. was added cesium carbonate (39.7, 121 mmol). The resulting mixture was stirred at 4° C. for 48 h. More benzyl bromide was added (2.8 mL, 24 mmol) and the mixture was stirred at 4° C. for another 72 h. The solvent was removed in vacuo and the residue was suspended in CH2Cl2. The solids were removed by filtration and the filtrate solvent was removed in vacuo. The residue was purified by flash column chromatography using 1:3 EtOAc:hexanes as eluant to give the title compound (18 g; HPLC RT=15.04 min, method B).

Step 2 3-Benzyloxy-4-ethoxycarbonyl-6-methyl-1-tert-butyloxycarbonylmethyl-2-pyridinone

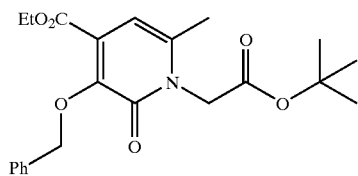

To a stirred solution of 3-benzyloxy-4-ethoxycarbonyl-6-methyl-2-pyridinone from step 1 above (17 g, 59 mmol) and tert-butyl bromoacetate (8.1 g, 59 mmol) in DMF (350 mL) at 0° C. was added cesium carbonate (19.3 g, 59 mmol). The mixture was stirred at 4° C. for 96 h. The salts were removed by filtration and the filtrate solvent was removed in vacuo. The residue was purified by flash column chromatography using 1:4 EtOAc:hexanes as eluant to give the title compound as an oil (9.5 g; HPLC RT=23.58, method B).

Step 3 3-Benzyloxy-4-carboxy-6-methyl-1-tert-butyloxycarbonylmethyl-2-pyridinone

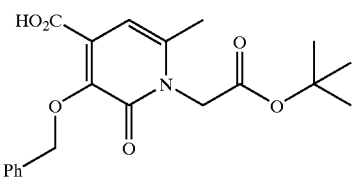

To a solution of 3-benzyloxy-4-ethoxycarbonyl-6-methyl-1-tert-butyloxycarbonylmethyl-2-pyridinone from step 2 above (1.1 g, 2.8 mmol) in 1:1 THF:H2O (20 mL) was added aqueous LiOH (3.0 mL of a 1.1 N solution, 3.3 mmol) and the resulting solution was stirred at ambient temperature for 18 h. Aqueous HCl was added (3 mL of a 1 N solution, 3 mmol) and the solvents were removed in vacuo. The residue was partitioned between water and EtOAc. The organic layer was separated and the aqueous layer was extracted four times with EtOAc. The combined organic phases were dried over Na2SO4, filtered, and the solvent was removed in vacuo to give the title compound as an amorphous solid (0.91 g; HPLC RT=15.98 min, method B).

Step 4 3-Benzyloxy-4-diisobutylaminocarbonyl-6-methyl-1-tert-butyloxycarbonylmethyl-2-pyridinone

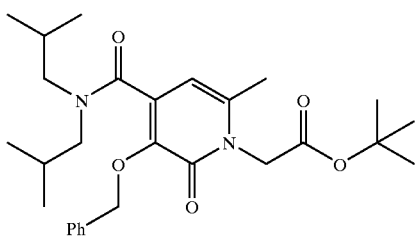

To a stirred solution of 3-benzyloxy-4-carboxy-6-methyl-1-tert-butyloxycarbonylmethyl-2-pyridinone from step 3 above (0.91 g, 2.3 mmol) in DMF (6 mL) was added diisobutylamine (0.48 mL, 2.8 mmol), HATU (1.76 g, 4.6 mmol), and DIEA (0.45 mL, 2.6 mmol). The resulting solution was stirred at ambient temperature for 18 h. The solvents were removed in vacuo and the residue was purified by flash column chromatography using a gradient elution of 25–50% EtOAc:hexanes to give the title compound as an oil (0.80 g; HPLC RT 24.80 min, method B).

Step 5 3-Hydroxy-4-diisobutylaminocarbonyl-6-methyl-1-tert-butyloxycarbonylmethyl-2-pyridinone

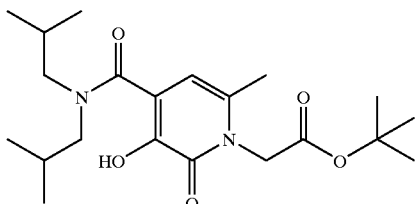

A mixture of 3-benzyloxy-4-diisobutylaminocarbonyl-6-methyl-1-tert-butyloxycarbonylmethyl-2-pyridinone from step 4 above (0.80 g) and 10% Pd on carbon (180 mg) in ethanol (40 mL) was shaken on a Parr apparatus under an atmosphere of hydrogen (50 psi) for 18 h. The catalyst was removed by filtration and the filtrate solvents were removed in vacuo to give the title compound (0.608 g;

HPLC RT=20.14 min, method B).

Step 6 3-Hydroxy-4-diisobutylaminocarbonyl-6-methyl-1-carboxymethyl-2-pyridinone

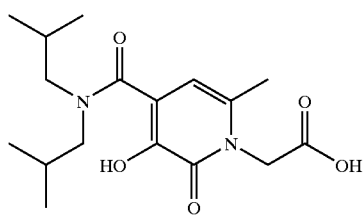

To a solution 3-hydroxy-4-diisobutylaminocarbonyl-6-methyl-1-tert-butyloxycarbonylmethyl-2-pyridinone from step 5 above (0.61 g) in CH2Cl2 (4 mL) was added TFA (2 mL) and the solution was stirred at ambient temperature for 32 h. The solvents were removed in vacuo to give the title compound (0.6 g; HPLC RT=13.56 min, method B).

Step 7 3-Hydroxy-4-diisobutylaminocarbonyl-6-methyl-1-(4-azaindol-5-ylmethylaminocarbonylmethyl)-2-pyridinone

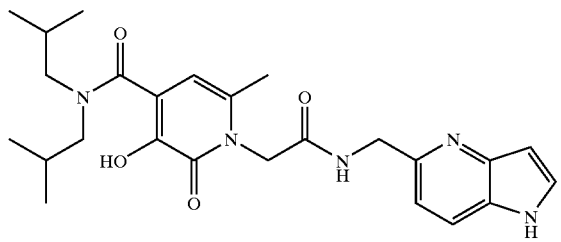

To a solution of 3-hydroxy-4-diisobutylaminocarbonyl-6-methyl-1-carboxymethyl-2-pyridinone from step 6 above (96 mg, 0.28 mmol) in DMF (1 mL) was added 5-aminomethyl-4-azaindole bis-hydrochloride (65 mg, 0.31 mmol), HOBT (42 mg, 0.31 mmol), N-methylmorpholine (0.060 mL, 0.4 mmol), and EDC (163 mg, 0.56 mmol). The reaction was stirred at ambient temperature for 24 h, concentrated in vacuo, and purified by preparative reverse phase HPLC using a gradient elution of 99:1:0.1 to 40:60:0.1 H2O:CH3CN:TFA. The fractions containing product were combined and lyophilized to give the TFA salt of the title compound as an amorphous solid (52 mg; HPLC RT=12.65 min, method B; CHN calcd for $C_{25}H_{33}N_5O_4$, 1.35 TFA, 0.05 $H_2O$: C 53.45, H 5.58, N11.25; found C 53.45, H 5.33, N 11.43).

EXAMPLE 69

3-Acetyl-4-(2-isopropylphenyl)-6-methyl-1-(6-azaindol-5-ylmethylaminocarbonylmethyl)-2-pyridinone

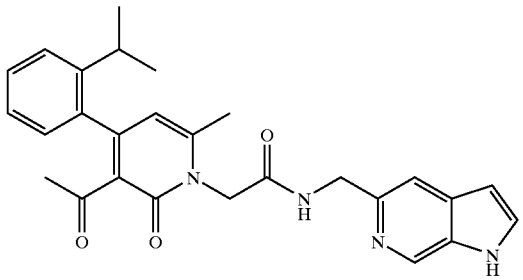

Step 1 3-Acetyl-4-(2-isopropylphenyl)-6-methyl-1-carboxymethyl-2-pyridinone

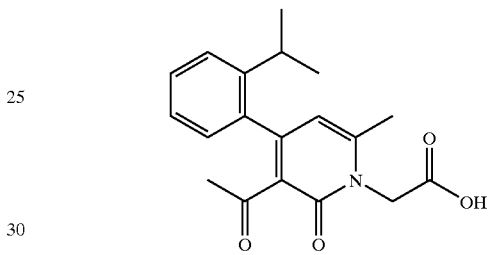

To a stirred solution of 3-acetyl-4-(2-isopropylphenyl)-6-methyl-1-ethoxycarbonylmethyl-2-pyridinone from step 3 of Example XX (0.20 g, 0.56 mmol) in ethanol (4 mL) was added aqueous NaOH (0.62 mL of a 1.0 N solution, 0.62 mmol). The resulting solution was stirred at ambient temperature for 2 h and the solvent was removed in vacuo. The residue was partitioned between EtOAc and 1.0 N aqueous HCl. The organic phase was separated and the aqueous phase was extracted with EtOAc. The combined organic extracts were dried over $Na_2SO_4$, filtered, and concentrated in vacuo to give the title compound (HPLC RT=18.11 min, method B).

Step 2 3-Acetyl-4-(2-isopropylphenyl)-6-methyl-1-(6-azaindol-5-ylmethylaminocarbonylmethyl)-2-pyridinone

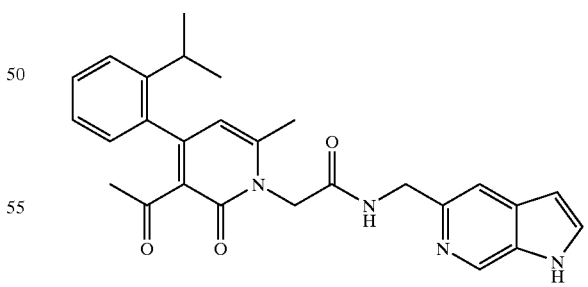

To a stirred solution of 3-acetyl-4-(2-isopropylphenyl)-6-methyl-1-carboxylmethyl-2-pyridinone from step 1 above (0.047 g, 0.14 mmol) in DMF (2 mL) was added 5-aminomethyl-6-azaindole bis-hydrochloride salt (41 mg, 0.16 mmol) and HOBT (30 mg, 0.17 mmol). The solution was brought to pH 7 by the addition of DIEA (approximately 0.1 mL). EDC (40 mg, 0.21 mmol) was added and the solution was stirred at ambient temperature for 3 h. The reaction was concentrated in vacuo and purified by preparative reverse phase HPLC using a gradient elution of 95:5:0.1 to 40:60:0.1 H2O:CH3CN:TFA. The fractions containing the desired product were combined and lyophilized to give the TFA salt of the title compound as an amorphous solid (25 mg, HPLC RT=17.23 min, method B; CHN calcd for $C_{27}H_{28}N_4O_3$, 1.1 TFA, 0.65 H2: C, 59.07, H, 5.16, N, 9.44; found C, 59.07, H, 5.15, N, 9.24).

EXAMPLE 70

3-Hydroxy-4-(2-isopropylphenyl)-6-methyl-1-(3-chloro-6-azaindol-5-ylmethylaminocarbonylmethyl)-2-pyridinone

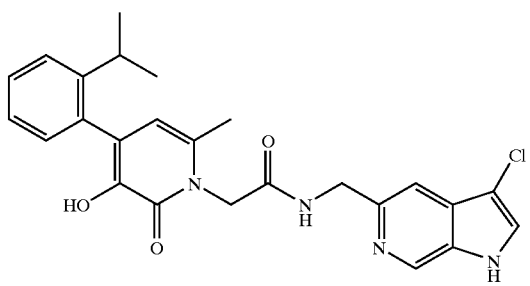

Step 1 3-Acetyl-4-hydroxy-6-methyl-1-ethoxycarbonylmethyl-2-pyridinone

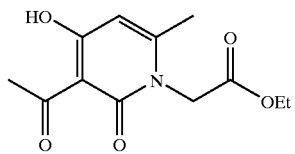

Into a stirred solution of 3-acetyl-4-hydroxy-6-methyl-1-carboxymethyl-2-pyridinone prepared by the method of Garratt and Shemin, *J. Org. Chem.* 1963, vol. 28, p. 1372 (2.3 g) in EtOH (60 mL) at 0° C. was bubbled HCl gas for 30 min. The resulting solution was stirred at 0° C. for 1 h and then at ambient temperature for 18 h. The solvent was removed in vacuo to give the title compound as a solid (2.7 g; HPLC RT=13.06 min, method B).

Step 2 3-Acetyl-4-trifluoromethylsulfonyloxy-6-methyl-1-ethoxycarbonylmethyl-2-pyridinone

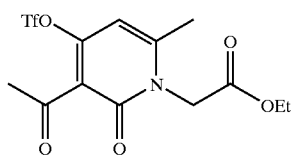

To a stirred solution of 3-acetyl-4-hydroxy-6-methyl-1-ethoxycarbonylmethyl-2-pyridinone from step 1 above (2.68 g, 10.5 mmol) in CH2Cl2 (25 mL) at 0° C. was added pyridine (2.4 mL, 31 mmol) and trifluoromethanesulfonic anhydride (2.67 mL, 15 mmol). The resulting solution was stirred at 0° C. for 2 h and then diluted with CH2Cl2 and water. The organic phase was separated, washed with water three times, dried over Na2SO4, filtered, and concentrated in vacuo. The residue was purified by flash column chromatography using 1:2 EtOAc:hexanes as eluant to give the title compound (HPLC RT=19.80 min, method A).

Step 3 3-Acetyl-4-(2-isopropylphenyl)-6-methyl-1-ethoxycarbonylmethyl-2-pyridinone

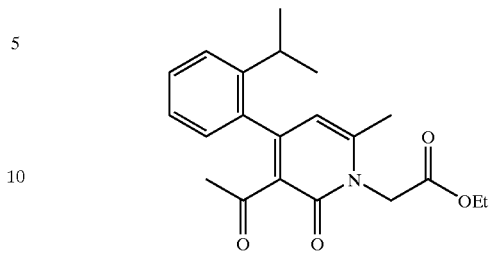

A mixture of 3-acetyl-4-trifluoromethylsulfonyloxy-6-methyl-1-ethoxycarbonylmethyl-2-pyridinone from step 2 above (2.5 g, 7.2 mmol), 2-isopropylbenzeneboronic acid (1.8 g, 11 mmol), potassium carbonate (1.5 g, 11 mmol), and Pd(PPh3)4 (1.7 g, 1.4 mmol) was heated to reflux under inert atmosphere for 3 h. The solvent was removed under reduced pressure and the residue was purified by flash column chromatography using a gradient elution of 25–75% EtOAc:hexanes to give the title compound (0.72 g; HPLC RT=21.79 min, method B).

Step 4 3-Acetoxy-4-(2-isopropylphenyl)-6-methyl-1-ethoxycarbonylmethyl-2-pyridinone

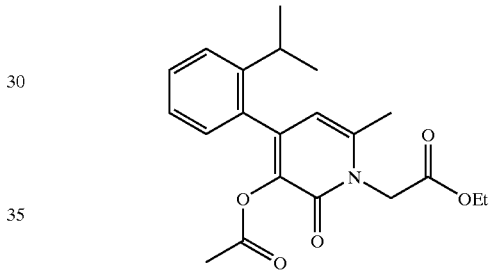

To a stirred solution of 3-acetyl-4-(2-isopropylphenyl)-6-methyl-1-ethoxycarbonylmethyl-2-pyridinone from step 3 above (0.65 g, 1.8 mmol) in CH2Cl2 (150 mL) at 0° C. was added 30% aqueous H2O2 (0.94 mL, 9 mmol) and trifluoroacetic anhydride (1.8 mL, 14 mmol). The resulting solution was refluxed for 1 h and then diluted with CH2Cl2 and water. The organic phase was separated, dried over Na2SO4, filtered, and concentrated in vacuo to give the title compound (0.325 g; NMR: OCOCH3 peak at 2.05 ppm; HPLC RT=22.81 min, method B).

Step 5 3-Hydroxy-4-(2-isopropylphenyl)-6-methyl-1-carboxymethyl-2-pridinone

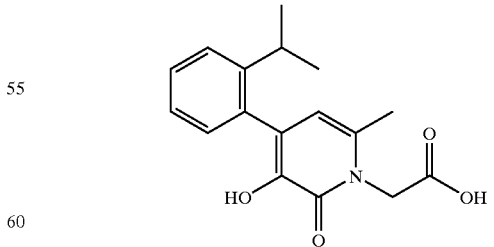

To a stirred solution of 3-acetoxy-4-(2-isopropylphenyl)-6-methyl-1-ethoxycarbonylmethyl-2-pyridinone from step 4 above (0.325 g, 0.95 mmol) in ethanol (4 mL) was added aqueous NaOH (2.2 mL of a 1.0 N solution, 2.2 mmol). The resulting solution was stirred at ambient temperature for 18 h. The solution was acidified with aqueous HCl (2.2 mL of a 1.0 N solution, 2.2 mmol) and the solvents were removed in vacuo to give the title compound as an amorphous solid containing NaCl (HPLC RT=18.67 min, method B).

Step 6 3-Hydroxy-4-(2-isopropylphenyl)-6-methyl-1-(3-chloro-6-azaindol-5-ylmethylaminocarbonylmethyl)-2-pyridinone

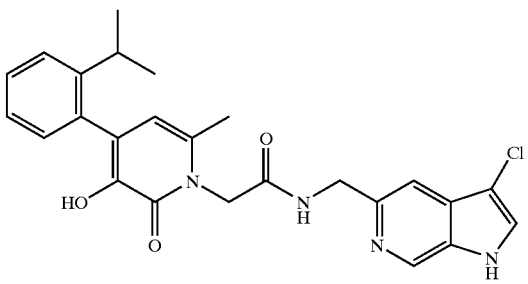

To a stirred solution of 3-hydroxy-4-(2-isopropylphenyl)-6-methyl-1-carboxymethyl-2-pyridinone from step 5 above (0.38 mmol) in DMF (3 mL) was added 5-aminomethyl-3-chloro-6-azaindole bis-hydrochloride salt (106 mg, 0.42 mmol) and HOBT (55 mg, 0.42 mmol). The solution was brought to pH 7 by the addition of DIEA (approximately 0.2 mL). EDC (170 mg, 0.65 mmol) was added and the solution was stirred at ambient temperature for 18 h. The reaction was concentrated in vacuo and purified by preparative reverse phase HPLC using a gradient elution of 95:5:0.1 to 35:65:0.1 H$_2$O:CH$_3$CN:TFA. The fractions containing the desired product were combined and lyophilized to give the TFA salt of the title compound as an amorphous solid (40 mg, HPLC RT=20.69 min, method B; CHN calcd for C$_{25}$H$_{25}$ClN$_4$O$_3$, 1.2 TFA, 0.2 H2O: C, 54.36, H, 4.43, N, 9.26; found C, 54.33 H, 4.47, N, 9.25).

EXAMPLE 71

4-(1-(2-Hydroxy-2-methylpropyl)-cis-3-phenylpyrrolidin-4-yl)-6-methyl-1-(3-fluoro-7-azaindol-5-ylmethylaminocarbonylmethyl)-2-pyridinone

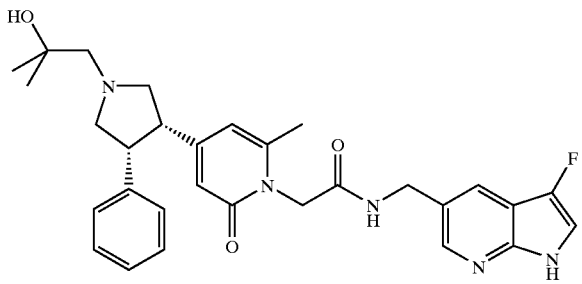

Step 1 4-Hydroxy-6-methyl-1-ethoxycarbonylmethyl-2-pybrdinone

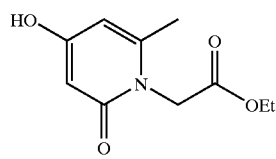

Into a stirred solution of 4-hydroxy-6-methyl-lI-carboxymethyl-2-pyridinone (prepared by the method of Garratt and Shemin, *J. Org. Chem.* 1963, vol. 28, p. 1372; 20 g, 95 mmol) in ETOH (300 mL) at 0° C. was bubbled HCl gas for 20 min. The solution was warmed to ambient temperature and stirred for 48 h. The solvent was removed in vacuo and the residue was triturated in ether to give the title compound as a white solid (18 g; HPLC RT=3.7 min, method A).

Step 2 4-Trifluoromethylsulfonyloxy-6-methyl-1-ethoxycarbonylmethyl-2-pyrdinone

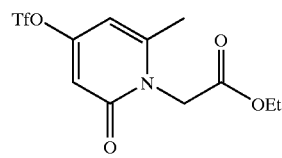

To a stirred solution of 4-hydroxy-6-methyl-1-ethoxycarbonylmethyl-2-pyridinone from step 1 above (10 g, 42 mmol) and pyridine (6.8 mL, 84 mmol) in CH2Cl2 (150 mL) at 0° C. was added trifluoromethanesulfonic anhydride (14 g, 50 mmol). The resulting solution was stirred at 0° C. for 4 h and then at ambient temperature for 4 h. Aqueous NaHCO3 was added and the organic phase was separated, dried over MgSO4, filtered, and concentrated in vacuo. The residue was purified by flash column chromatography using a gradient elution of 33–67% EtOAc:hexanes to give the title compound as an amorphous solid (11 g; HPLC RT=7.77 min, method A).

Step 3 4-Phenylethynyl-6-methyl-1-ethoxycarbonylmethyl-2-pyridinone

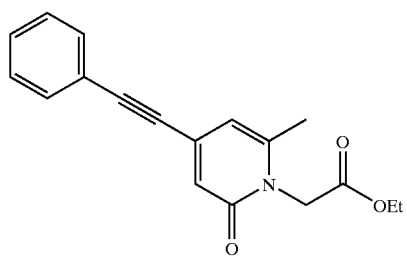

A solution of 4-trifluoromethylsulfonyloxy-6-methyl-1-ethoxycarbonylmethyl-2-pyridinone from step 2 above (2.0 g, 5.4 mmol), phenylacetylene (1.1 g, 11 mmol), triethylamine (3.6 mL, 25 mmol), and PdCl2(PPh3)2 (0.42 g, 0.6 mmol) in DMF (20 mL) was heated to 90° C. under inert atmosphere for 1 h. The solvent was removed in vacuo and the residue was partitioned between EtOAc and aqueous NaHCO3. The organic phase was separated, dried over MgSO4, filtered, and concentrated in vacuo. The residue was purified by flash column chromatography using 1:1 EtOAc:hexanes as eluant to give the title compound as an amorphous solid (1.5 g; TLC Rf=0.35, 1:1 EtOAc:hexanes; HPLC RT=8.64 min, method A).

Step 4 4-(cis-2-Phenylethenyl)-6-methyl-1-ethoxycarbonylmethyl-2-pyridinone

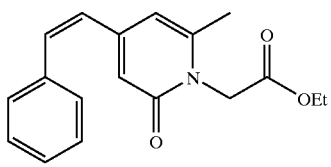

A mixture of 4-phenylethynyl-6-methyl-1-ethoxycarbonylmethyl-2-pyridinone from step 3 above (1.5 g, 4.6 mmol) and Lindlar catalyst (5%Pd on CaCO3 plus Pb;150 mg) in EtOH (25 mL) was stirred under an atmosphere of hydrogen at ambient pressure and temperatue for 1 h. The catalyst was removed by filtration and the filtrate solvent was removed in vacuo to give the title compound as a mixture containing 20% of the fully saturated (phenethyl) derivative (1.5 g; TLC Rf=0.5, 1:1 EtOAc:hexanes; HPLC RT=8.15 min, method A).

Step 5 4-(1-Benzyl-cis-3-phenylpyrrolidin-4-yl)-6-methyl-1-ethoxycarbonylmethyl-2-pyridinone

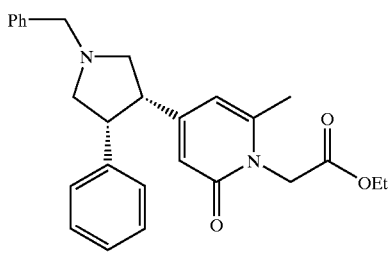

To a stirred solution of 4-(cis-2-phenylethenyl)-6-methyl- 3.1 mmol) and N-trimethylsilylmethyl-N'-methoxymethylbenzylamine (1.4 g, 6.1 mmol; prepared according to the method of Terao et al., *Chem. Pharm. Bull.*, 1985, vol. 33, p. 2762) in CH2Cl2 (25 mL) at 0° C. was added trifluoroacetic acid (0.1 g, 0.85 mmol). The resulting solution was stirred at 0° C. for 4 h and then at ambient temperature for 18 h. Aqueous NaHCO$_3$ was added and the organic phase was separated, dried over MgSO$_4$, filtered, and concentrated in vacuo. The residue was purified by flash column chromatography using a gradient elution of 50–90% EtOAc:hexanes to give the title compound as an oil (1.1 g; TLC Rf=0.4, EtOAc; HPLC RT 6.34, method A).

Step 6 4-(cis-3-Phenylpyrrolidin-4-yl)-6-methyl-1-ethoxycarbonylmethyl-2-pyridinone

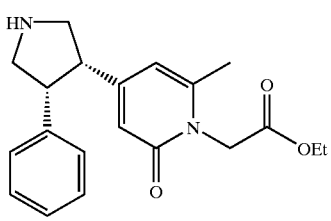

A mixture of 4-(1-benzyl-cis-3-phenylpyrrolidin-4-yl)-6-methyl-1-ethoxycarbonylmethyl-2-pyridinone from step 5 above (0.30 g, 0.66 mmol), 10% Pd on carbon (100 mg), and HOAc (1 mL) in EtOH (10 mL) was stirred under an atmosphere of hydrogen at ambient pressure and temperature for 24 h. The catalyst was removed by filtration and the filtrate solvent was removed in vacuo. The residue was partitioned between CH$_2$Cl$_2$ and aqueous NaHCO$_3$. The organic phase was separated, dried over MgSO$_4$, filtered, and the solvent was removed in vacuo to give the title compound as an oil (0.2 g, HPLC RT=4.98 min, method A).

Step 7 4-(1-(2-Hydroxy-2-methylpropyl)-cis-3-phenylpyrrolidin-4-yl)-6-methyl-1-ethoxycarbonylmethyl-2-pyridinone

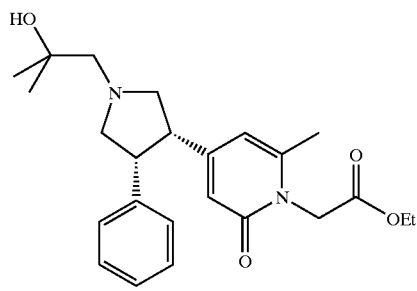

A solution of 4-(cis-3-phenylpyrrolidin-4-yl)-6-methyl-1-ethoxycarbonylmethyl-2-pyridinone from step 6 above (0.2 g, 0.54 mmol) and isobutylene oxide (1 mL) in EtOH (4 mL) was heated to reflux for 1 h. The solvent was removed in vacuo and the residue was purified by flash column chromatography using 96:4:0.2 CH$_2$Cl$_2$:MeOH:NH$_4$OH as eluant to give the title compound as an oil (0.17 g; TLC Rf=0.3, 96:4:0.2 CH$_2$Cl$_2$:MeOH:NH$_4$OH; HPLC RT=5.08 min, method A).

Step 8 4-(1-(2-Hydroxy-2-methylpropyl)-cis-3-phenylpyrrolidin-4-yl)-6-methyl-1-carboxymethyl-2-pyridinone

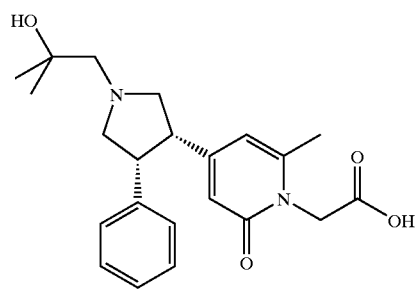

A solution of 4-(1-(2-hydroxy-2-methylpropyl)-cis-3-phenylpyrrolidin-4-yl)-6-methyl-1-ethoxycarbonylmethyl-2-pyridinone from step 7 above (0.10 g, 0.23 mmol) and aqueous NaOH (0.11 mL of a 4.0N solution, 0.46 mmol) was stirred at ambient temperature for 18 h. Aqueous HCl was added (0.076 mL of a 6.0 N solution, 0.46 mmol) and the solvents were removed in vacuo to give the title compound as an amorphous solid mixed with NaCl (HPLC RT=3.94 min, method A).

Step 9 4-(1-(2-Hydroxy-2-methylpropyl)-cis-3-phenylpyrrolidin-4-yl)-6-methyl-1-(3-fluoro-7-azaindol-5-ylmethylaminocarbonylmethyl)-2-pyridinone

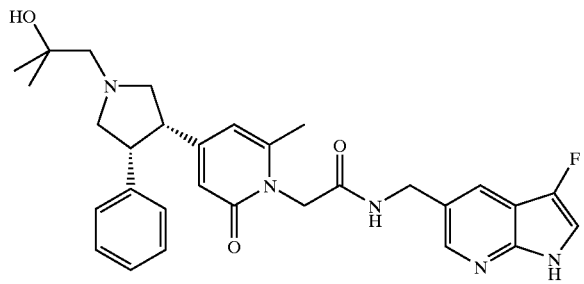

To a stirred solution of 4-(1-(2-hydroxy-2-methylpropyl)-cis-3-phenylpyrrolidin-4-yl)-6-methyl-1-carboxymethyl-2-pyridinone from step 8 above (0.23 mmol), 5-aminomethyl-3-fluoro-7-azaindole bis hydrochloride (55 mg, 0.23 mmol), HOBT (35 mg, 0.23 mmol) and DIEA (0.12 mL, 0.69 mmol) in DMF (2 mL) was added EDC (134 mg, 0.46 mmol). The resulting solution was stirred at ambient temperature for 18 h. The solvent was removed in vacuo and the residue was purified by flash column chromatography using a gradient elution of 96:4 to 92:8 CH2Cl2:MeOH as eluant to give the title compound as an amorphous solid (0.1 g, TLC Rf=0.4, 92:8 CH$_2$Cl$_2$:MeOH; HPLC RT=4.71 min, method A).

EXAMPLE 72

3-(2-Ethylpyrid-3-ylamino)-6-methyl-1-(6-azaindol-5-ylmethylaminocarbonylmethyl)pyrazinone

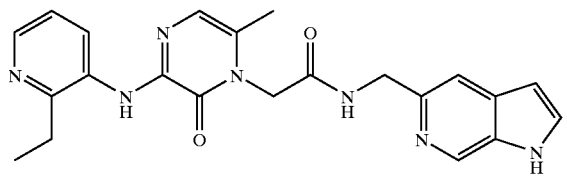

Step 1: 2-Vinyl-3-nitropyridine

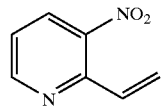

Into a solution of the commercially available 2-chloro-3-nitropyridine (2 g, 12.6 mMol) in 5 mL of anhydrous N,N-dimethylformamide under inert atmosphere was added tributyl(vinyl)tin (4 mL, 13.87 mMol, 1.1 eq), lithium chloride (2.68 g, 50.46 mMol, 5 eq), and dichlorobis(triphenylphosphine)-palladium(II) (442 mg, 0.64 mMol, 5 Mol %). This was heated for 18 h at 90° C., concentrated in vacuo, and purified by flash silica gel chromatography using 10% ethyl acetate in hexanes as an eluent to afford the title compound as a brown oil (0.75 g).

Step 2: 2-Ethyl-3-aminopyridine

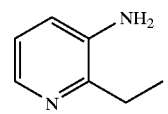

A solution of 2-vinyl-3-nitropyridine (0.75 g, 5.0 mMol) from step 1 above dissolved in 50 mL of ethanol and 100 mg of 10% palladium on carbon was shaken under 55 psi of hydrogen using a parr hydrogenation apparatus until hydrogen uptake ceased. The mixture was filtered through a bed of celite and the filtrate concentrated in vacuo. The residue was purified by flash silica gel chromatography using 1% then 2% methanol in methylene chloride as an eluent to afford the title compound as a white crystalline solid (0.35 g).

Step 3: 3-(2-Ethylpyrid-3-ylamino)-6-methyl-1-(ethoxycarbonylmethyl)pyrazinone

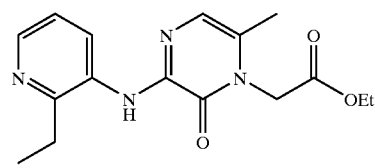

A mixture of 2-ethyl-3-aminopyridine (0.35 g, 2.8 mMol, 2 eq) from step 2 above and 3-bromo-6-methyl-1-(ethoxycarbonylmethyl)pyrazinone (0.39 g, 1.4 mMol) in 1 mL of nitrobenzene was heated at 200 ° C. for 2 h. The reaction was concentrated in vacuo and the residue purified by flash silica gel chromatography using 1% methanol in methylene chloride as an eluent to afford the title compound as a yellow oil that crystallizes upon sitting. (0.058 g; HPLC RT=4.45 min, method A).

Step 4: 3-(2-Ethylpyrid-3-ylamino)-6-methyl-1-(carboxymethyl)pyrazinone

To a solution of 3-(2-Ethylpyrid-3-ylamino)-6-methyl-1-(ethoxycarbonylmethyl)pyrazinone (0.058 g, 0.183 mMol) from step 3 above in 6 mL of 1:1:1-tetrahydrofuran:methanol:water was added 183 µL (0.183 mMol) of 1N sodium hydroxide solution. The solution was stirred at ambient temperature for 18 h at which time 183 µL (0.183 mMol) of 1N hydrochloric acid solution was added. The solution was concentrated in vacuo several times from methanol and the residue was triturated with diethyl ether. The resulting precipitate was filtered off to afford the title compound as a beige powder (0.039 g; HPLC RT=3.13 min, method A).

Step 5: 3-(2-Ethylpyrid-3-ylamino)-6-methyl-1-(6-azaindol-5-ylmethylaminocarbonylmethyl)pyrazinone

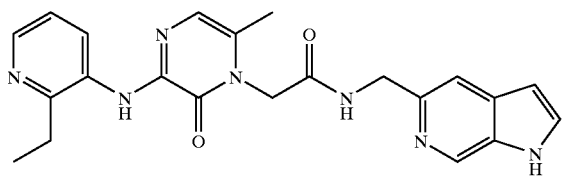

To a solution of 3-(2-Ethylpyrid-3-ylamino)-6-methyl-1-(carboxymethyl)pyrazinone (0.039 g, 0.135 mMol) from step 4 above in 5 mL of anhydrous N,N-dimethylformamide under inert atmosphere was added 5-aminomethyl-6-azaindole (0.035 g, 0.16 mMol, 1.2 eq), 1-hydroxybenzotriazole hydrate (0.024 g, 0.149 mMol, 1.1 eq), diisopropylethylamine (55 µL, 0.27 mMol, 2 eq), and 1-(3-dimethylaminopropyl)-3-ethylcarbodiimide hydrochloride (0.046 g, 0.20 mMol, 1.5 eq). This stirred at ambient temperature for 72 h and was concentrated in vacuo. This was purified by preparative reverse phase HPLC using a 99:1 to 50:50 (water:acetonitrile) gradient over 60 minutes. The desired fraction was concentrated in vacuo several times from methanol and the residue was crystallized from methanol-diethyl ether to afford the title compound as the TFA salt in the form of a white powder (0.034 g; HPLC RT=3.52 min, method A). $^1$H nmr (methanol-d$_4$): 9.4 (d, 1H), 8.98 (s, 1H), 8.37 (d, 1H), 8.19 (d, 1H), 8.09 (s, 1H), 7.86 (m, 1H), 6.95 (d, 1H), 6.93 (s, 1H), 4.95 (s, 2H), 4.79 (s, 2H), 3.15 (q, 2H), 2.28 (s, 3H), 1.4 (t, 2H).

EXAMPLE 73

3-(trans-3-Cyclopropylmethoxytetrahydrofuran-4-ylamino)-6-chloro-1-(3-chloro-7-azaindol-5-ylmethylaminocarbonylmethyl)pyrazinone

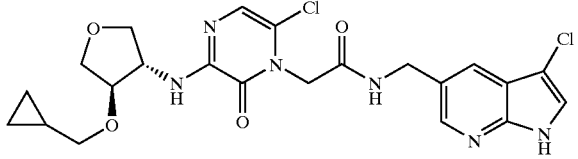

Step 1  cis-3-Cyclopropylmethoxy-4-hydroxytetrahydrofuran

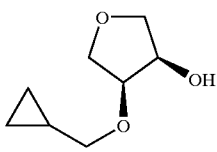

To a stirred solution of cis-3,4-dihydroxytetrahydrofuran (5.8 g, 56 mmol) and bromomethylcyclopropane (5.0 g, 37 mmol) in DMF (100 mL) at 0° C. was added sodium hydride (1.6 g of a 60% suspension in mineral oil, 40 mmol) in portions over a period of 2 h. The resulting solution was stirred at 0° C. for 1 h and then at ambient temperature for 18 h. The solution was concentrated in vacuo and partitioned between EtOAc and water. The organic phase was separated, dried over MgSO$_4$, filtered, and concentrated in vacuo. The residue was purified by flash column chromatography using 1:1 EtOAc:hexanes as eluant to give the title compound as a colorless liquid (1.8 g; TLC Rf=0.4, 1:1 EtOAc:hexanes).

Step 2  cis-3-Cyclopropylmethoxy-4-trifluoromethylsulfonyloxytetrahydrofuran

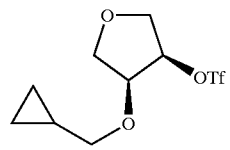

To a stirred solution of cis-3-cyclopropylmethoxy-4-hydroxytetrahydrofuran from step 1 above (1.6 g, 10 mmol) and pyridine (2.4 mL, 30 mmol) in CH$_2$Cl$_2$ (40 mL) at 0° C. was added trifluoromethanesulfonic anhydride (3.7 g, 13 mmol). The resulting solution was stirred at 0° C. for 2 h and then at ambient temperature for 1 h. Aqueous NaHCO$_3$ was added and the organic phase was separated, dried over MgSO$_4$, filtered, and concentrated in vacuo. The residue was purified by flash column chromatography using 1:9 EtOAc:hexanes as eluant to give the title compound as an oil (2.2 g; TLC Rf=0.7, 1:4 EtOAc:hexanes).

Step 3  trans-3-Cycloypropylmethoxy-4-azidotetrahydrofuran

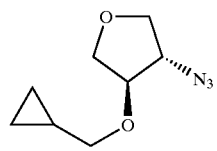

A solution of cis-3-cyclopropylmethoxy-4-trifluoromethylsulfonyloxytetrahydrofuran from step 2 above (2.2 g, 7.6 mmol) and sodium azide (1.3 g, 20 mmol) in DMF (20 mL) was stirred at ambient temperature for 18 h. The solvent was removed in vacuo and the residue was partitioned between EtOAc and water. The organic phase was separated, dried over MgSO$_4$, filtered, and concentrated in vacuo. The residue was purified by flash column chromatography using 1:4 EtOAc:hexanes as eluant to give the title compound as an oil (1.2 g; TLC Rf=0.5, 1:4 EtOAc:hexanes).

Step 4  trans-3-Cyclopropylmethoxy-4-aminotetrahydrofuran

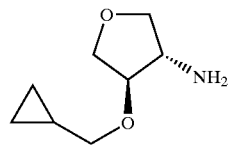

A solution of trans-3-cyclopropylmethoxy-4-azidotetrahydrofuran from step 3 above (1.2 g, mmol, 6.55 mmol) and 10% Pd on carbon (150 mg) in EtOAc (35 mL) was stirred under an atmosphere of hydrogen at ambient pressure and ambient temperature for 6 h. The catalyst was removed by filtration and the filtrate solvents were removed in vacuo to give the title compound as an oil (1.1 g, TLC Rf=0.3, 95:5:0.25 CH2Cl2:MeOH:NH$_4$OH).

Step 5 3-(trans-3-Cyclopropylmethoxytetrahydrofuran-4-ylamino)-1-ethoxycarbonylmethylpyrazinone

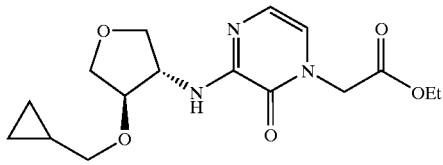

A stirred solution of trans-3-cyclopropylmethoxy-4-aminotetrahydrofuran from step 4 above (1.1 g, 7.0 mmol), 3-bromo-1-ethoxycarbonylmethylpyrazinone (1.8 g, 7.0 mmol), and DIEA (1.4 mL, 8.0 mmol) in toluene (20 mL) was heated to reflux for 24 h. The mixture was cooled to ambient temperature, diluted with EtOAc, and washed with aqueous NaHCO$_3$. The organic phase was separated, dried over MgSO$_4$, filtered, and concentrated in vacuo. The residue was purified by flash column chromatography using a gradient elution of 50–67% tOAc:hexanes to give the title compound as an amorphous solid (1.4 g; TLC Rf=0.4, 3:2 EtOAc:hexanes; HPLC RT=5.05 min, method A).

Step 6 3-(trans-3-Cyclopropylmethoxytetrahydrofuran-4-ylamino)-6-chloro-1-ethoxycarbonylmethylpyrazinone

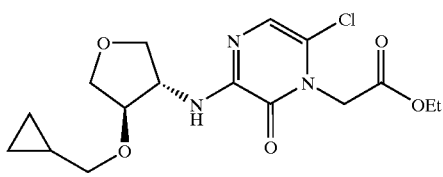

A stirred solution of 3-(trans-3-cyclopropylmethoxytetrahydrofuran-4-ylamino)-1-ethoxycarbonylmethylpyrazinone from step 5 above (1.4 g, 4.15 mmol) and N-chlorosuccinimide (0.61 g, 4.57 mmol) in CHCl3 was heated to reflux for 6 h. More N-chlorosuccinimide (0.11 g, 0.83 mmol) was added and refluxing was continued for an additional 6 h. The reaction was diluted with CHCl$_3$ and washed with aqueous NaHCO$_3$. The organic phase was separated, dried over Mg SO$_4$, filtered, and concentrated in vacuo. The residue was purified by flash column chromatography using a gradient elution of 25–50% EtOAc:hexanes to give the title compound as an amorphous solid (1.1 g, TLC Rf=0.5, 1:1 EtOAc:hexanes; HPLC RT=7.97 min, method A).

Step 7 3-(trans-3-Cyclopropylmethoxytetrahydrofuran-4-ylamino)-6-chloro-1-carboxymethylpyrazinone

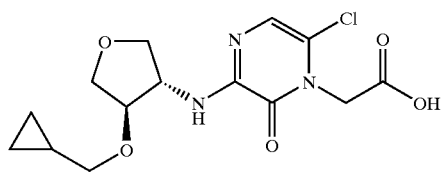

To a stirred solution of 3-(trans-3-cyclopropylmethoxytetrahydrofuran-4-ylamino)-6-chloro-1-ethoxycarbonylmethylpyrazinone from step 6 above (0.5 g, 1.3 mmol) and aqueous NaOH (0.65 mL of a 4.0 N solution, 2.6 mmol) in EtOH (7 mL) was stirred at ambient temperature for 18 h. Aqueous HCl (0.43 mL of a 6.0 N solution, 2.6 mmol) was added and the solvents were removed in vacuo. The residue was partitioned between CH$_2$Cl$_2$ and water. The organic phase was separated, dried over MgSO$_4$, filtered and the solvent was removed in vacuo to give the title compound as an amorphous solid (0.4 g; HPLC RT=5.88 min, method A).

Step 8 3-(trans-3-Cyclopropylmethoxytetrahydrofuran-4-ylamino)-6-chloro-1-(3-chloro-7-azaindol-5-ylmethylaminocarbonylmethyl)pyrazinone

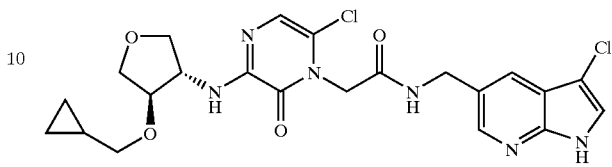

To a stirred solution of 3-(trans-3-cyclopropylmethoxytetrahydrofuran-4-ylamino)-6-chloro-1-carboxymethylpyrazinone from step 7 above (50 mg, 0.15 mmol) in DMF (1.0 mL) was added 5-aminomethyl-3-chloro-7-azaindole bis-hydrochloride salt (41 mg, 0.16 mmol) and HOBT (24 mg, 0.16 mmol). The solution was brought to pH 7 by the addition of DIEA (approximately 0.1 mL). EDC (70 mg, 0.24 mmol) was added and the solution was stirred at ambient temperature for 18 h. The reaction was concentrated in vacuo and partitioned between water and EtOAc. The organic phase was dried over MgSO$_4$, filtered, and concentrated in vacuo. The residue was purified by flash column chromatography using 9:1 CH$_2$Cl$_2$:MeOH as eluant. The free base of the title compound was dissolved in MeOH containing 3 equivalents of aqueous HCl and the solution was evaporated in vacuo to give the HCl salt of the title compound as an amorphous solid (45 mg, TLC Rf=0.46, 92:8:0.4 CH$_2$Cl$_2$:MeOH:NH$_4$OH; HPLC RT=8.6 min, method A; M+1 peak at m/z=508, electrospray mass spec).

EXAMPLE 74

3-(1-Methylsulfonyl-trans-4-(2-pyridyl)-pyrrolidin-3-ylamino)-6-chloro-1-(7-azaindol-5-ylmethylaminocarbonylmethyl)pyrazinone

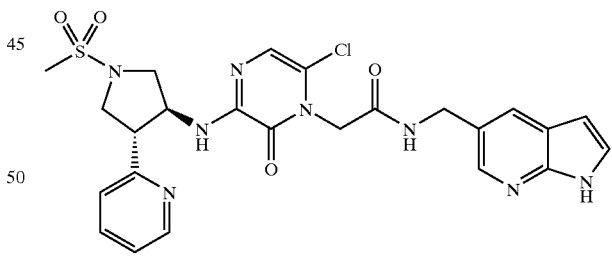

Step 1 Ethyl trans-3-(2-Pyridyl)acrylate

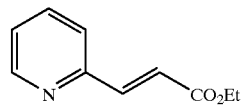

To a stirred solution of triethyl phosphonoacetate (10.5 g, 47 mmol) in THF (100 mL) at 0° C. was added sodium hydride (2.2 g of a 60% suspension in mineral oil, 55 mmol) in portions over a period of 30 min, followed by pyridine 2-carboxaldehyde (5.0 g, 47 mmol). The resulting solution was stirred at 0° C. for 1 h and then at ambient temperature for 18 h. The solution was diluted with EtOAc and water. The organic phase was separated, washed with water, dried over MgSO$_4$, filtered, and concentrated in vacuo. The residue was purified by flash column chromatography using a gradient elution of 15–25% EtOAc:hexanes to give the title compound as a colorless liquid (6.0 g; TLC Rf=0.5, 1:2 EtOAc:hexanes).

Step 2 1-Benzyl-trans-3-ethoxycarbonyl-4-(2-pyridyl)pyrrolidine

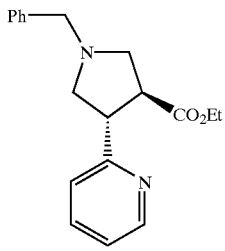

To a stirred solution of ethyl trans-3-(2-pyridyl)acrylate from step 1 above (4.0 g, 23 mmol) and N-trimethylsilylmethyl-N'-methoxymethylbenzylamine (8.1 g, 34 mmol; prepared according to the method of Terao et al., Chem. Pharm. Bull., 1985, vol. 33, p. 2762) in CH$_2$Cl$_2$ (30 mL) at 0° C. was added trifluoroacetic acid. (0.2 g, 1.7 mmol). The resulting solution was stirred at 0° C. for 4 h and then at ambient temperature for 18 h. Aqueous NaHCO$_3$ was added and the organic phase was separated, dried over MgSO$_4$, filtered, and concentrated in vacuo. The residue was purified by flash column chromatography using a gradient elution of 33–60% EtOAc:hexanes to give the title compound as an oil (5.1 g; TLC Rf=0.4, 1:1 EtOAc:hexanes; HPLC RT=4.16, method A).

Step 3 trans-3-Ethoxycarbonyl-4-(2-pyridyl)pyrrolidine

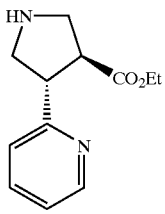

A solution of 1-benzyl-trans-3-ethoxycarbonyl-4-(2-pyridyl)pyrrolidine from step 2 above (5.0 g, 16 mmol) and 10% Pd on carbon (750 mg) in ethanol (30 mL) containing acetic acid (3 mL) was shaken under an atmosphere of hydrogen (40 psi) on a Parr apparatus at ambient temperature for 18 h. The catalyst was removed by filtration and the filtrate solvents were removed in vacuo. The residue was partitioned between CH$_2$Cl$_2$ and aqueous NaHCO$_3$. The organic phase was separated, dried over MgSO$_4$, filtered, and concentrated in vacuo to give the title compound as an oil (3.3 g; HPLC RT=2.43 min, method A).

Step 4 1-tert-Butyloxycarbonyl-trans-3-ethoxycarbonyl-4-(2-pyridyl)pyrrolidine

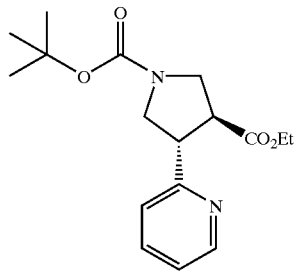

To a stirred solution of trans-3-ethoxycarbonyl-4-(2-pyridyl)pyrrolidine from step 3 above (3.3 g, 15 mmol) in DMF (15 mL) was added DIEA (2.6 mL, 15 mmol) and di-tert-butyl dicarbonate (3.7 g, 17 mmol). The resulting solution was stirred at ambient temperature for 18 h. The solvents were removed in vacuo and the residue was purified by flash column chromatography using a gradient elution of 25–55% EtOAc:hexanes to give the title compound as an oil (4.2 g, TLC Rf=0.4, 1:2 EtOAc:hexanes; HPLC RT=5.71 min, method A).

Step 5 1-tert-Butyloxycarbonyl-trans-4-(2-pyridyl)pyrrolidine-3-carboxylic Acid

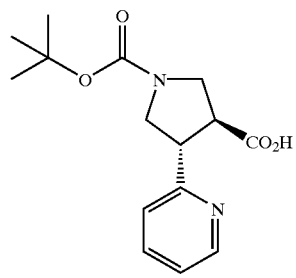

To a stirred solution of 1-tert-butyloxycarbonyl-trans-3-ethoxycarbonyl-4-(2-pyridyl)pyrrolidine from step 4 above (4.2 g, 13 mmol) in methanol (30 mL) was added aqueous NaOH (4.7 mL of a 4.0 N solution, 19 mmol). The resulting solution was stirred at ambient temperature for 48 h. The solution was acidified with aqueous HCl (3.1 mL of a 6.0 N solution, 19 mmol) and the solvents were removed in vacuo to give the title compound as an amorphous solid containing NaCl (HPLC RT=4.42 min, method A).

Step 6 1-tert-Butyloxycarbonyl-trans-3-benzyloxycarbonylamino-4-(2-pyridyl)pyrrolidine

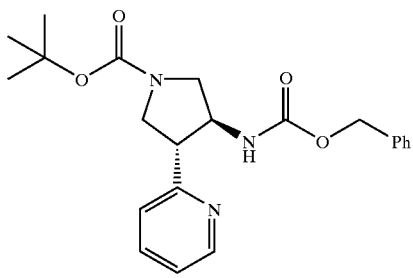

To a stirred solution of 1-tert-butyloxycarbonyl-trans-4-(2-pyridyl)pyrrolidine-3-carboxylic acid from step 5 above (13 mmol) in toluene (50 mL) was added DIEA (3.0 mL, 17 mmol). The solution was cooled to 0° C. and diphenylphosphoryl azide (4.1 g, 15 mmol) was added. The resulting solution was stirred at 0° C. for 1 h and at ambient temperature for 4 h. Benzyl alcohol (2.8 g, 26 mmol) was added and the solution was refluxed for 3 h. The solution was cooled to ambient temperature, diluted with EtOAc, and washed with aqueous NaHCO₃. The organic phase was separated, dried over MgSO₄, filtered, and the solvents were removed in vacuo. The residue was purified by flash column chromatography using a gradient elution of 10–25% EtOAc:hexanes to give the title compound as an oil (3.9 g, TLC Rf=0.4, 1:3 EtOAc-hexanes; HPLC RT=6.67 min, method A).

Step 7 1-tert-Butyloxycarbonyl-trans-3-amino-4-(2-pyridyl)pyrrolidine

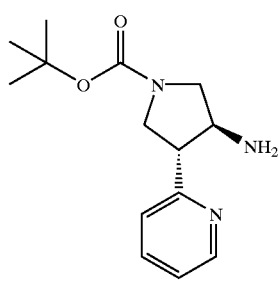

To a solution of 1-tert-butyloxycarbonyl-trans-3-benzyloxycarbonylamino-4-(2-pyridyl)pyrrolidine from step 6 above (3.9 g, 9.8 mmol) in EtOH (25 mL) was added 10% Pd on carbon (1.5 g). The mixture was shaken under an atmosphere of hydrogen (40 psi) at ambient temperature for 18 h on a Parr apparatus. The catalyst was removed by filtration and the solvent was removed in vacuo to give the title compound as an oil (2.5 g, HPLC RT=3.96 min, method A).

Step 8 3-(1-tert-Butyloxycarbonyl-trans-4-(2-pyridyl)-pyrrolidin-3-ylamino)-1-ethoxycarbonylmethylpyrazinone

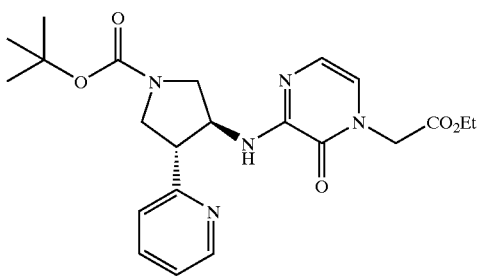

A stirred solution of 1-tert-butyloxycarbonyl-trans-3-amino-4-(2-pyridyl)pyrrolidine from step 7 above (2.5 g, 9.5 mmol), 3-bromo-1-ethoxycarbonylmethylpyrazinone (2.5 g, 9.5 mmol), and DIEA (1.9 mL, 11 mmol) in toluene (30 mL) was heated to reflux for 24 h. The mixture was cooled to ambient temperature, diluted with EtOAc, and washed with aqueous NaHCO₃. The organic phase was separated, dried over MgSO₄, filtered, and concentrated in vacuo. The residue was purified by flash column chromatography using a gradient elution of 60–85% EtOAc:hexanes to give the title compound as an amorphous solid (3.4 g; TLC Rf=0.5, 4:1 EtOAc:hexanes; HPLC RT=5.92 min, method A).

Step 9 3-(1-tert-Butyloxycarbonyl-trans-4-(2-pyridyl)-pyrrolidin-3-ylamino)-6-chloro-1-ethoxycarbonylmethylpyrazinone

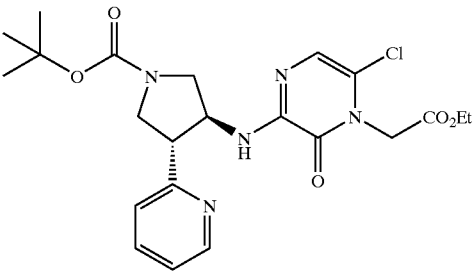

A stirred solution of 3-(1-tert-butyloxycarbonyl-trans-4-(2-pyridyl)-pyrrolidin-3-ylamino)-1-ethoxycarbonylmethylpyrazinone from step 8 above (2.0 g, 4.5 mmol) and N-chlorosuccinimide (0.67 g, 5.0 mmol) in CHCl3 was heated to reflux for 6 h. More N-chlorosuccinimide (0.20 g, 1.5 mmol) was added and refluxing was continued for 12 h. The reaction was diluted with CHCl3 and washed with aqueous NaHCO₃. The organic phase was separated, dried over Mg SO₄, filtered, and concentrated in vacuo. The residue was purified by flash column chromatography using a gradient elution of 25–50% EtOAc:hexanes to give the title compound as an amorphous solid (1.5 g, TLC Rf=0.5, 1:1 EtOAc:hexanes; HPLC RT=7.17 min, method A).

Step 10 3-(trans-4-(2-Pyridyl)-pyrrolidin-3-ylamino)-6-chloro-1-ethoxycarbonylmethylpyrazinone

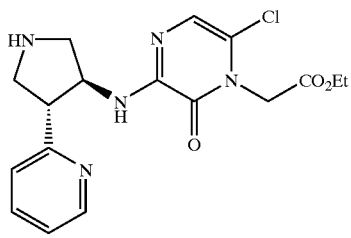

Into a stirred solution of 3-(1-tert-butyloxycarbonyl-trans-4-(2-pyridyl)-pyrrolidin-3-ylamino)-6-chloro-1-ethoxycarbonylmethylpyrazinone from step 9 above (0.8 g, 1.8 mmol) in EtOAc (25 mL) at 0° C. was bubbled HCl gas for 10 minutes. The mixture was stirred at 0° C. for 30 min and then at ambient temperature for 30 min. The solvent and excess HCl were removed in vacuo and the residue was triturated in ether to give the HCl salt of title compound as an amorphous solid (0.68 g, HPLC RT=4.54 min, method A).

Step 11 3-(1-Methylsulfonyl-trans-4-(2-pyridyl)-pyrrolidin-3-ylamino)-6-chloro-1-ethoxycarbonylmethylpyrazinone

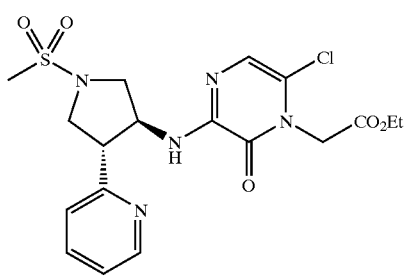

To a stirred solution of the hydrochloride salt of 3-(trans-4-(2-pyridyl)-pyrrolidin-3-ylamino)-6-chloro-1-ethoxycarbonylmethylpyrazinone from step 9 above (0.2 g, 0.48 mmol) in CH$_2$Cl$_2$ (20 mL) at 0° C. was added DIEA (0.30 mL, 1.7 mmol) and methanesulfonyl chloride (63 mg, 0.55 mmol). The resulting solution was stirred at 0° C. for 6 h and then at ambient temperature for 12 h. The mixture was diluted with CH$_2$Cl$_2$ and aqueous NaHCO$_3$. The organic phase was separated, dried over MgSO$_4$, filtered, and concentrated in vacuo. The residue was purified by column chromatography using a gradient elution of 2–4% MeOH:CH$_2$Cl$_2$ (0.20 g, TLC Rf=0.5, 95:5 CH$_2$Cl$_2$:MeOH; HPLC RT=5.47 min, method A).

Step 12 3-(1-Methylsulfonyl-trans-4-(2-pyridyl)-pyrrolidin-3-ylamino)-6-chloro-1-carboxymethylpyrazinone

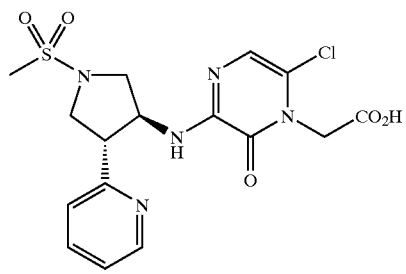

A solution of 3-(1-methylsulfonyl-trans-4-(2-pyridyl)-pyrrolidin-3-ylamino)-6-chloro-1-ethoxycarbonylmethylpyrazinone from step 11 above (0.20 g, 0.47 mmol) and aqueous NaOH (0.18 mL of a 4.0 N solution, 0.71 mmol) in EtOH (7 mL) was stirred at ambient temperature for 2 h. Aqueous HCl (0.12 mL of a 6.0 N solution, 0.72 mmol) was added, and the solvents were removed in vacuo to give the title compound as an amorphous solid containing NaCl (0.2 g, HPLC RT=3.99 min, method A).

Step 13 3-(1-Methylsulfonyl-trans-4-(2-pyridyl)-pyrrolidin-3-ylamino)-6-chloro-1-(7-azaindol-5-ylmethylaminocarbonylmethyl)pyrazinone

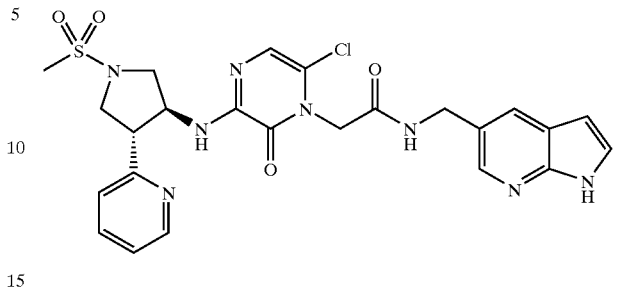

To a stirred solution of 3-(1-methylsulfonyl-trans-4-(2-pyridyl)-pyrrolidin-3-ylamino)-6-chloro-1-carboxymethylpyrazinone from step 12 above (0.16 mmol) in DMF (1.0 mL) was added 5-aminomethyl-7-azaindole bis-hydrochloride salt (36 mg, 0.16 mmol) and HOBT (24 mg, 0.16 mmol). The solution was brought to pH 7 by the addition of DIEA (approximately 0.1 mL). EDC (70 mg, 0.24 mmol) was added and the solution was stirred at ambient temperature for 18 h. The reaction was loaded directly onto an automated preparative HPLC unit and chromatographed using a gradient elution of 95:5:0.1 to 50:50:0.1 H$_2$O:CH$_3$CN:TFA. The fractions containing the desired product were combined and lyophilized to give the TFA salt of the title compound as an amorphous solid (65 mg, HPLC RT=4.07 min, method A; M+1 peak at m/z=557, electrospray mass spec).

What is claimed is:
1. A compound of the formula

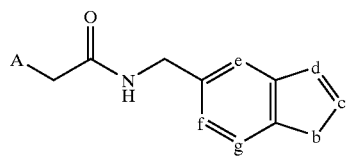

or a pharmaceutically acceptable salt thereof, wherein b is NY$^1$ or O; c is CY$^2$ or N; d is CY$^3$ or N; e is CY$^4$ or N; f is CY$^5$ or N; g is CY$^6$ or N, provided that 1) when e and f are N, g is CY$^6$, 2) when e and g are N, f is CY$^5$, and 3) when f and g are N, e is CY$^4$;

Y$^1$, Y$^2$, Y$^3$, Y$^4$, Y$^5$, and Y$^6$ are independently selected from the group consisting of hydrogen, C$_{1-4}$ alkyl, NH$_2$ and Cl;

A is

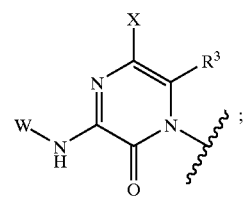

X is selected from the group consisting of hydrogen and halogen;
R$^3$ is selected from the group consisting of hydrogen and C$_{1-4}$ alkyl;

W is selected from the group consisting of hydrogen, $R^2$, $R^2SO2$, $R^2CH_2SO_2$, and

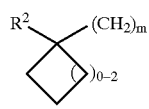

where m is 0–3, and
$R^2$ is selected from the group consisting of hydrogen, $C_{1-7}$ alkyl unsubstituted or substituted with phenyl, naphthyl or $C_{3-7}$ cycloalkyl.

2. A compound of claim 1, or a pharmaceutically acceptable salt thereof, wherein
$Y^1$, $Y^2$, $Y^3$, $Y^4$, $Y^5$, and $Y^6$ are independently selected from the group consisting of hydrogen, methyl, $NH_2$, or Cl;
W is selected from the group consisting of hydrogen,

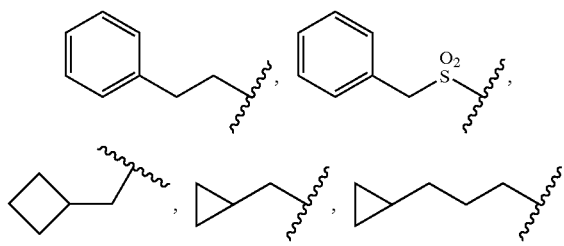

$CH_3CH_2CH_2$— or $(CH_3)_2CH_2$—; and
$R^3$ is selected from the group consisting of hydrogen and methyl.

3. A compound of claim 2, or a pharmaceutically acceptable salt thereof, wherein b is NH, $N(CH_3)$ or O; c is CH, $C(CH_3)$ or N; d is CH, N, $C(NH_2)$, $C(Cl)$, or $C(CH_3)$; e is CH, N or $C(CH_3)$; f is CH, $C(CH_3)$, or N; and g is CH or N.

4. A compound of claim 3, or a pharmaceutically acceptable salt thereof, selected from the group consisting of

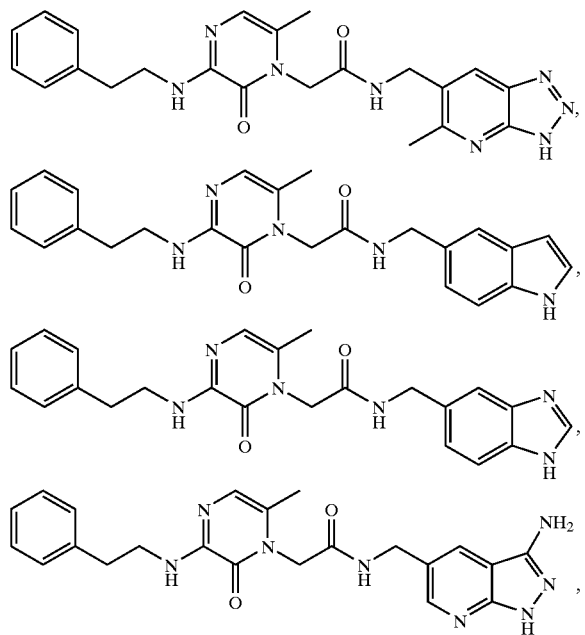

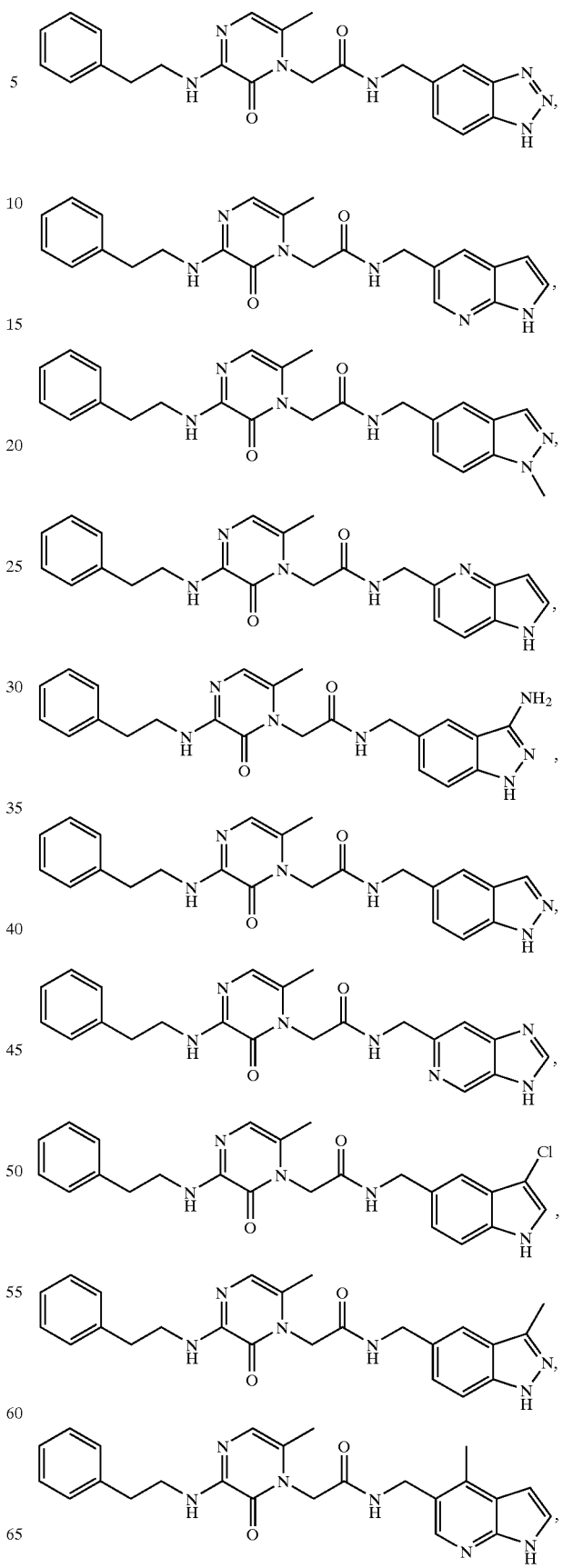

-continued
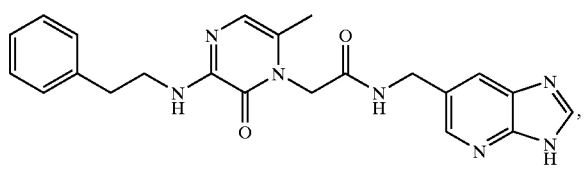
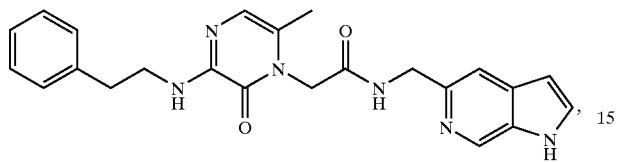
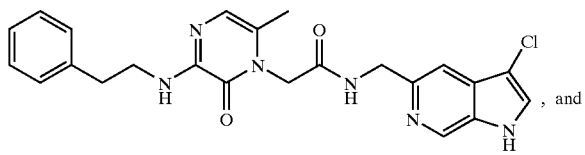
, and
-continued
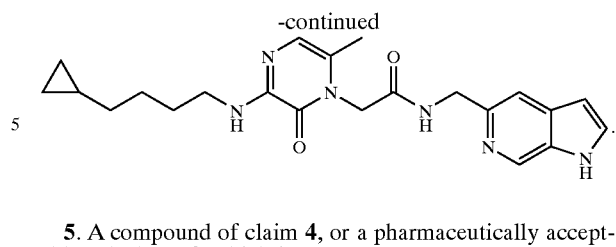
5. A compound of claim 4, or a pharmaceutically acceptable salt thereof, which is
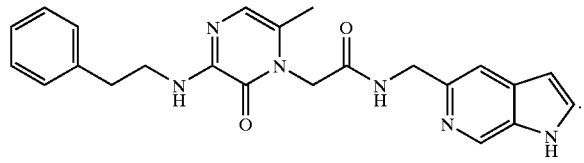
6. A pharmaceutical composition comprising a therapeutically effective amount of a compound of claim 1.
7. A method for inhibiting thrombus formation in blood comprising adding to the blood an effective amount of a composition of claim 6.
* * * * *